(12) United States Patent
Kreischer

(10) Patent No.: US 11,629,107 B2
(45) Date of Patent: Apr. 18, 2023

(54) HEAT EXCHANGE CONFIGURATIONS FOR OLIGOMERIZATION OF OLEFINS

(71) Applicant: Chevron Phillips Chemical Company LP, The Woodlands, TX (US)

(72) Inventor: Bruce E. Kreischer, Kingwood, TX (US)

(73) Assignee: Chevron Phillips Chemical Company, LP, The Woodlands, TX (US)

(*) Notice: Subject to any disclaimer, the term of this patent is extended or adjusted under 35 U.S.C. 154(b) by 0 days.

(21) Appl. No.: 17/871,471

(22) Filed: Jul. 22, 2022

(65) Prior Publication Data
US 2023/0085788 A1 Mar. 23, 2023

Related U.S. Application Data

(60) Provisional application No. 63/224,665, filed on Jul. 22, 2021.

(51) Int. Cl.
*C07C 2/32* (2006.01)
*B01J 19/00* (2006.01)

(52) U.S. Cl.
CPC ............ *C07C 2/32* (2013.01); *B01J 19/0006* (2013.01); *B01J 19/0013* (2013.01); *B01J 2219/0006* (2013.01); *B01J 2219/00065* (2013.01); *C07C 2531/22* (2013.01)

(58) Field of Classification Search
CPC ... C07C 2/32; C07C 2531/22; C07C 2/00–36; B01J 19/0006; B01J 19/0013; B01J 2219/0006; B01J 2219/00065
See application file for complete search history.

(56) References Cited

U.S. PATENT DOCUMENTS

| | | | |
|---|---|---|---|
| 5,928,699 A * | 7/1999 | Reznik | F25D 31/00 165/104.27 |
| 6,158,504 A | 12/2000 | Reznik | |
| 6,329,005 B1 | 12/2001 | Reznik | |
| 10,066,031 B1 * | 9/2018 | Kim | C07C 7/00 |
| 2005/0020866 A1 * | 1/2005 | Kobayashi | C08F 10/00 585/502 |
| 2012/0142989 A1 * | 6/2012 | Jaber | C07C 2/36 585/520 |
| 2013/0206357 A1 | 8/2013 | Chen | |
| 2017/0081256 A1 * | 3/2017 | Kreischer | B01J 19/18 |
| 2017/0081257 A1 * | 3/2017 | Kreischer | B01J 19/1818 |
| 2017/0190637 A1 * | 7/2017 | Emoto | C07C 2/32 |
| 2018/0030181 A1 * | 2/2018 | Emoto | C08F 10/02 |
| 2018/0179122 A1 * | 6/2018 | Boutrot | B01J 19/2465 |
| 2018/0354870 A1 * | 12/2018 | Wei | B01J 31/143 |
| 2021/0230085 A1 * | 7/2021 | Kim | C07C 11/107 |
| 2021/0340079 A1 * | 11/2021 | Kim | B01J 19/1862 |

* cited by examiner

*Primary Examiner* — Ali Z Fadhel
(74) *Attorney, Agent, or Firm* — Conley Rose, P.C.

(57) ABSTRACT

Disclosed herein are processes and reaction systems for controlling a temperature of an oligomerization reaction zone using a heat exchange system.

20 Claims, 4 Drawing Sheets

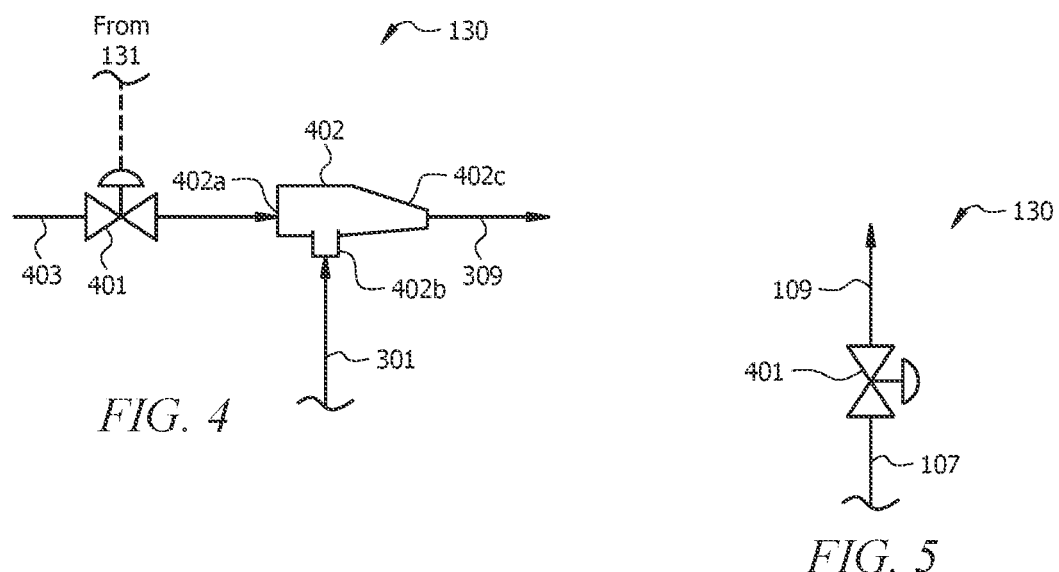
FIG. 4
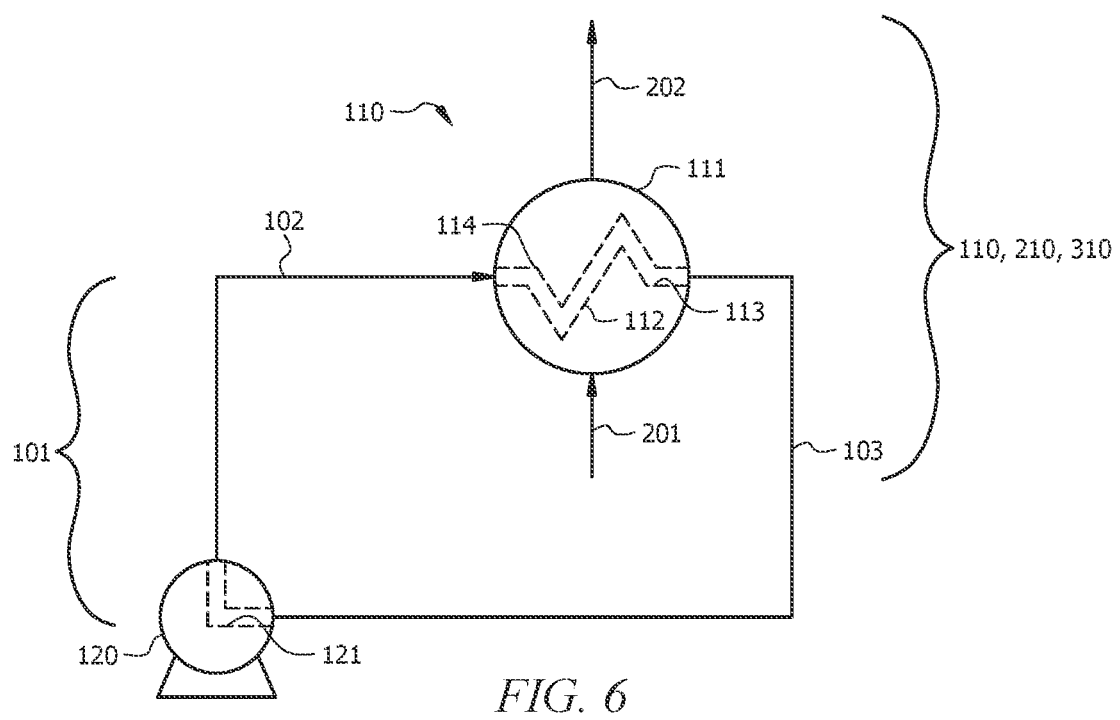
FIG. 5
FIG. 6

HEAT EXCHANGE CONFIGURATIONS FOR OLIGOMERIZATION OF OLEFINS

CROSS-REFERENCE TO RELATED APPLICATIONS

The present application is a non-provisional of and claims priority to U.S. Provisional Patent Application No. 63/224,665 filed Jul. 22, 2021 and entitled "Heat Exchange Configurations for Oligomerization of Olefins," which application is incorporated by reference herein in its entirety.

TECHNICAL FIELD

The present disclosure generally relates to heat exchange configurations for the oligomerization of olefins.

BACKGROUND

Reaction systems are used in a variety of industrial chemical processes, for example oligomerization and/or polymerization of olefins (commonly known as alkenes) to produce oligomers and/or polymers, respectively. For example, aluminum, nickel, zirconium, and iron based catalyst systems for the synthesis of $C_4$ to $C_{30+}$ alpha olefins from ethylene and chromium based catalyst systems for the selective synthesis of 1-hexene and/or 1-octene from ethylene constitute commercially significant processes for the preparation of alpha olefins. Ethylene oligomerization processes are extremely exothermic reactions and generate a significant amount of heat which must be removed from the oligomerization reaction mixture in order to maintain a stable reaction temperature. Failure to maintain a stable reaction temperature can lead to decreased catalyst system stability, decreased reaction system productivity, increased polymer formation, decreased reactor productivity, and decreased reactor online-time, among other undesirable effects. Heat exchange system design and control are important in controlling the ethylene oligomerization temperature by removing the heat generated during the ethylene oligomerization process and thus maintaining a stable reaction temperature. Demand for alpha olefins continues to rise, and alpha olefin producers seek adequate capacity to meet demand, for example new alpha olefin production processes and improved reaction systems and processes of making and using same.

SUMMARY

Disclosed herein is a process comprising: a) introducing at least 1) ethylene, 2) a catalyst system or catalyst system components comprising i) a heteroatomic ligand transition metal compound complex and an organoaluminum compound or ii) a heteroatomic ligand, a transition metal compound, and an organoaluminum compound, 3) optionally, an organic reaction medium, and 4) optionally, hydrogen into a reaction mixture within a reaction zone; b) forming an oligomer product in the reaction zone; and c) controlling a reaction mixture temperature within the reaction zone with a heat exchange system comprising a first heat exchanger providing indirect contact between at least a portion of the reaction mixture and a first heat exchange medium, the first heat exchanger comprising a first heat exchange surface having i) a first heat exchange surface first side in contact with the at least a portion of the reaction mixture, and ii) a first heat exchange surface second side in contact with the first heat exchange medium. In the process, a pressure on the first heat exchange surface second side is less than 1 atmosphere (101.3 kPa), and the first heat exchange medium has a boiling point at 1 atmosphere (101.3 kPa) greater than an average reaction mixture temperature on the first heat exchange surface first side and a boiling point at the pressure on the first heat exchange surface second side less than the average reaction mixture temperature on the first heat exchange surface first side. Also, in the process, a temperature difference between the average reaction mixture temperature on the first heat exchange surface first side and a first heat exchange medium temperature on the first heat exchange surface second side is less than 20° C.

Disclosed herein is another process comprising: a) introducing at least 1) ethylene, 2) a catalyst system or catalyst system components comprising i) a heteroatomic ligand transition metal compound complex and an organoaluminum compound or ii) a heteroatomic ligand, a transition metal compound, and an organoaluminum compound, 3) optionally, an organic reaction medium, and 4) optionally, hydrogen into a reaction mixture within a reaction zone; b) forming an oligomer product in the reaction zone; and c) controlling a pressure in a heat exchange system to provide a reaction mixture temperature within the reaction zone, the heat exchange system comprising a first heat exchanger providing indirect contact between at least a portion of the reaction mixture and a first heat exchange medium, the first heat exchanger comprising a first heat exchange surface having i) a first heat exchange surface first side in contact with the at least a portion of the reaction mixture, and ii) a first heat exchange surface second side in contact with the first heat exchange medium. In the process, a pressure on the first heat exchange surface second side is less than 1 atmosphere (101.3 kPa); and the first heat exchange medium has a boiling point at 1 atmosphere (101.3 kPa) greater than an average reaction mixture temperature on the first heat exchange surface first side and a boiling point at the pressure on the first heat exchange surface second side less than the average reaction mixture temperature on the first heat exchange surface first side. Also, in the process, a temperature difference between the average reaction mixture temperature on the first heat exchange surface first side and a first heat exchange medium temperature on the first heat exchange surface second side is less than 20° C.

Disclosed herein is a reaction system comprising: a) a reaction zone containing a reaction mixture; and b) a heat exchange system comprising a first heat exchanger configured to provide indirect contact between at least a portion of the reaction mixture and a first heat exchange medium, the first heat exchanger comprising a first heat exchange surface having i) a first heat exchange surface first side configured to contact the reaction mixture, and ii) a first heat exchange surface second side configured to contact the first heat exchange medium. In the reaction system, a pressure on the first heat exchange surface second side of the first heat exchanger is less than 1 atmosphere (101.3 kPa), and the first heat exchange medium has a boiling point at 1 atmosphere (101.3 kPa) greater than an average reaction mixture temperature on the first heat exchange surface first side and a boiling point at the pressure on the first heat exchange surface second side less than the average reaction mixture temperature on the first heat exchange surface first side. In the reaction system, a temperature difference between the average reaction mixture temperature on the first heat exchange surface first side and a first heat exchange medium temperature of the first heat exchange medium on the first heat exchange surface second side is less than 20° C.

BRIEF DESCRIPTION OF THE DRAWINGS

The following figures form part of the present specification and are included to further demonstrate certain aspects of the present invention. The invention may be better understood by reference to one or more of these figures in combination with the detailed description of specific embodiments presented herein.

FIG. 4 illustrates an eductor and valve as pressure control devices.

FIG. 5 illustrates a valve as a pressure control device.

FIG. 6 illustrates a reaction zone for a process and/or reaction system of FIG. 1, FIG. 2, and/or FIG. 3.

Figure 1:
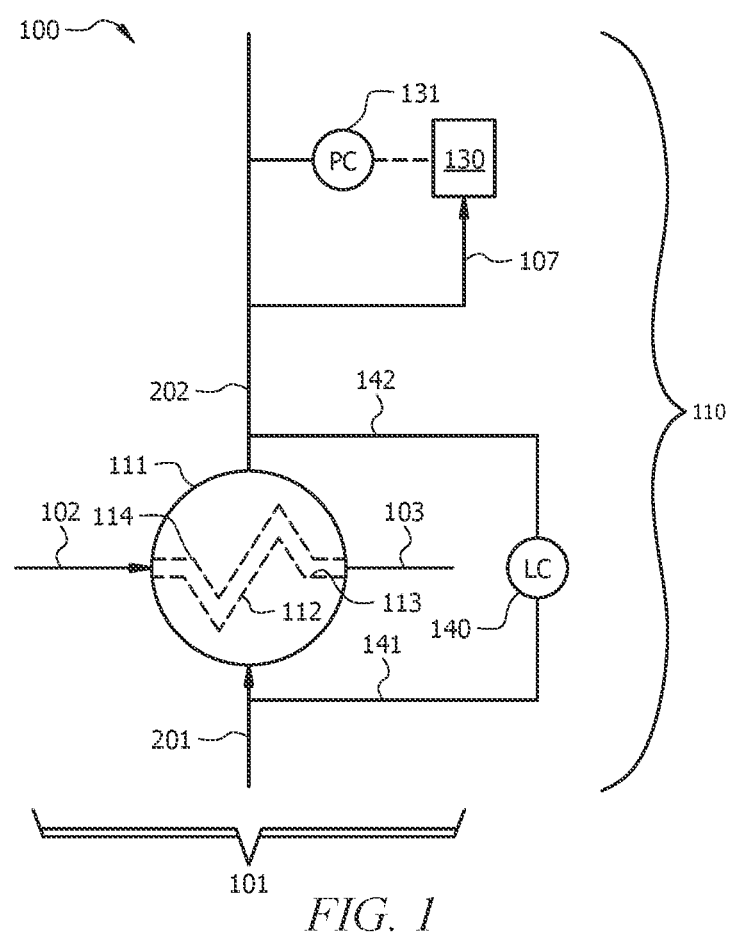
FIG. 1 illustrates a process and reaction system for controlling a temperature of a reaction mixture within an oligomerization reaction zone.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

DETAILED DESCRIPTION

Illustrative embodiments of the subject matter claimed below will now be disclosed. In the interest of clarity, not all features of an actual implementation are described in this specification. It can be appreciated that in the development of any such actual embodiment, numerous implementation-specific decisions must be made to achieve the developers' specific goals, such as compliance with system-related and business-related constraints, which can vary from one implementation to another. Moreover, it can be appreciated that such a development effort, even if complex and time-consuming, would be a routine undertaking for those of ordinary skill in the art having the benefit of this disclosure.

In the description herein, various ranges and/or numerical limitations can be expressly stated below. It should be recognized that unless stated otherwise, it is intended that endpoints are to be interchangeable. Further, any ranges include iterative ranges of like magnitude falling within the expressly stated ranges or limitations. In some instances, the description can use minimum values (or at least, or greater than or equal to values) and maximum values (or less than or equal to values) to describe numerical limitations. These minimum values and maximum values can be used, without limitation and in any combination to describe a range for described feature.

Furthermore, various modifications can be made within the scope of the invention as herein intended, and embodiments of the invention can include combinations of features other than those expressly claimed. In particular, flow arrangements other than those expressly described herein are within the scope of the invention.

Unless otherwise specified, the terms "contact" and "combine," and their derivatives, can refer to any addition sequence, order, or concentration for contacting or combining two or more components of the disclosed embodiments. Combining or contacting of oligomerization components can occur in one or more reaction zones under suitable contact conditions such as temperature, pressure, contact time, flow rates, etc.

Within this specification, the word "reactor" refers to a single piece of equipment such as, for example, a vessel, in which a reaction takes place, but excludes any associated equipment such as piping, pumps, and the like which is external to the vessel. Examples of reactors include stirred tank reactors (e.g., a continuous stirred tank reactor), plug flow reactors, or any other type of reactor.

Within this specification, term "reaction zone" refers to the portion of a reaction system where all the necessary reaction components and reaction conditions are present such that the reaction can occur at a desired rate. That is to say that the reaction zone begins where the necessary reaction components and reaction conditions are present to maintain the reaction within 25 percent of the average reaction rate and the reaction system ends where the conditions do not maintain a reaction rate within 25 percent of the average reaction rate (based upon a volume average of the reaction rate of the reaction zone). For example, in terms of an ethylene oligomerization process, the reaction zone begins at the point where sufficient ethylene and active catalyst system is present under the sufficient reaction conditions (e.g., temperature and/or pressure, among others) to maintain oligomer product production at the desired rate and the reaction zone ends at a point where either the catalyst system is deactivated, sufficient ethylene is not present to sustain oligomer product production, or other reaction conditions (e.g., temperature and/or pressure, among others) are not sufficient to maintain the oligomer product production or the desired oligomer product production rate. Within this specification the "reaction zone" can comprise one or more reactors. The term "reaction zone" can be qualified to refer to more specific "reaction zones" by use of additional qualifying terms. For example, the use of the term "oligomerization reaction zone" indicates that the desired reaction within the "reaction zone" is an oligomerization.

The term "reaction system" refers to all of the equipment to produce a product. The term "reaction system" includes reactors, reaction zones, and all the associated equipment, associated process lines, and control equipment which can bring the necessary component(s) into and out of the reaction system and control the reaction with the reactor(s)/reaction zone(s) of the reaction system. Within this specification the "reaction system" can comprise one or more reactor zones, one or more reactors, and associated equipment to produce a product. The term "reaction system" can be qualified to refer to more specific "reaction systems" by use of additional qualifying terms. For example, the use of the term "oligomerization reaction system" indicates that the "reaction system" relates to an oligomerization.

Unless otherwise indicated, the definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition can be applied. To the extent that any definition or usage provided by any document incorporated herein by reference conflicts with the definition or usage provided herein, the definition or usage provided herein controls.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to hexene includes 1-hexene, 2-hexene, 3-hexene, and any other hydrocarbon having 6 carbon atoms (linear, branched or cyclic) and a single carbon carbon double bond. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure of a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" definition includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the process described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while an ether group can complex with a metal compound, an ether group located at a para position of a substituted phenyl phosphinyl group can be an inert functional group because a single metal compound cannot complex with both the para ether group and the $N^2$-phosphinyl formamidine group of the same metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), and/or sulfidyl groups, among others.

The term "hydrocarbon" whenever used in this specification and claims refers to a compound containing only carbon and hydrogen. Other identifiers can be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group" "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from the carbon atom of an aliphatic compound. Aliphatic compounds and therefore aliphatic groups can contain organic functional group(s) and/or atom(s) other than carbon and hydrogen.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "reaction zone effluent," and it derivatives (e.g., oligomerization reaction zone effluent, trimerization reaction zone effluent, tetramerization reaction zone effluent, or trimerization and tetramerization reaction zone effluent) generally refers to all the material which exits the reaction zone through a reaction zone outlet/discharge which discharges a reaction mixture and can include reaction zone feed(s) (e.g., olefin, catalyst system or catalyst system components, and/or solvent), and/or reaction product (e.g., oligomer product including oligomers and non-oligomers, trimerization product including trimer and non-trimer, tetramerization product including tetramer and non-tetramer, or trimerization and tetramerization product including trimer and tetramer and non-trimer and tetramer). The term "reaction zone effluent" and its derivatives can be qualified to refer to certain portions by use of additional qualifying terms. For example, while reaction zone effluent refers to all material which exits the reaction zone through the reaction zone outlet/discharge, a reaction zone oligomer product effluent refers to only the oligomer product within the reaction zone effluent.

As utilized in the present application and claims, the word "control" and its derivatives (e.g., "controlling" and "controlled", among any others) is intended to apply to situation where the particular parameter is actively maintained, adjusted, increased, and/or decreased unless specifically indicated otherwise. For example, a reference to controlling a reaction mixture temperature includes situations where the reaction temperature is actively maintained, adjusted, increased, and/or decreased.

Disclosed herein are processes and reaction systems for controlling a temperature of an oligomerization reaction zone. Oligomerization reactions are exothermic in nature, and thus produce heat that must be removed from the reaction zone in order to control the temperature of the reaction zone.

In an aspect, the present application relates to a process comprising providing or controlling a reaction mixture temperature (or average reaction mixture temperature) within a reaction zone with a heat exchange system, the heat exchange system comprising a first heat exchanger providing indirect contact between at least a portion of the reaction mixture and a first heat exchange medium, the first heat exchanger comprising a first heat exchange surface having i) a first heat exchange surface first side in contact with at least a portion of the reaction mixture and ii) a first heat exchange surface second side in contact with the first heat exchange medium; where a pressure on the first heat exchange surface second side (or on the first heat exchange medium) can be, or can be controlled to be, less than 1 atmosphere (101.3 kPa). The process comprising controlling (or providing) a reaction mixture temperature within the reaction zone can further comprise providing or controlling the pressure on the first heat exchange surface second side (or first heat exchange medium) to control the reaction mixture temperature (or average reaction mixture temperature) within the reaction zone. In another aspect, the present application relates to a comprising providing or controlling a pressure in a heat exchange system to provide a reaction mixture temperature (or average reaction mixture temperature) within a reaction zone, the heat exchange system comprising a first heat exchanger providing indirect contact between the reaction mixture and a first heat exchange medium, the first heat exchanger comprising a first heat exchange surface having i) a first heat exchange surface first side in contact with the reaction mixture and ii) a first heat exchange surface second side in contact with the first heat exchange medium; where a pressure on the first heat exchange surface second side of the first heat exchanger can be or can be controlled to be less than 1 atmosphere (101.3 kPa). The process comprising providing or controlling a pressure in a heat exchange system can further comprise controlling the reaction mixture temperature (or average reaction mixture temperature) within a reaction zone. In yet another aspect, the present application relates to a reaction system comprising: a) a reaction zone containing a reaction mixture; and b) a heat exchange system comprising a first heat exchanger configured to provide indirect contact between the reaction mixture and a first heat exchange medium, the first heat exchanger comprising a first heat exchange surface having i) a first heat exchange surface first side configured to contact the reaction mixture, and ii) a first heat exchange surface second side configured to contact a first heat exchange medium; where a pressure on the first heat exchange surface second side can be or can be controlled to be less than 1 atmosphere (101.3 kPa).

The first heat exchange medium can have a boiling point at 1 atmosphere (101.3 kPa) greater than an average reaction mixture temperature on the first heat exchange surface first side and can have a boiling point at the pressure on the first heat exchange surface second side less than the average reaction mixture temperature on the first heat exchange surface first side. Generally, the first heat exchange medium can have any boiling point at 1 atmosphere (101.3 kPa) which can provide a desired boiling point at the pressure on the first heat exchange surface second side that is less than the average reaction mixture temperature on the first heat exchange surface first side. Additional aspects of the first heat exchange medium (e.g., potential first heat exchange mediums and physical properties such as potential boiling point, among other things) are independently described herein and can be utilized without limitation and in any combination to further describe the first heat exchange medium utilized in the processes described herein.

When the reaction mixture temperature (or the average reaction mixture temperature) within the reaction zone (or on the first heat exchange surface first side) is greater than boiling point of the first heat exchange medium on the first heat exchange surface second side, both liquid phase of the first heat exchange medium and vapor phase of the first heat exchange medium can be present in the heat exchange system (or in the first heat exchanger). As such, in an aspect, a first part of at least a portion of the reaction mixture on the first heat exchange surface first side can indirectly contact a liquid phase of the first heat exchange medium on the first heat exchange surface second side, and a second part of the at least a portion of the reaction mixture on the first heat exchange surface first side can indirectly contact a vapor phase of the first heat exchange medium that are on the first heat exchange surface second side. As such, there can be a first level of a liquid phase of the first heat exchange medium on the first heat exchange surface second side. In an aspect, the first level of a liquid phase of the first heat exchange medium on the first heat exchange surface second side can be controlled. In another aspect, controlling (maintaining, adjusting, increasing and/or decreasing) the first level of the liquid phase of the first heat exchange medium on the first heat exchange surface second side can be utilized to control the reaction mixture temperature (or average reaction mixture temperature) on the first heat exchange surface first side.

The amount of the reaction mixture that can indirectly contact liquid phase of the first heat exchange medium or the first level of the liquid phase of the first heat exchange medium on the first heat exchange surface second side can be provided as 1) a percentage of the at least a portion of the reaction mixture on the first heat exchange surface first side which indirectly contacts the liquid phase of the first heat exchange medium on the first heat exchange surface second side; 2) a percentage of the surface area of the first heat exchange surface second side which contacts the liquid phase of the first heat exchange medium; 3) a volume ratio of the liquid phase of the first heat exchange medium in the first heat exchanger (or on the first heat exchange surface second side) to the vapor phase of the first heat exchange medium in the first heat exchanger (or on the first heat exchange surface second side); or 4) any combination thereof. The percentage of the at least a portion of the reaction mixture on the first heat exchange surface first side which indirectly contacts a liquid phase of the first heat exchange medium on the first heat exchange surface second side can be, or can be controlled to be greater than or equal to 50%, 60%, 70%, 75%, 80%, or 90% by volume; alternatively or additionally, less than or equal to 95%, 90%, 85%, 80%, 75%, or 70% by volume. In an aspect, the percentage of the at least a portion of the reaction mixture on the first heat exchange surface first side which indirectly contacts a liquid phase of the first heat exchange medium on the first heat exchange surface second side can be or can be controlled to be in a range from any minimum percentage disclosed herein to any maximum percentage disclosed herein. In some non-limiting aspects, the percentage of the at least a portion of the reaction mixture on the first heat exchange surface first side which indirectly contacts a liquid phase of the first heat exchange medium on the first heat exchange surface second side can be or can be controlled to be in a range from 50% to 95%, from 60% to 95%, from 60% to 90%, from 70% to 90%, from 70% to 85%, or from 75% to 85%, by volume. Other percentages of the at least a portion of the reaction mixture on the first heat exchange surface first side which indirectly contacts a liquid phase of the first heat exchange medium on the first heat exchange surface second side are readily apparent to those skilled in the art with the aid of this disclosure. The percentage of the surface area of the first heat exchange surface second side which contacts the liquid phase of the first heat exchange medium can be or can be controlled to be at least 50%, 60%, 70%, 75%, 80%, or 90%; alternatively or additionally, less than or equal to 95%, 90%, 85%, 80%, 75%, or 70%. In an aspect, the percentage of the surface area of the first heat exchange surface second side which contacts the liquid phase of the first heat exchange medium can be or can be controlled to be in a range from any minimum percentage disclosed herein to any maximum percentage disclosed herein. In some non-limiting aspects, the percentage of the surface area of the first heat exchange surface second side which contacts the liquid phase of the first heat exchange medium can be or can be controlled to be in a range from 50% to 95%, from 60% to 95%, from 60% to 90%, from 70% to 90%, from 70% to 85%, or from 75% to 85%. Other percentages of the surface area of the first heat exchange surface second side which contacts the liquid phase of the first heat exchange medium are readily apparent to those skilled in the art with the aid of this disclosure. The volume ratio of the liquid phase of the first heat exchange medium in the first heat exchanger (or on the first heat exchange surface second side) to the vapor phase of the first heat exchange medium in the first heat exchanger (or on the first heat exchange surface second side) can be or can be controlled to be greater than or equal to 1:1, 1.5:1, 2:1, 2.5:1, 3:1, 3.5:1, or 4:1; alternatively or additionally, less than or equal to 20:1, 10:1, 6:1, 4:1, 3:1, or 2.5:1. In an aspect, the volume ratio of the liquid phase of the first heat exchange medium in the first heat exchanger (or on the first heat exchange surface second side) to the vapor phase of the first heat exchange medium in the first heat exchanger (or on the first heat exchange surface second side) can be or can be controlled to be in a range from any minimum percentage disclosed herein to any maximum percentage disclosed herein. In some non-limiting aspects, the volume ratio of the liquid phase of the first heat exchange medium in the first heat exchanger (or on the first heat exchange surface second side) to the vapor phase of the first heat exchange medium in the first heat exchanger (or on the first heat exchange surface second side) can be or can be controlled to be in a range from 1:1 to 20:1, from 1.5:1 to 20:1, from 1.5:1 to 9:1, from 2:1 to 9:1, from 2.5:1 to 6:1, or from 3:1 to 6.1; among other ratios disclosed herein. Other volume ratios of the liquid phase of the first heat exchange medium in the first heat exchanger (or on the first heat exchange surface second side) to the vapor phase of the first heat exchange medium in the first heat exchanger (or on the first heat exchange surface second side) are readily apparent to those skilled in the art with the aid of this disclosure.

The heat exchange system of the processes and/or reaction systems described herein can further comprise a second heat exchanger providing indirect contact between the first heat exchange medium and a second heat exchange medium, the second heat exchanger comprising a second heat exchange surface having i) a second heat exchange surface first side in contact with the first heat exchange medium, and ii) a second heat exchange surface second side in contact with the second heat exchange medium where a pressure on the second heat exchange surface first side of the second heat exchanger can be or can be controlled to be a pressure less than 1 atmosphere (101.3 kPa). In an aspect, the second heat exchange surface does not contact the reaction mixture. In an aspect, the heat exchange system can further comprise a plurality of conduits connecting the first heat exchanger and the second heat exchanger and allowing for flow of the first heat exchange medium between the first heat exchange surface second side and the second heat exchange surface first side. At least one of one or more conduits can allow for flow of the first heat exchange medium from the first heat exchange surface second side to the second heat exchange surface first side and at least one of the one or more conduits can allow for flow of the first heat exchange medium from the second heat exchange surface first side to the first heat exchange surface second side. When the heat exchange system contains a liquid phase of the first heat exchange medium and a vapor phase of the first heat exchange medium, at least one of one or more conduits can allow for flow of vapor phase of the first heat exchange medium from the first heat exchange surface second side to the second heat exchange surface first side, and at least one of the one or more conduits can allow for flow of liquid phase of the first heat exchange medium from the second heat exchange surface first side to the first heat exchange surface second side.

Generally, the first and second heat exchange surfaces can have any orientation that can provide the desired indirect contact between the reaction mixture and the first heat exchange medium or the first heat exchange medium and second heat exchange medium. The first heat exchange surface can comprise horizontally oriented tubes or plates, or vertically oriented tubes or plates; alternatively, horizontally oriented tubes or plates; or alternatively, vertically oriented tubes or plates. The second heat exchange surface can comprise horizontally oriented tubes or plates, or vertically oriented tubes or plates; alternatively, horizontally oriented tubes or plates; or alternatively, vertically oriented tubes or plates. In an aspect, the first heat exchange surface can comprise horizontally oriented tubes or plates, and the second heat exchange surface can comprise vertically oriented tubes or plates.

In aspects where the heat exchange system contains both liquid phase of the first heat exchange medium and vapor phase of the first heat exchange medium, liquid phase and vapor phase of the first heat exchange medium can contact the second heat exchange surface first side (or indirectly contact the second heat exchange medium). In this aspect, a first part of the at least a portion of the reaction mixture on the first heat exchange surface first side indirectly contacts a liquid phase of the first heat exchange medium on the first heat exchange surface second side, and a second part of the at least a portion of the reaction mixture on the first heat exchange surface first side indirectly contacts a vapor phase of the first heat exchange medium on the first heat exchange surface second side; and at least a first part of the second heat exchange medium on the second heat exchange surface second side indirectly contacts the vapor phase of the first heat exchange medium on the second heat exchange surface first side, and a second part of the second heat exchange medium on the second heat exchange surface second side indirectly contacts liquid phase of the first heat exchange medium on the second heat exchange surface first side. In this aspect, there can be a second level of liquid phase of the first heat exchange medium on second heat exchange surface first side. The first level of the liquid phase of the first heat exchange medium is described herein and can be utilized without limitation to described the first level of the first heat exchange medium in aspect where the heat exchange system includes the first heat exchanger and the second heat exchanger. Generally, the second level of liquid phase of the first heat exchange medium can be any level provided herein. The second level of liquid phase of the first heat exchange medium can be provided as 1) a percentage of the second heat exchange medium on the second heat exchange surface second side which indirectly contacts the liquid phase of the first heat exchange medium on the second heat exchange surface first side; 2) a volume ratio of liquid phase of the first heat exchange medium in the second heat exchanger (or on the second heat exchange surface first side) to vapor phase of the first heat exchange medium in the second heat exchanger (or on the second heat exchanger surface first side); or 3) any combination thereof. The percentage of the second heat exchange medium on the second heat exchange surface second side which indirectly contacts the liquid phase of the first heat exchange medium on the second heat exchange surface first side can be or can be controlled to be least 50%, 60%, 70%, 80%, or 90%, by volume; alternatively or additionally, less than or equal to 95%, 90%, 85%, 80%, 75%, or 70%, by volume. In an aspect, the second heat exchange medium on the second heat exchange surface second side which indirectly contacts the liquid phase of the first heat exchange medium on the second heat exchange surface first side can be or can be controlled to be in a range from any minimum percentage disclosed herein to any maximum percentage disclosed herein. In some non-limiting aspects, the second heat exchange medium on the second heat exchange surface second side which indirectly contacts the liquid phase of the first heat exchange medium on the second heat exchange surface first side can be or can be controlled to be in a range from 50% to 95%, from 60% to 95%, from 60% to 90%, from 70% to 90%, from 70% to 85%, or from 75% to 85%, by volume. Other percentages of the second heat exchange medium on the second heat exchange surface second side which indirectly contacts the liquid phase of the first heat exchange medium on the second heat exchange surface first side are readily apparent to those skilled in the art with the aid of this disclosure. The volume ratio of the liquid phase of the first heat exchange medium in the second heat exchanger (or on the second heat exchange surface first side) to the vapor phase of the first heat exchange medium in the second heat exchanger (or on the second heat exchange surface first side) can be or can be controlled to be greater than or equal to 1:1, 1.5:1, 2:1, 2.5:1, 3:1, 3.5:1, or 4:1; alternatively or additionally, less than or equal to 20:1, 10:1, 6:1, 4:1, 3:1, or 2.5:1. In an aspect, the volume ratio of the liquid phase of the first heat exchange medium in the second heat exchanger (or on the second heat exchange surface first side) to the vapor phase of the first heat exchange medium in the second heat exchanger (or on the second heat exchange surface first side) can be or can be controlled to be in a range from any minimum percentage disclosed herein to any maximum percentage disclosed herein. In some non-limiting aspects, the volume ratio of the liquid phase of the first heat exchange medium in the second heat exchanger (or on the second heat exchange surface first side) to the vapor phase of the first heat exchange medium in the second heat exchanger (or on the second heat exchange surface first side) can be or can be controlled to be in a range from 1:1 to 20:1, from 1.5:1 to 20:1, from 1.5:1 to 9:1, from 2:1 to 9:1, from 2.5:1 to 6:1, or from 3:1 to 6.1. Other volume ratios of the liquid phase of the first heat exchange medium in the second heat exchanger (or on the second heat exchange surface first side) to the vapor phase of the first heat exchange medium in the second heat exchanger (or on the second heat exchange surface first side) are readily apparent to those skilled in the art with the aid of this disclosure. In an aspect, the second level of the liquid phase of the first heat exchange medium on the second heat exchange surface first side is vertically higher relative to a common reference point on the ground than the first level of the liquid phase of the first heat medium on the first heat exchange surface second side. The second heat exchange surface first side being vertically higher relative to a common reference point on the ground than the first level of the liquid phase of the first heat medium on the first heat exchange surface second side enables the use of gravity to allow flow of the liquid phase of the first heat exchange medium from the second heat exchanger (or the second heat exchange surface first side) to the first heat exchanger (or the first heat exchange surface second side). Additionally, the second heat exchange surface first side being vertically higher relative to a common reference point on the ground than the first level of the liquid phase of the first heat medium on the first heat exchange surface second side enables the use of the second level of liquid phase of the first heat exchange medium as a method to control the pressure on the first heat exchange surface second side and/or the pressure on the second heat exchange surface first side (and/or the first heat exchange medium).

Generally, for any process and/or reaction system described herein, the pressure less than 1 atmosphere (101.3 kPa) on the first heat exchange surface second side (and/or the second heat exchange surface first side and/or the first heat exchange medium) can be any pressure which provides or can control a desired reaction mixture temperature (or average reaction mixture temperature). The pressure less than 1 atmosphere (101.3 kPa) can be a minimum pressure of 0.1, 0.12, 0.15, 0.2, 0.25, 0.3, 0.375, or 0.45 atmospheres; alternatively or additionally, a maximum pressure of 0.9, 0.875, 0.85, 0.8, 0.75, or 0.7 atmospheres. The pressure less than 1 atmosphere (101.3 kPa) can range from any minimum pressure described herein to any maximum pressure described herein. Non-limiting examples for pressures less than 1 atmosphere (101.3 kPa) include a pressure in the range of 0.1 to 0.9, 0.12 to 0.9, 0.15 to 0.875, 0.2 to 0.875, 0.3 to 0.85, 0.375 to 0.85, or 0.45 to 0.85 atmospheres. Other suitable ranges for the pressure less than 1 atmosphere (101.3 kPa) on the first heat exchange surface second side (or second heat exchange surface first side or the first heat exchange medium) are readily apparent from the present disclosure.

The heat exchange system of the processes and/or reaction systems described herein can be utilized to provide and/or control the reaction mixture temperature (or average reaction mixture temperature) in the reaction zone (or contacting the first heat exchange surface first side). Generally, the reaction mixture temperature (or average reaction mixture temperature) in the reaction zone (or on the first heat exchange surface first side) can be any reaction mixture temperature (or average reaction mixture temperature) greater than the boiling point of the boiling point of the first heat exchange medium at the pressure of less than 1 atmosphere (101.3 kPa) on the first heat exchange surface second side (or second heat exchange surface first side or the first heat exchange medium). The reaction mixture temperature (or the average reaction mixture temperature) in the reaction zone (or on the first heat exchange surface second side) can have a minimum temperature of 0° C. 25° C., 40° C., 50° C., 60° C., 70° C., or 75° C.; alternatively or additionally, a maximum temperature of 120° C. 110° C., 100° C., or 95° C. or 90° C. The reaction mixture temperature (or the average reaction mixture temperature) in the reaction zone (or on the first heat exchange surface second side) can range from any minimum temperature disclosed herein to any maximum temperature disclosed herein. Non-limiting ranges for the reaction mixture temperature (or the average reaction mixture temperature) in the reaction zone (or on the first heat exchange surface second side) can be in a range from 0° C. to 120° C., from 25° C. to 120° C., from 40° C. to 110° C., from 50° C. to 100° C., from 50° C. to 100° C., from 60° C. to 95° C. from 70° C. to 95° C., from 75° C. to 95° C., or from 75° C. to 90° C. Other suitable ranges for the reaction mixture temperature (or the average reaction mixture temperature) in the reaction zone (or on the first heat exchange surface second side) are readily apparent from the present disclosure.

Generally, the processes and reaction systems described herein can have any pressure less than 1 atmosphere (101.3 kPa) described herein on the first heat exchange surface second side (or second heat exchange surface first side or first heat exchange medium). Generally, the pressure less than less than 1 atmosphere (101.3 kPa) can be supplied by any means capable of providing and/or controlling a pressure less than 1 atmosphere (101.3 kPa). In an aspect, the heat exchange system of the processes and/or reaction systems described herein can further comprise one or more pressure control devices. In an aspect, the one or more pressure control devices can be fluidly connected to the first heat exchange surface first side; alternatively, or additionally fluidly connected to the second heat exchange surface first side. In another aspect, at least one of the one or more pressure control devices can be in fluid communication with (fluidly connected to) at least one of the plurality of conduits; alternatively, in fluid communication with (fluidly connected to) at least one of the plurality of conduits allowing for flow of the first heat exchange medium between the first heat exchanger and the second heat exchanger; or alternatively, in fluid communication with a conduit allowing for flow of the first heat exchange medium from the first heat exchange surface second side to the second heat exchange surface first side. Pressure control devices are independently described herein, and these independently described pressure control devices can be utilized without limitation to further describe the process and reaction systems described herein. In an aspect, the one or more pressure control devices can provide an initial pressure less than 1 atmosphere (101.3 kPa), as described herein, on the first heat exchange surface second side (and/or second heat exchange surface first side and/or first heat exchange medium), can provide or control the pressure on the first heat exchange surface second side (and/or second heat exchange surface first side and/or first heat exchange medium), can provide or control the first level of the liquid phase of the first heat exchange medium on the first heat exchange surface second side, can remove non-condensable components from the first heat exchange medium, or any combination thereof; alternatively, the one or more pressure control devices can provide an initial pressure less than 1 atmosphere (101.3 kPa), as described herein, on the first heat exchange surface second side; alternatively, can control the pressure on the first heat exchange surface second side (and/or second heat exchange surface first side and/or first heat exchange medium), or control the first level of the liquid phase of the first heat exchange medium on the first heat exchange surface second side; alternatively, can control the pressure on the first heat exchange surface second side; alternatively, can control the first level of the liquid phase of the first heat exchange medium on the first heat exchange surface second side (and/or second heat exchange surface first side and/or first heat exchange medium); or alternatively, can remove non-condensable components from the first heat exchange medium. In an aspect, the pressure on the first heat exchange surface second side (and/or the second heat exchange surface first side, and/or the first heat exchange medium) can be provided or controlled by a set point on at least one of the one or more pressure control devices.

Since the first heat exchange medium indirectly contacts the reaction mixture through the first heat exchange surface, the reaction mixture temperature (or the average reaction mixture temperature) in the reaction zone (or on the first heat exchange surface first side) can be controlled by controlling a parameter affecting the temperature of the first heat exchange medium and/or a parameter affecting the indirect contact of the reaction mixture and the first heat exchange medium through the first heat exchange surface. Non-limiting parameters which can affect the temperature of the first heat exchange medium or a parameter affecting the indirect contact of the reaction mixture and the first heat exchange medium through the first heat exchange surface (which in turn can be used to control the reaction mixture temperature or the average reaction mixture temperature) can include the pressure on the first heat exchange surface second side (and/or on the second heat exchange surface first side, and/or on the first heat exchange medium), the first level of the liquid phase of the first heat exchange medium on the first heat exchange surface second side, and the second level of the liquid phase of the first heat exchange medium on the second heat exchange surface first side, among other parameters. In an aspect, controlling the reaction mixture temperature (or the average reaction mixture temperature) in the reaction zone (or on the first heat exchange surface first side) can comprise controlling the pressure on the first heat exchange surface second side (and/or second heat exchange surface first side, and/or the first heat exchange medium), controlling the first level of the liquid phase of the first heat exchange medium on the first heat exchange surface second side, controlling the second level of the liquid phase of the first heat exchange medium on the second heat exchange surface first side, or any combination thereof; controlling the pressure on the first heat exchange surface second side (and/or second heat exchange surface first side, and/or the first heat exchange medium), controlling the first level of the liquid phase of the first heat exchange medium on the first heat exchange surface second side, or any combination thereof; alternatively, controlling the pressure on the first heat exchange surface second side (or on the first heat exchange medium or on the second heat exchange surface first side); alternatively, controlling the first level of the liquid phase of the first heat exchange medium on the first heat exchange surface second side; or alternatively, controlling the second level of the liquid phase of the first heat exchange medium on the second heat exchange surface first side. In an aspect, controlling the reaction mixture temperature (or average reaction mixture temperature) can comprise controlling the pressure on the first heat exchange surface first side and on the second heat exchange surface first side by controlling the pressure provided by the one or more pressure control devices.

In an aspect, controlling the first level of the liquid phase of the first heat exchange medium (or controlling the reaction mixture temperature or average reaction mixture temperature in the reaction zone) can comprise a) controlling a second level of a liquid phase of the first heat exchange medium on the second heat exchange surface first side; b) adding first heat exchange medium to the heat exchange system or removing a portion of the first heat exchange medium from the heat exchange system; c) controlling the pressure on the first heat exchange surface second side (and/or first heat exchange medium, and/or second heat exchange surface first side); or d) any combination thereof; alternatively, controlling a second level of a liquid phase of the first heat exchange medium on the second heat exchange surface first side; adding first heat exchange medium to the heat exchange system or removing a portion of the first heat exchange medium from the heat exchange system; or any combination thereof; alternatively, controlling a second level of a liquid phase of the first heat exchange medium on the second heat exchange surface first side; alternatively, adding first heat exchange medium to the heat exchange system or removing a portion of the first heat exchange medium from the heat exchange system; or alternatively, controlling the pressure on the first heat exchange surface second side (and/or first heat exchange medium, and/or second heat exchange surface first side). In an aspect, controlling the pressure on the first heat exchange surface second side (and/or first heat exchange medium, and/or second heat exchange surface first side), which can be utilized to control the first level of the first heat exchange medium on the first heat exchange surface second side or to control the reaction mixture temperature (or average reaction mixture temperature) in the reaction zone can comprise controlling the pressure set point of the one or more pressure control points. In other aspects, controlling the reaction mixture temperature (or average reaction mixture temperature) can comprise increasing or decreasing the flow rate of the first heat exchange medium.

Generally, when controlling the pressure on the first heat exchange surface second side (and/or on the second heat exchange surface first side and/or the first heat exchange medium) to control a reaction mixture temperature (or average reaction mixture temperature) and/or control a first level of liquid phase of the first heat exchange medium, the pressure can be controlled (maintained, adjusted, increased or decreased) to be any pressure less than pressure less than 1 atmosphere (101.3 kPa) as described herein. Generally, when controlling the first level of liquid phase of the first heat exchange medium on the first heat exchange surface second side to control a reaction mixture temperature (or average reaction mixture temperature), the first level of liquid phase of the first heat exchange medium on the first heat exchange surface second side can be controlled to be any first level of liquid phase of the first heat exchange medium on the first heat exchange surface second side as disclosed herein. Generally, when controlling the second level of liquid phase of the first heat exchange medium on the second heat exchange surface first side to control a reaction mixture temperature (or average reaction mixture temperature) and/or control a first level of liquid phase of the first heat exchange medium, the second level of liquid phase of the first heat exchange medium on the second heat exchange surface first side can be controlled to be any second level of liquid phase of the first heat exchange medium on the second heat exchange surface second side as disclosed herein.

FIG. 1 illustrates a portion of a non-limiting reaction system 100, including a heat exchange system 110 and at least a portion of a reaction zone 101. In an aspect, the reaction zone 101 can contain a reaction mixture. In an aspect, the heat exchange system 110 can be utilized to control a reaction mixture temperature (or an average reaction mixture temperature) within reaction zone 101, and/or a pressure in the heat exchange system. The heat exchange system 110 includes the heat exchanger 111 (also referred to herein as first heat exchanger or first heat exchanger 111 for clarity) and process lines 201 and 202. The heat exchange system 110 is discussed in more detail herein. The at least a portion of reaction zone 101 of reaction system 100 is any location in the process and reaction system 100 where all the necessary reaction components (e.g., at least ethylene, a catalyst system or catalyst system components, optionally an organic reaction medium, and optionally hydrogen) and reaction conditions (e.g., process conditions as described herein) are present such that oligomerization reaction can occur at a desired rate. The at least a portion of reaction zone 101 is discussed in more detail herein. One or more reaction zone inlets (not shown) can be included in reaction system 100 to introduce/feed one or more reaction mixture components (e.g., ethylene, catalyst system or catalyst system components, optionally organic reaction medium, optionally hydrogen, or combinations thereof) into the reaction mixture. The one or more reaction zone inlets can be configured to introduce/feed the one or more reaction components into the reaction mixture. One or more reaction zone outlets (not shown) can be included to remove reaction mixture from the reaction zone. The one or more reaction zone outlets are configured to withdraw reaction mixture from the reaction zone. Reaction system 100 and heat exchange system 110 can additionally comprise any equipment associated with reaction systems, such as a vessel, one or more control devices (e.g., a PID controller), measurement instruments (e.g., thermocouples, transducers, and flow meters), alternative inlet lines and outlet lines (all not shown).

The heat exchanger 111 is configured to provide indirect contact between at least a portion of the reaction mixture and a heat exchange medium (also referred to herein as the first heat exchange medium for clarity). Indirect contact refers to contact through a heat conductive material such as the heat exchange surface 112 (also referred to herein as first heat exchange surface or first heat exchange surface 111, for clarity) described herein (e.g., a first heat exchange surface which can be embodied as metal tubes or metal plates), without any direct contact or mixing between the reaction mixture and the heat exchange medium. The heat exchanger 111 comprises heat exchange surface 112 that is configured to separate the reaction mixture from the heat exchange medium inside the heat exchanger 111 and thus provide indirect contact between the heat exchange medium and the reaction mixture. The heat exchange surface 12 separates the heat exchanger 111 into two sections: a first section through which the reaction mixture flows and a second section through which the heat exchange medium flows. In aspects, the heat exchanger 111 comprises a heat exchange surface first side 113 (i.e., first side 113 of the heat exchange surface 112 and also referred to herein as first heat exchange surface first side or first heat exchange surface first side 113, for clarity) configured to contact the reaction mixture and a heat exchange surface second side 114 (i.e., second side 114 of the heat exchange surface 112 and also referred to herein as first heat exchange surface second side or first heat exchange surface second side 114, for clarity) is configured to contact the heat exchange medium. In an aspect, the heat exchange surface 112 can be horizontally oriented, e.g., embodied as horizontally oriented tubes or plates, or vertically oriented, e.g., embodied as vertically oriented tubes or plates; alternatively, horizontally oriented; or alternatively, vertically oriented. In an aspect, the pressure in heat exchanger system 110 that is controlled can be the pressure on the heat exchange surface second side 114 (or on the heat exchange medium).

Heat exchange medium inflow line 201 and heat exchange medium outflow line 202 (representing a plurality of conduits) are connected to the heat exchanger 111. The heat exchange medium can flow into the heat exchanger 111 via inflow line 201 configured to allow for flow of the heat exchange medium into the heat exchanger 111, and through heat exchanger 111, where the heat exchange medium contacts the heat exchange surface second side 114. For an exothermic reaction such as oligomerization reactions, heat is indirectly transferred from the reaction mixture to the heat exchange medium via contact of the reaction mixture with the heat exchange surface first side 113 and by contacting the heat exchange medium with the heat exchange surface second side 114. Flow of the heat exchange medium through the heat exchanger 111 carries heated heat exchange medium out of the heat exchanger via outflow line 202 configured to allow for flow of the heat exchange medium out of the heat exchanger 111.

The direction of flow of the reaction mixture relative to the direction of flow of the heat exchange medium in the heat exchanger 111 can be counter flow, concurrent flow, cross flow, or a combination thereof. In an aspect, the heat exchange surface 112 can include multiple passes where the reaction mixture indirectly contacts the heat exchange medium. In aspects, the heat exchanger 111 can be of a tubular design (e.g., shell and tube heat exchanger), a plate design (e.g., shell and plate heat exchanger), or a combination of tubular and plate design; alternatively, tubular design;

alternatively, a plate design; or alternatively, a combination of tubular and plate design. In any design, the heat exchange surface 112 can be embodied as a tube and/or plate configured to provide the indirect contact between the reaction mixture and the heat exchange medium. It is contemplated that the reaction mixture can flow on the tube side or plate side of the heat exchanger 111 while the heat exchange medium flows on the shell side; alternatively, the reaction mixture can flow on the shell side while the heat exchange medium can flow on the tube side or plate side. The heat exchange medium can comprise a liquid phase of the heat exchange medium, a vapor phase of the heat exchange medium, or liquid phase and vapor phase and vapor phase of the heat exchange medium; alternatively, a liquid phase of the heat exchange medium; alternatively, a vapor phase of the heat exchange medium; or alternatively, liquid and vapor phase of the heat exchange medium. In some aspects, the heat exchange medium can enter heat exchanger 111 (via line 201) as a liquid phase of the heat exchange medium and exit heat exchanger 111 (via 202) as a liquid phase of the heat exchange medium such that the reaction mixture in the reaction zone 101 that is on the heat exchange surface first side 113 indirectly contacts only the liquid phase of the heat exchange medium on the heat exchange surface second side 114. In another aspect, it is contemplated that i) the heat exchange medium remains in liquid phase during indirect contact with the reaction mixture through the heat exchange surface 112 and that ii) the heat exchange medium is in the vapor phase in the space of heat exchanger 111 that is above the heat exchange surface 112 (e.g., such that the vapor phase does not contact the heat exchange surface 112). It is also contemplated that liquid heat exchange medium within the heat exchanger 111 can vaporize through indirect contact with the reaction mixture through heat exchange surface 112. Thus, the heat exchange medium can be present on the heat exchange surface second side 114 in both the liquid phase and the vapor phase. In an aspect, the heat exchange medium can enter heat exchanger 111 (via line 201) as a liquid phase of the heat exchange medium and exit heat exchanger 111 (via 202) as a vapor phase of the heat exchange medium. Thus, a first part of the at least a portion of the reaction mixture in the heat exchanger 111 (or on the heat exchange surface first side 113) indirectly contacts a liquid phase of the heat exchange medium in the heat exchanger 11 (or on the heat exchange surface second side 114) and a second part of the at least a portion of the reaction mixture in the heat exchanger 111 (or on the heat exchange surface first side 113) indirectly contacts a vapor phase of the heat exchange medium in the heat exchanger 111 (or on the heat exchange surface second side 114). In such aspects, there can be level of liquid phase of the heat exchange medium within first heat exchanger 111 (or on the heat exchange surface second side 114).

The heat exchange system 110 can further comprise a level indicator and/or controller 140 configured to measure, monitor, and/or control a level of the liquid phase of the first heat exchange medium in the first heat exchanger 111 (or on the heat exchange surface second side 114). Generally, the level indicator and/or controller 140 is coupled to the heat exchanger 211. In an aspect, the level indicator and/or controller 140 can include 1) one or more pressure drop (DP) cells (fluidly connected to process line 201 and/or fluidly connected to process line 202), not shown, configured to measure the pressure drop across the heat exchange surface second side 114 (also referred to as the pressure drop across the heat exchange surface second side 114 of heat exchanger 111); 2) a pressure sensor (not shown) on the heat exchange medium inlet side of the heat exchanger 111 (e.g., in or fluidly connected to process line 201), a pressure sensor (not shown) on the heat exchange medium outlet side of the heat exchanger 111 (e.g., in or fluidly connected to process line 202), and a device (not shown) to calculate the pressure drop across the heat exchange surface second side 114; and/or 3) a temperature sensor (not shown) on the heat exchange medium inlet side of the heat exchanger 111 (e.g., in process line 201), a temperature sensor (not shown) on the heat exchanger outlet side of the heat exchanger 111 (e.g., in process line 202), and device (not shown) to convert the temperature readings to pressure and calculate the pressure drop across the heat exchange surface second side 114 of heat exchanger 111. The pressure drop across the heat exchange surface second side 114 can be subsequently utilized to determine the equivalent amount of heat exchange medium (or the equivalent height, or a liquid level, of the heat exchange medium) on the heat exchange surface second side 114 at still conditions (i.e., conditions at which there are no bubbles). The pressure drop across the heat exchange surface second side 114 can be utilized to determine the level of liquid phase of heat exchange medium in the heat exchanger 111 (or on the heat exchange surface second side 114). Lines 141 and 142 represent fluid lines to fluidly connect process lines 201 and 202 to level controller 140 and electrical lines or wireless transmitters to transmit pressure and/or temperature readings, to level controller 140. In some aspects, the level indicator and/or controller 140 can be configured to actuate one or more control valves (not shown) to control the flow rate of the heat exchange medium (liquid phase and/or vapor phase) into or out of heat exchanger 11 (e.g., via control valves—not shown—on process lines 201 and/or 202); alternatively, or additionally, the level controller 140 can be configured to actuate one or more control valves (not shown) to control the flow of the reaction mixture (or components for the reaction mixture) into heat exchanger 111 (e.g., via process line 102); additionally or alternatively, the level indicator and/or controller 140 can be configured to actuate one or more heat exchange medium flow control valves to control the first level of liquid phase of the first heat exchange medium on the first heat exchange surface second side 114. In an aspect, level indicator and/or controller 140 can be configured to control the first level of liquid phase of the first heat exchange medium of the first heat exchange surface first side to be a) any percentage of the at least a portion of the reaction mixture on the first heat exchange surface first side which indirectly contacts a liquid phase of the first heat exchange medium on the first heat exchange surface second side disclosed herein, b) any percentage of the surface area of the first heat exchange surface second side which contacts the liquid phase of the first heat exchange medium disclosed herein, c) any volume ratio of the liquid phase of the first heat exchange medium in the first heat exchanger (or on the first heat exchange surface second side) to the vapor phase of the first heat exchange medium in the first heat exchanger (or on the first heat exchange surface second side) disclosed herein, or d) any combination thereof.

Heat exchange system 110 of reaction system 100 in FIG. 1 can further comprise one or more pressure controllers (e.g., pressure controller 130 and a pressure control device 131) in fluid communication with the heat exchange surface second side 114 (e.g. through at least one of the process lines 201 and/or 202 (shown)). The one or more pressure controllers can be configured to measure, monitor, and/or control the pressure of less than 1 atmosphere (101.3 kPa) on the first heat exchange surface second side. The level indicator and/or controller (coupled to the first heat exchanger) is configured to control the first level of liquid phase of the first heat exchange medium of the first heat exchange surface first side to be a) any percentage of the at least a portion of the reaction mixture on the first heat exchange surface first side which indirectly contacts a liquid phase of the first heat exchange medium on the first heat exchange surface second side disclosed herein, b) any percentage of the surface area of the first heat exchange surface second side which contacts the liquid phase of the first heat exchange medium disclosed herein, c) any volume ratio of the liquid phase of the first heat exchange medium in the first heat exchanger (or on the first heat exchange surface second side) to the vapor phase of the first heat exchange medium in the first heat exchanger (or on the first heat exchange surface second side) disclosed herein, or d) any combination thereof. Pressure control device 130 can be fluidly connected to process line 202 by process line 107. In an aspect, the pressure controller 130 and pressure control device 131 (and optionally process line 107) are fluidly connected to the process line 202 and are configured to provide to apply any pressure of less than 1 atmosphere (101.3 kPa) described herein on the first heat exchange surface second side 114 (or on the heat exchange medium). In another aspect, pressure control device 130 and pressure control device 131 (and optionally process line 107) can be utilized to 1) control the pressure on the heat exchange surface second side 114 (or on the heat exchange medium), 2) control the level of liquid phase of the heat exchange medium on the heat exchange surface second side, 3) control the reaction mixture temperature (or average reaction mixture temperature) on the heat exchange surface first side, 4) any combination thereof. Pressure control device 131 can include a pressure sensor (not shown) in, or fluidly connected to, process line 202 (or process line 201) and configured to 1) receive pressure measurement signals from the pressure sensor and 2) perform control logic to allow pressure control device 130 to control the pressure on the heat exchange surface second side 114 (or on the heat exchange medium);

Reaction system 100 in FIG. 1 can further comprise a temperature indicator and/or controller (not shown) configured to measure and/or control the reaction mixture temperature (or average reaction mixture temperature) within the reaction zone 101. In an aspect, the temperature indicator and the temperature controller functions can be contained in a single device or in separate devices; alternatively, a single device, or alternatively, in separate devices. In an aspect, the temperature indicator and/or controller can be a) coupled to at least one of the pressure control devices (e.g., pressure controller 130 and a pressure control device 131) and configured to actuate a control mechanism to control a pressure set point of the at least one of the one or more pressure control devices, b) coupled with the level indicator or controller 140 and configured to control the level of liquid phase of the heat exchange medium in the first heat exchanger (or on the heat exchange surface second side, c) coupled to the heat exchange medium flow control valve (not shown) and configured to actuate a heat exchange medium flow control valve to control the flow rate of liquid phase of the first heat exchange medium into the first heat exchange surface second side, or d) a combination thereof, in response to the reaction mixture temperature (or average reaction mixture temperature).

The temperature of the reaction mixture within the reaction zone 101 is controlled (maintained, increased, or decreased) according to the techniques disclosed herein. In aspects, the temperature and/or pressure of the heat exchange system (e.g., the heat exchange medium, the heat exchanger 111 in FIG. 1, and optionally any combination of other heat exchange components discussed for FIG. 2 or 3) can be controlled to provide any reaction mixture temperature (or average reaction mixture temperature) in the reaction zone 101 as described. Control of the temperature and pressure of the heat exchange system are described in more detail herein.

The reaction mixture temperature (or average reaction mixture temperature) within the reaction zone 101 of the reaction process and reaction system 100 can be controlled (maintained, increased or decreased) by continuously or intermittently introducing the heat exchange medium into the heat exchanger 111 via line 201 and continuously or intermittently removing the heat exchange medium from the heat exchanger 111 via line 202, while the reaction mixture contacts the first heat exchange surface first side 113 and passes through the heat exchanger 111. The techniques contemplated by the disclosure for controlling the temperature of the reaction mixture are described in more detail herein. Generally, the transfer of heat within the heat exchanger 111 occurs because heat transfers through the heat exchange surface 112 from the reaction mixture into the heat exchange medium, or vice versa. In aspects where heat transfers from the reaction mixture to the heat exchange medium via the heat exchange surface 112 (e.g., during the exothermic oligomerization reactions), the reaction mixture is cooled by transferring heat to the heat exchange surface 112 and the heat exchange medium is heated warmed by transferring heat from the heat exchange surface 112. In aspects where heat transfers from the heat exchange medium to the reaction mixture via the heat exchange surface 112, the heat exchange medium is cooled by transferring heat to the heat exchange surface 112 and the reaction mixture is warmed by transferring heat from the heat exchange surface 112. Consequently, the heat exchanger and heat exchange medium maintain a desired temperature by cooling the portions of the reaction mixture that are hotter than the heat exchange medium and/or heating the portions of the reaction mixture which are cooler than the heat exchange medium. Additionally, the heat exchange can be utilized to increase or decrease the desired reaction temperature by changing the temperature of the heat exchange medium within the heat exchanger (e.g., via controlling the pressure on the first heat exchange surface second side 114).

Figure 2:
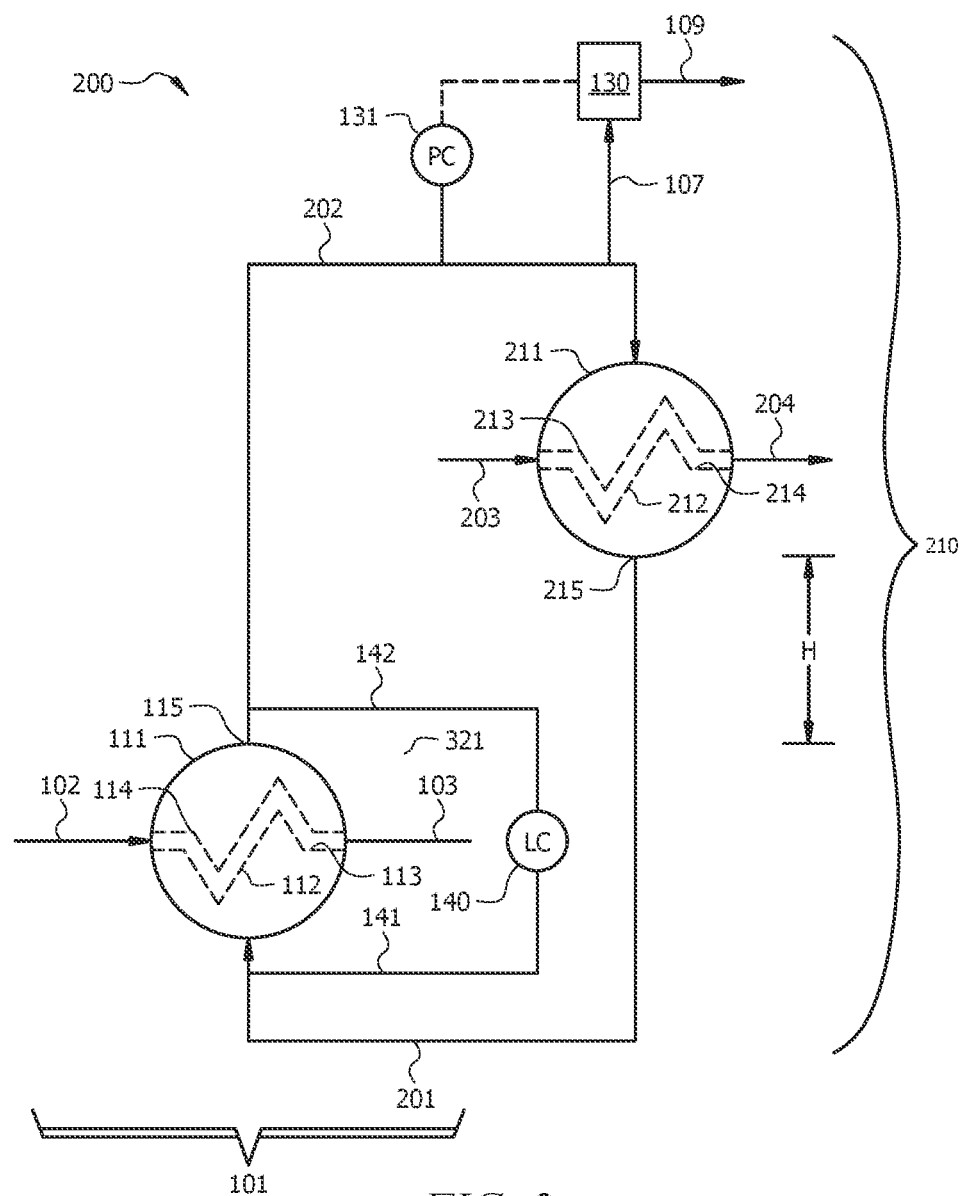
FIG. 2 illustrates another process and reaction system for controlling a temperature of a reaction mixture within an oligomerization reaction zone.

FIG. 2 illustrates a portion of another non-limiting reaction system, reaction system 200, including a heat exchange system 210 and at least a portion of reaction zone 101. In an aspect, heat exchange system 210 can be utilized to control a reaction mixture temperature (or an average reaction mixture temperature) within reaction zone 101 and/or a pressure in the heat exchange system. The reaction system 200 of FIG. 2 is similar to reaction system 100 of FIG. 1, wherein like numbers represent like components described in relation to FIG. 1 and their descriptions and/or functions can be utilized to further describe reaction system 200 and/or heat exchange system 210 without limitation unless explicitly indicated. The heat exchange system 210 in FIG. 2 differs from the heat exchange system 110 in FIG. 1 in that heat exchange system 210 includes a second heat exchanger 211 and process lines 203 and 204. Additionally, heat exchange system 210 in FIG. 2 differs from the heat exchange system 110 in FIG. 1 in that the heat exchange medium is circulated in a heat exchange medium loop including heat exchanger 111 and second heat exchanger 211. The unique aspects of reaction system 200 and heat exchange system 210 are discussed in more detail herein.

Reaction system 200 and heat exchange system 210 can additionally comprise any equipment associated with reaction systems, such as a vessel, one or more control devices (e.g., a PID controller), measurement instruments (e.g., thermocouples, transducers, and flow meters), alternative inlet lines, and outlet lines (all not shown).

The second heat exchanger 211 is configured to provide indirect contact between the heat exchange medium discussed for FIG. 1 and a second heat exchange medium. Indirect contact refers to contact through a heat conductive material such as the second heat exchange surface 212 described herein (e.g., a second heat exchange surface which can be embodied as such as metal tubes or metal plates), without any direct contact or mixing between the two heat exchange mediums. The second heat exchanger 211 comprises second heat exchange surface 212 (distinct from the heat exchange surface 112) that is configured to separate the first heat exchange medium from the second heat exchange medium inside the heat exchanger 211 and thus provide indirect contact between the two heat exchange mediums. Heat exchange surface 212 thus separates the heat exchanger 211 into two sections: a first section through which the first heat exchange medium flows and a second section through which the second heat exchange medium flows. In aspects, the second heat exchanger 211 comprises a second heat exchange surface first side 213 (i.e., first side 213 of the second heat exchange surface 212) configured to contact the first heat exchange medium and a second heat exchange surface second side 214 (i.e., second side of the second heat exchange surface 212) configured to contact the second heat exchange medium. In an aspect, a pressure on the second heat exchange surface first side 213 can be any pressure less than 1 atmosphere (101.3 kPa) as disclosed herein. In an aspect, the second heat exchange surface does not contact the reaction mixture. In an aspect, the second heat exchange surface 212 can be horizontally oriented, e.g., embodied as horizontally oriented tubes or plates, or vertically oriented, e.g., embodied as vertically oriented tubes or plates; alternatively, horizontally oriented; or alternatively, vertically oriented. In an aspect, the pressure in the heat exchange system 210 that is controlled can be the pressure on the first heat exchange surface first side 113 and the pressure on the second heat exchange surface second side 214 (or on the first heat exchange medium).

The second heat exchange medium inflow line 203 and the second heat exchange medium outflow line 204 are connected to the second heat exchanger 211. The second heat exchange medium can flow into the second heat exchanger 211 via inflow line 203 configured to allow for flow of the second heat exchange medium into heat exchange 211, and through second heat exchanger 211 where the second heat exchange medium contacts the second heat exchange surface second side 214. Heat is indirectly transferred from the first heat exchange medium to the second heat exchange medium via contact of first heat exchange medium with the second heat exchange surface first side 213 and by contacting the second heat exchange medium with the second heat exchange surface second side 214. Flow of the second heat exchange medium through the second heat exchanger 211 carries heated second heat exchange medium out of the second heat exchanger via outflow line 204 configured to allow for flow of the second heat exchange medium out of second heat exchanger 211.

The direction of flow of the first heat exchange medium relative to the direction of flow of the second heat exchange medium in the second heat exchanger 211 can be counter flow, concurrent flow, cross flow, or a combination thereof.

In an aspect, the second heat exchange surface 212 can include multiple passes where the first heat exchange medium indirectly contacts the second heat exchange medium. In aspects, the second heat exchanger 211 can be of a tubular design (e.g., shell and tube heat exchanger), a plate design (e.g., shell and plate heat exchanger), or a combination of tubular and plate design; alternatively, tubular design; alternatively, a plate design; or alternatively, a combination of tubular and plate design. In any design, the second heat exchange surface 212 can be embodied as a tube and/or plate configured to provide the indirect contact between the first heat exchange medium and the second heat exchange medium. It is contemplated that the first heat exchange medium can flow on the tube side or plate side of the second heat exchanger 211 while the second heat exchange medium flows on the shell side; alternatively, the first heat exchange medium can flow on the shell side while the second heat exchange medium can flow on the tube side or plate side.

The second heat exchanger 211 of the heat exchange system 210 is fluidly connected to the first heat exchanger 111 by a plurality of conduits (e.g., process line 201 and process line 202). In FIG. 2, process lines 201 and 202 each represent a conduit of the plurality of conduits and are configured to fluidly connect the first heat exchanger 111 and the second heat exchanger 112 and configured to allow for flow of the first heat exchange medium between the first heat exchange surface second side 114 and the second heat exchange surface first side 113. The plurality of conduits (e.g., process lines 201 and 202), the first heat exchanger 111, and the second heat exchanger 211 are configured to fluidly connect the first heat exchanger and the second heat exchanger to form a first heat exchange medium circulation loop circulation loop. In the circulation loop, the first heat exchange medium can flow between the heat exchange surface second side 114 and the second heat exchange surface first side 213. In an aspect, at least one of one or more conduits (e.g., process line 202) allows for flow of the first heat exchange medium from the heat exchange surface second side 114 (also referred to herein as the first heat exchange surface second side 114 for clarity) to the second heat exchange surface first side 213, and at least one of the one or more conduits (e.g., process line 201) allows for flow of the first heat exchange medium from the second heat exchange surface first side 213 to the first heat exchange surface second side 114.

In aspects where the heat exchange system contains both liquid phase and vapor phase of the first heat exchange medium, the heat exchange system 210 can be configured such that the vapor phase of the first heat exchange medium condenses to liquid phase first heat exchange medium in the second heat exchanger 211. In an aspect, the first heat exchange medium enters the second heat exchanger 211 through line 202 as vapor phase, and the first heat exchange medium contacts the second heat exchange surface first side 213, and ultimately condenses into liquid phase first heat exchange medium. Thus, vapor phase and liquid phase of the first heat exchange medium can contact the second heat exchange surface first side 213. As such, at least a first part of the second heat exchange medium on the second heat exchange surface second side 214 (or a first part of the surface area of the second heat exchange surface first side) indirectly contacts the vapor phase of the first heat exchange medium on the second heat exchange surface first side 213 and a second part of the second heat exchange medium on the second heat exchange surface second side 214 indirectly contacts liquid phase of the first heat exchange medium on the second heat exchange surface first side 213. Thus, there is provided a second level of first heat exchange medium on the second heat exchange surface first side. In an aspect, at least one of the plurality of conduits (e.g., process line 202) allows for flow of the vapor phase of the first heat exchange medium from the first heat exchanger (or the first heat exchange surface second side 114) to the second heat exchanger (or second heat exchange surface first side 213), and at least one of the plurality of conduits (e.g., process line 201) allows for flow of the liquid phase of first heat exchanger medium from the second heat exchanger (or the second heat exchange surface first side 213) to the first heat exchange (or the first heat exchange surface second side 114).

In an aspect, vapor phase and liquid phase of the first heat exchange medium can be present in the second heat exchanger 211 (or on/contacting the second heat exchange surface first side 213). In such aspects, there can be level of liquid phase of the heat exchange medium within second heat exchanger 211 (or on/contacting the second heat exchange surface first side 213). The level of liquid phase of the heat exchange medium within first heat exchanger 211 (or on/contacting the second heat exchange surface first side 213) can also be referred to herein as a second level of liquid phase of the first heat exchange medium for clarity to distinguish it from the level of liquid phase of the first heat exchange medium on the first heat exchange surface second side 114, which can also be referred to herein as the first level of the liquid phase of the first heat exchange medium. The second level of liquid phase of the first heat exchange medium can be i) any percentage of the second heat exchange medium on the second heat exchange surface second side 214 which indirectly contacts the liquid phase of the first heat exchange medium on the second heat exchange surface first side 213 disclosed herein, ii) any volume ratio of the liquid phase of the first heat exchange medium in the second heat exchanger 211 (or on the second heat exchange surface first side 213) to the vapor phase of the first heat exchange medium in the second heat exchanger 211 (or on the second heat exchange surface first side 213) disclosed herein, or iii) any combination thereof. The disclosure contemplates monitoring and/or controlling the second level of the liquid phase of the first heat exchange medium in the second heat exchanger 211 (or on/contacting the second heat exchange surface first side 213). In some aspects, the second level of the liquid phase of the first heat exchange medium on the second heat exchange surface first side 213 can be utilized to control pressure on the first heat exchange surface second side 114 (or on the second heat exchange surface first side 213 or on the first heat exchange medium) and/or control the reaction mixture temperature (or the average reaction mixture temperature). Techniques for controlling the second level of liquid phase of the first heat exchange medium in the second heat exchanger (or on/contacting the second heat exchange surface first side 213) are described in more detail herein. In an aspect, the first heat exchange medium on the second heat exchange surface first side 213 can be on the shell side of the second heat exchanger 211, or on the tube or plate side of the second heat exchanger 211; alternatively, on the shell side of the second heat exchanger 211; or alternatively, on the tube or plate side of the second heat exchanger 211.

As in FIG. 1, the heat exchange system 210 of reaction system 200 depicted in FIG. 2 can further comprise one or more pressure controllers (e.g., pressure controller 130 and pressure control device 131) and can have the general features (e.g., a pressure sensor, not shown, among other features) and/or functions (e.g., receive pressure measurement signals and/or control a pressure, among other functions) of the one or more pressure controllers as disclosed for FIG. 1. The one or more pressure controllers depicted in FIG. 2 differ from the one or more pressure controllers in FIG. 1 in the aspect that the one or more pressure controllers can be in fluid communication with the first heat exchange surface second side 114 and/or the second heat exchange surface first side 213. In an aspect, the one or more pressure controllers (e.g., pressure controller 130 and a pressure control device 131) can be in direct fluid communication with at least one of the plurality of conduits (e.g., process line 201 or 202), for example via process line 107. In one aspect, the one or more pressure controllers (e.g., pressure controller 130 and a pressure control device 131) can be in direct fluid communication with at least one of the plurality of conduits allowing for flow of the first heat exchange medium from the first heat exchange surface second side 114 to the second heat exchange surface first side 213 (e.g. process line 202), for example via process line 107. In another aspect, the one or more pressure controllers (e.g., pressure controller 130 and a pressure control device 131) can be in direct fluid communication with at least one of the plurality of conduits allowing for flow of the vapor phase of the first heat exchange medium from the first heat exchange surface second side 114 to the second heat exchange surface first side 213 (e.g. process line 202), for example via process line 107. The one or more pressure controllers (e.g., pressure controller 130 and a pressure control device 131) can be configured to measure, provide, and/or control the pressure on the first heat exchange surface second side 114 and/or the second heat exchange surface first side 213. Generally, the one or more pressure controllers (e.g., pressure controller 130 and a pressure control device 131) can provide, and/or control, the pressure to be any pressure less than 1 atmosphere (101.3 kPa) disclosed herein. Additionally, the one or more pressure controllers of FIG. 2 (e.g., pressure controller 130 and a pressure control device 131) can differ from the one or more pressure controllers of FIG. 1 in that at least one of the one or more controllers of FIG. 2 can have an outlet line (e.g., outlet line 109). In an aspect, outlet line 109 can assist in allowing the one or more pressure controllers to provide, and/or control the pressure on the first heat exchange surface second side 114 and/or the second heat exchange surface first side 213 (and/or the first heat exchange medium). In another combinable aspect, at least one of the one or more pressure controllers can include a sensor (not shown) and/or a control valve (not shown) within the pressure controller or outline line 109. In an aspect, the sensor can be configured to actuate the control valve between an open position and a closed position to 1) control the pressure on the first heat exchange surface second side 114 and/or the second heat exchange surface first side 213, and/or 2) allow non-condensable components in the first heat exchange medium to be removed from the first heat exchange medium (or from the first heat exchange medium circulation loop).

As in FIG. 1, the heat exchange system 210 of reaction system 200 depicted in FIG. 2 can further comprise a level indicator and/or controller 140 configured to measure, monitor, and/or control a level of the liquid phase of the first heat exchange medium in the first heat exchanger 111 (or on the heat exchange surface second side 114) and can have the general features (e.g., pressure drop cells, pressure sensors, and associated devices) to calculate pressure drop across the heat exchange surface second side 114. And/or the system 210 can further comprise a temperature sensor and device (not shown) to convert the temperature readings to pressure and calculate the pressure drop across the heat exchange surface second side 114 of heat exchanger 111, among other features and/or functions (e.g., control the flow of the reaction mixture (or reaction mixture components) into heat exchanger 111 and/or control the level of liquid phase of the first heat exchange medium on the first heat exchange surface second side 114, among other functions) of level indicator and/or controller 140 as disclosed for FIG. 1.

Reaction system 200 in FIG. 2, similar to FIG. 1, can further comprise a temperature indicator and/or controller (not shown) configured to measure and/or control the reaction mixture temperature (or average reaction mixture temperature) within the reaction zone 101. In an aspect, the temperature indicator and/or controller can be a) coupled to at least one of the pressure control devices (e.g., pressure controller 130 and a pressure control device 131) and configured to actuate a control mechanism to control a pressure set point of the at least one of the one or more pressure control devices, b) coupled with the first level indicator or controller 140 and configured to control the level of liquid phase of the heat exchange medium in the first heat exchanger (or on the heat exchange surface second side, or c) a combination thereof, in response to the reaction mixture temperature (or average reaction mixture temperature).

In an aspect, the second heat exchanger 211 can be vertically higher relative to a common reference point 221 (not shown) on the ground 220 (not shown) than the first heat exchanger 111. Generally, vertically higher can be a vertical distance H. The minimum distance H can be 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 meters; or additionally, a maximum of 15, 12, 10, 8, 7, 6, 5, 4, 3, 2, or 1 meter. In an aspect, the distance H can range from any minimum value disclosed herein to any maximum value disclosed herein. Non-limiting suitable ranges for the distance H can include from 0.05 meters to 15 meters, 0.1 meters to 10 meters, 0.1 meters to 5 meters, 0.2 meters to 10 meter, 0.2 meters to 5 meters, 0.2 meters to 2 meters, 0.3 meters to 5 meters, 0.3 meters to 2 meters, 0.5 meters to 5 meters, 0.5 meters to 2 meters, 0.7 meters to 10 meters, 0.7 meters to 5 meters, and 1 meter to 5 meters. Other appropriate distances H are readily apparent from this disclosure. In one aspect, vertically higher relative to a common point of reference can mean the bottom 215 of the second heat exchanger 211 can be vertically higher than the top 115 of the first heat exchanger 111. In another aspect, vertically higher relative to a common reference point on the ground can mean that the second level of the liquid phase of the first heat exchange medium in the first heat exchanger 211 (or on/contacting the second heat exchange surface first side 213) is vertically higher relative to a common reference point on the ground than the first level of the liquid phase of the first heat medium in the first heat exchanger (or on/contacting the first heat exchange surface second side 114). Without being limited by theory, it is believed that having a vertical distance, H, between the bottom 215 of the second heat exchanger 211 and the top 115 of the first heat exchanger 111, or between the first level of liquid phase of the first heat exchange medium and the second level of liquid phase of the first heat exchange medium, can be advantageous in controlling the pressure on the first heat exchange surface second side 14 and/or on second heat exchange surface first side 213 (and/or on the first heat exchange medium).

Figure 3:
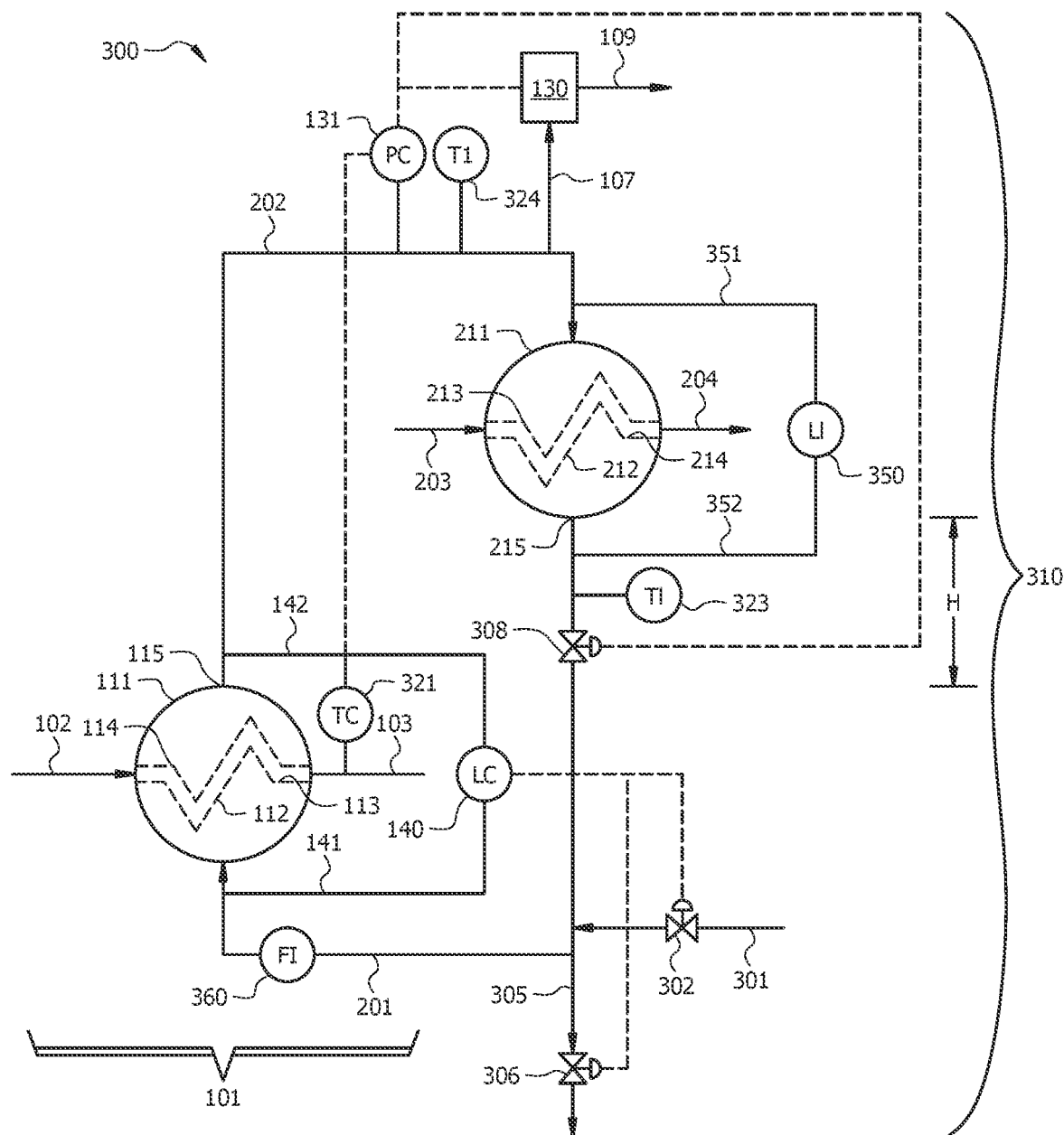
FIG. 3 illustrates another process and reaction system for controlling a temperature of a reaction mixture within an oligomerization reaction zone.

FIG. 3 illustrates a portion of another non-limiting reaction system, reaction system 300, including a heat exchange system 310, and at least a portion of reaction zone 101. In an aspect, heat exchange system 310 can be utilized to control a reaction mixture temperature (or an average reaction mixture temperature) within reaction zone 101, and/or a pressure in the heat exchange system. Reaction system 300 of FIG. 3 is similar to reaction system 100 of FIG. 1 and reaction system 200 of FIG. 2, wherein like numbers represent like components described in relation to FIG. 1 and/or FIG. 2 and their descriptions and functions can be utilized to further describe reaction system 300 and/or heat exchange system 310 without limitation unless explicitly indicated. The heat exchange system 310 in FIG. 3 differs from the heat exchange system 210 in FIG. 2 in that heat exchange system 310 includes various equipment and streams for 1) monitoring and/or controlling a reaction mixture temperature (or average reaction mixture temperature) in the reaction zone 101, a pressure in the heat exchange system 310 (or on the first heat exchange medium), and amount of the first heat exchange medium in the heat exchange system 310. Similar to heat exchange system 210 of FIG. 2, heat exchange system 310 in FIG. 3 includes the first heat exchanger 111, process lines 201 and 202, the second heat exchanger 211, and process lines 203 and 204, level controller 140 and associate process lines 142 and 141, pressure controller 130, pressure control device 131, and associated process lines 107 and 109, among other equipment and process lines disclosed for heat exchange system 210. Similar to the heat exchange system 210 described for FIG. 2, the first heat exchange medium in heat exchange system 310 in FIG. 3 is circulated in a heat exchange medium loop including the first heat exchanger 111, process lines 201 and 201, and the second heat exchanger 211. Reaction system 300 and heat exchange system 310 in FIG. 3 depict further equipment for 1) monitoring and/or controlling a reaction mixture (or average reaction mixture) temperature, 2) monitoring and/or controlling a temperature (or average temperature) of the first heat exchange medium throughout heat exchange system 310, 3) monitoring and/or controlling a pressure on the first heat exchange surface second side 114 (or on the second heat exchange surface first side 213 and/or the first heat exchange medium), and/or 4) adding first heat exchange medium to, or removing first heat exchange medium from, the first heat exchange medium circulation loop, or 5) any combination thereof. The unique aspects of reaction system 300 and heat exchange system 310 are discussed in more detail herein. Reaction system 300 and heat exchange system 310 can additionally comprise any equipment associated with reaction systems, such as a vessel, one or more control devices (e.g., a PID controller), measurement instruments (e.g., thermocouples, transducers, and flow meters), alternative inlet lines, and outlet lines (all not shown). As can be seen in FIG. 3, the heat exchange system 310 can differ from heat exchange system 210 in that heat exchange system can further comprise a first heat exchange medium inlet line 301 and a first heat exchange medium outlet line 305. The first heat exchange medium inlet and outlet lines are fluidly connected at least one of the plurality of conduits of the first heat exchange medium circulation loop. In an aspect, the first heat exchange medium inlet and outlet lines are fluidly connected to the at least one of the plurality of inlets allowing for flow of the first heat exchange medium from the second heat exchanger 211 (or from the second heat exchange surface first side 213) to the first heat exchanger 111 (or the first heat exchange surface second side 114 (e.g., process line 201). The first heat exchange medium inlet line 301 can be configured to introduce first heat exchange medium into the first heat exchange medium circulation loop (e.g., via process line 201) while the first heat exchange medium outlet 305 can be configured to remove a portion of the first heat exchange medium from the first heat exchange medium circulation loop (e.g., via process line 201). Heat exchange system 311 can further comprise a first control valve 302 located on the first heat exchange fluid inlet line 301 and a second control valve 306 located on the first heat exchange medium outlet line 305. The first control valve 302 can be configured to control (allow or disallow) the addition of first heat exchange medium to the first heat exchange medium circulation loop (e.g., via process line 201) while the second control valve is configured to control (allow or disallow) the removal of first heat exchange medium from the first heat exchange medium circulation loop (e.g., via process line 201). In an aspect, first heat exchange medium added to the first heat exchange medium circulation loop via first heat exchange fluid inlet line 301 can be in the liquid phase or vapor phase; alternatively, liquid phase; or alternatively, vapor phase. While FIG. 3 depicts outlet line 305 at a location between the first inlet line 301 and the first heat exchanger 111 (or the first heat exchange surface second side 114), it is contemplated that the outlet line 301 can be located at any position between the first heat exchanger 111 (or the first heat exchange surface second side 114) and second heat exchanger 211 (or the second heat exchange surface first side 213) on the process line 201 allowing for flow of the first heat exchange medium from the second heat exchanger 211 (or form the second heat exchange surface first side 213) to the first heat exchanger 111 (or to the first heat exchange surface second side 114). Thus first heat exchange medium outlet line can be located at a position between the second heat exchanger 211 (or the second heat exchange surface first side 213) and the first heat exchange medium inlet line 301 on the process line 201 allowing for flow of the first heat exchange medium from the second heat exchanger 211 (or form the second heat exchange surface first side 213) to the first heat exchanger 111 (or to the first heat exchange surface second side 114). While FIG. 3 depicts only one inlet line and outlet line with their corresponding control values, it is contemplated that there can be more than one inlet valve for introducing first heat exchange medium to the first heat exchange medium circulation loop and/or more than one outlet line for removing heat exchange medium from the first heat exchange medium circulation loop. Thus, additional first heat exchange medium inlet and outlet lines can be accordingly added to achieve a particular reaction system and/or heat exchange system purpose. These additional first heat exchange medium inlet lines and/or outlet lines can each have their own independent control values.

The first control valve 302 and the second control valve 306 can be coupled to the level indicator 140 (also referred to herein as first level indicator and/or controller 140 to differentiate it from second level controller indicator and/or controller 350). In an aspect, the first level indicator and/or controller 140 can be configured to (a) actuate the first control valve 302 to an open position to add first heat exchange medium to the heat exchange system (or the first heat exchange medium circulation loop), and/or (b) actuate the second control valve 306 to an open position to remove a portion of the first heat exchange medium from the first heat exchange medium circulation. Signals from level controller 140 and/or control logic can be utilized to actuate control valve 302 and/or control value 306 to allow or disallow flow of liquid phase of the first heat exchange medium into or out of the circulation loop to provide and/or control (maintain, adjust, increase and/or decrease) the desired first level of liquid phase or the first heat exchange medium on the first heat exchange surface second side 114. The actuation of the first control valve 302 and/or the second control valve 306 can be performed so as to provide and/or control a desired first level of liquid phase of the heat exchange medium within first heat exchanger 211 (or on the first heat exchange surface second side 114). The actuation of the first control valve can be utilized in increase the first level of liquid phase of the first heat exchange medium in the first heat exchanger 111 (or on the first heat exchange surface second side 114). The actuation of the second control valve can be utilized to decrease the first level of liquid phase of the first heat exchange medium in the first heat exchanger 111 (or on the first heat exchange surface second side 114). The desired first level of liquid phase of the first heat exchange medium can be any value of the first level of liquid phase of the first heat exchange medium disclosed herein as provided in any terms of first level of liquid first heat exchange medium as disclosed herein. The control valves of any additional first heat exchange medium inlet lines and/or outlet lines can also be coupled to, and/or actuated by, the first level indicator and/or controller 140.

In an aspect, the heat exchange system can include a separate vapor phase of the first heat exchange medium inlet line (not shown) fluidly connected to at least one of the plurality of conduits of the first heat exchange medium circulation loop. In an aspect, the vapor phase of the first heat exchange medium inlet (not shown) can be fluidly connected to the at least one of the plurality of inlets allowing for flow of the first heat exchange medium from the second heat exchange 211 (or from the second heat exchange surface first side 213) to the first heat exchanger 111 (or the first heat exchange surface second side 114 (e.g., process line 201). The heat exchange system can further include a control valve (not shown) located on the vapor phase of the first heat exchange fluid inlet line and configured to actuate between an open position and a closed position so as to allow or disallow a flow of vapor phase of the first heat exchange medium into the first heat exchange medium circulation loop. In an aspect, the introduction of vapor phase of the first heat exchange medium into the first heat exchange medium circulation loop can be utilized to heat up the first heat exchange medium circulation loop prior to initiation the olefin oligomerization and/or to increase the temperature of the first heat exchange medium entering the first heat exchanger 111 (or contacting the first heat exchange surface second side 114).

As seen in FIG. 3, heat exchange system 310 can differ from heat exchange system 210 in that heat exchange system 310 can further comprise a second level indicator and/or controller 350. Generally, the second level indicator and/or controller 350 is coupled to the second heat exchanger 211. In an aspect, the level controller 350 can include 1) one or more pressure drop (DP) cells (fluidly connected to process line 202 and/or fluidly connected to process line 201) measuring the pressure drop across the second heat exchange medium surface first side 213 (also referred to as the pressure drop across the second heat exchange surface first side 213), 2) a pressure sensor on the heat exchange medium inlet side of the heat exchanger 211 (e.g., in or fluidly connected to process line 202), a pressure sensor on the heat exchange medium outlet side of the heat exchanger 211 (e.g., in or fluidly connected to process line 201), and a device to calculate the pressure drop across the second heat exchange surface first side 213, and/or 3) a temperature sensor on the heat exchange medium inlet side of the heat exchanger 211 (e.g., in process line 202), a temperature sensor on the heat exchanger outlet side of the heat exchanger 211 (e.g., in process line 201), and device to convert the temperature readings to pressure and calculate the pressure drop across the second heat exchange surface first side 213. The pressure drop across the second heat exchange surface first side 213 can be subsequently utilized to determine the equivalent amount of heat exchange medium (or the equivalent height, or a liquid level, of heat exchange medium) on the second heat exchange surface first side 213 at still conditions (i.e., conditions at which there are no bubbles). The pressure drop across the second heat exchange surface first side 213 can be utilized to determine the second level of liquid phase of heat exchange medium in the heat exchanger 211 (or on the second heat exchange surface first side 213). Lines 351 and 352 represent fluid lines to fluidly connect process lines 201 and 202 to level controller 350, or electrical lines or wireless transmitters to transmit pressure and/or temperature readings, to level controller 350. In an aspect, second level indicator and/or controller 350 can be configured to measure, monitor, and/or control (maintain, adjust, increase, decrease) the second level of the first heat exchange medium in the second heat exchanger 211 (or on the second heat exchange surface first side 213). In an aspect, the second level indicator and/or controller 350 can be configured to control the second level of liquid phase of the first heat exchange medium of the second heat exchange surface first side to be i) any percentage of the second heat exchange medium on the second heat exchange surface second side 214 which indirectly contacts the liquid phase of the first heat exchange medium on the second heat exchange surface first side 213 disclosed herein, ii) any volume ratio of the liquid phase of the first heat exchange medium in the second heat exchanger 211 (or on the second heat exchange surface first side 213) to the vapor phase of the first heat exchange medium in the second heat exchanger 211 (or on the second heat exchange surface first side 213) disclosed herein, or iii) any combination thereof.

Heat exchange system 310, in comparison to heat exchange system 210, can further comprise an optional temperature indicator and/or controller 323. In an aspect, the temperature indicator and the temperature controller functions of temperature indicator and/or controller 323 can be contained in a single device or in separate devices; alternatively, a single device, or alternatively, in separate devices. In an aspect, optional temperature indicator 323 can be can be fluidly connected to, or located within, at least one of the plurality of conduits allowing for flow of liquid phase of the first heat exchange medium from the second heat exchanger 211 (or from the second heat exchange surface first side 213) to the first heat exchanger 111 (or the first heat exchange surface second side 114, e.g., process line 201. Optional temperature indicator 323 can be configured to measure and/or display/transmit the heat exchange medium temperature in process line 201. In an aspect optional temperature indicator 323 can be configured to control the second level of liquid phase of the first heat exchange medium in the second heat exchanger 211 (or on the second heat exchange surface first side 213), the first level of liquid phase of the first heat exchange medium in the first heat exchanger (or on the first heat exchange surface second side 114), and/or the pressure on the first heat exchange surface second side 114 (and/or second heat exchange surface first side 213, and/or first heat exchange medium).

Heat exchange system 310, in comparison to heat exchange system 210, can further comprise a liquid control valve 308. Liquid control valve 308 can be located on at least one of the plurality of conduits allowing for flow of the first heat exchange medium from the second heat exchanger 211 (or from the second heat exchange surface first side 213) to the first heat exchanger 111 (or the first heat exchange surface second side 114). Liquid control valve 308 can be configured to control a second level of the liquid phase of the first heat exchange medium in the second heat exchanger 211 (or on the second heat exchange surface first side 213). In an aspect, liquid control valve 308 can be configured to control the second level of liquid phase of the first heat exchange medium in the second heat exchanger 211 (or on the second heat exchange surface first side 213), the first level of liquid phase of the first heat exchange medium in the first heat exchanger (or on the first heat exchange surface second side 114), and/or the pressure on the first heat exchange surface second side 114 (and/or second heat exchange surface first side 213, and/or first heat exchange medium).

Level controller 350 and/or the optional temperature indicator and/or controller 323 can be utilized to control the second level of the liquid phase of the first heat exchange medium in the second heat exchanger 211 (or on the second heat exchange surface first side 213). Thus, in an aspect, level controller 350 and/or the optional temperature indicator and/or controller 323 can be coupled to 1) the liquid control valve 308 and configured to actuate liquid control vale 308 to control the flow of the second heat exchange medium from the second heat exchanger 211 (or on the second heat exchange surface first side 213) to the first heat exchanger 111 (or the first heat exchange surface second side 214), 2) a second heat exchange medium flow valve (located on second heat exchange inlet line 203 (not shown) or second heat exchange outlet line 204 (not shown)) configured to actuate the second heat exchange medium flow control valve (not shown) to control the flow rate of the second heat exchange medium into (or out of) the second heat exchanger 211 (contact with the second heat exchange surface second side 214), or 3) any combination thereof.

It can be noted that, in the absence of other controls (e.g., adding or removing first heat exchange medium into the first heat exchange medium circulation loop as described herein, among other controls), decreasing the second level of liquid phase of the first heat exchange medium in the second heat exchanger 211 (or on the second heat exchange surface first side 213) increases the first level of liquid phase of the first heat exchange medium in the first heat exchanger (or on the first heat exchange surface second side 114) while increasing the second level of liquid phase of the first heat exchange medium in the second heat exchanger 211 (or on the second heat exchange surface first side 213) decreases the first level of liquid phase of the first heat exchange medium in the first heat exchanger (or on the first heat exchange surface second side 114). Similarly, in the absence of other controls (e.g., adding or removing first heat exchange medium into the first heat exchange medium circulation loop as described herein, among other controls), decreasing the second level of liquid phase of the first heat exchange medium in the second heat exchanger 211 (or on the second heat exchange surface first side 213) decreases the pressure on the first heat exchange surface second side 114 (and/or second heat exchange surface first side 213, and/or first heat exchange medium) while the increasing the second level of liquid phase of the first heat exchange medium in the second heat exchanger 211 (or on the second heat exchange surface first side 213) increases the pressure on the first heat exchange surface second side 114 (and/or second heat exchange surface first side 213, and/or first heat exchange medium). Thus, control mechanisms which control the first level of liquid phase of the first heat exchange medium in the first heat exchanger (or on the first heat exchange surface second side 114) and/or the second level of liquid phase of the first heat exchange medium in the second heat exchanger 211 (or on the second heat exchange surface first side 213) can also be utilized to control the pressure on the first heat exchange surface second side 114 (and/or second heat exchange surface first side 213, and/or first heat exchange medium).

The heat exchange system 310 can also include a flow indicator 360 located on or fluidly connected to the process line 201. The flow indicator 360 can include a flow meter and a display that indicates the flow rate of the first heat exchange medium that is measured by the flow meter in process line 201. In an aspect, the measurements from flow indicator 360 in combination with other measurements, (e.g., first heat exchange medium temperatures measurements reported by temperature indicators and/or controllers located on the first heat exchange medium circulation loop) can be utilized to determine how much heat is generated by the reaction mixture and/or determine the amount of ethylene reacted (i.e., ethylene conversion) in the reaction zone. The flow meter can be any flow meter suitable for measuring a liquid phase flow in a process line. In some aspects, the flow indicator 360 can be used i) to determine the amount of heat generated within the reaction zone 101, ii) to calculate the ethylene conversion within the reaction zone, iii) to control the reaction rate of the reaction in the reaction zone 101, or iv) combinations thereof. In a not shown aspect, the flow indicator can be 1) utilized to determine the amount of heat generated (e.g., through a calculation/processing unit coupled physically, via wire, or wirelessly to the flow indicator) within the reaction zone and/or the ethylene conversation, and/or 2) coupled (physically, via wire, or wirelessly) to process equipment and/or logic control to actuate one or more control valve(s) (not shown) to control the flow rates of the one or more reaction mixture components (e.g., ethylene, catalyst system or catalyst system components, optionally organic reaction medium, optionally hydrogen, or combinations thereof) into the reaction mixture via the one or more reaction zone inlets.

Similar to heat exchange system 210 of FIG. 2, heat exchange system 310 of FIG. 3 includes a pressure controller 130 (with or without the optional non-shown pressure sensor) and a pressure control device 131 in fluid communication with at least one of the process lines 201 (not shown) and/or 202 (shown) and process line 107 that is fluidly connected to process line 201 by process line 107. As described for FIG. 2, the pressure controllers of FIG. 3 can have the same features (e.g., outlet line 109, non-shown pressure sensor, non-shown control valve, among others) and functions as described for FIG. 2. For example, as in FIG. 2, pressure controller 130 and process line 107 in combination with outlet line 109, the unshown pressure sensor, and/or the unshown control valve can be configured, and/or actuate devices, to 1) provide the initial pressure (and/or in some instances control the pressure) on the first heat exchange surface second side 114 (or on second heat exchange surface first side 213 or on the heat exchange medium), 2) to remove non-condensable components within the first heat exchange medium, or 3) any combination thereof. Generally, pressure control device 130 and pressure controller 131 and any ancillary equipment (e.g., process line 107, the unshown pressure sensor, among other equipment) can be configured, can actuate devices, and/or can provide or control the pressure to be any pressure less than 1 atmosphere (101.3 kPa) described herein on the first heat exchange surface second side 114 (or the second heat exchange surface first side 213 and/or first heat exchange medium).

The heat exchange system 310 can further comprise temperature indicator and/or controller 324. Temperature indicator 324 can be fluidly connected to, or located in, at least one of the plurality of conduits allowing for flow of the first heat exchange medium from the first heat exchanger 111 (or from the first heat exchange surface second side 114) to the second heat exchanger 211 (or the second heat exchange surface first side 213), e.g., process line 202, and is configured to measure and/or monitor the temperature of the first heat exchange medium. In some aspects where vapor phase of the first heat exchange medium is present in the at least one of the plurality of conduits allowing for flow of the vapor phase of the first heat exchange medium from the first heat exchange surface second side 114 to the second heat exchange surface first side 213, temperature indicator and/or controller 334 in conjunction with a device and process logic to convert the temperature reading to pressure can serve as a pressure sensor for at least one of the one or more pressure controllers described herein (e.g., pressure controller 131). In one aspect, temperature indicator and/or controller 324 can be coupled to, or integrated into, at least one of the one or more pressure controllers described herein (e.g., pressure controller 131) and be utilized as the optional pressure sensor for at least one of the one or more pressure controllers described herein (e.g., pressure controller 131). In another aspect, temperature indicator and/or controller can be coupled (physically, via wire, or wirelessly) to at least one of the one or more pressure controllers described herein (e.g., pressure controller 131). In an aspect, a temperature indicator and/or controller 324, or temperature indicator and/or controller 324 via at least one of the one or more pressure controllers (e.g., pressure controller 131), can be configured to actuate liquid control valve 308 to control the second level of liquid phase first heat exchange medium on the second heat exchange surface first side 213 (and/or the first level of the first heat exchange medium on the first heat exchange surface second side 114) in response to the temperature and/or pressure transmitter to at least one of the one or more pressure control devices (e.g., pressure controller 131).

Reaction system 300 of FIG. 3 can further differ from reaction system 200 of FIG. 2 by having a temperature indicator and/or controller 321 in a process line of the reaction zone 101 comprising the reaction mixture (also referred to herein as a reaction mixture process line). Temperature indicator and/or controller 321 can be fluidly connected to, or located within, a reaction mixture process line (e.g., process line 103 (shown) or process line 102 (not shown)). While FIG. 3 shows temperature indicator and/or controller 321 as a single device, temperature indicator and/or controller 321 can comprise multiple temperature indicators and/or controllers located throughout the reaction zone process lines (including the reaction zone side of the heat exchange system, e.g., first heat exchanger or reaction zone side of the first heat exchange surface first side 113). The multiple temperature indicators and/or controllers can be utilized either individually or in combination (using control logic) to provide the function of temperature controller 321 (e.g., providing an average reaction mixture temperature). Temperature controller and/or indicator 321 can be configured to measure, monitor, and/or control a reaction mixture temperature (or average reaction mixture temperature) within the reaction zone.

Temperature indicator and/or controller 321 can be coupled with liquid control valve 308; alternatively, coupled with at least one of the one or more pressure control devices (e.g., pressure controller 130 and/or 131); alternatively, liquid control valve 308 and at least one of the one or more pressure control devices (e.g., pressure controller 130 and/or 131); or alternatively, liquid control valve 308 through at least one of the one or more pressure control devices (e.g., pressure controller 130 and/or 131). In an aspect, temperature indicator and/or controller 321 can be configured to actuate liquid control valve 308 to control the first level of the liquid phase of the first heat exchange medium in the first heat exchanger 111 (or on the first heat exchange surface second side 114) and/or the second level of the liquid phase of the first heat exchange medium in the second heat exchanger 211 (or on the second heat exchange surface first side 213) in response to the reaction mixture temperature (or average reaction mixture temperature). In another aspect, temperature indicator and/or controller 321 can be configured to control a pressure set point of at least one of the one or more pressure control devices (e.g., pressure controller 130 and/or 131) in response to reaction mixture temperature (or average reaction mixture temperature). The temperature indicator and/or controller can be coupled to a control valve (not shown), the one or more pressure control devices, or at least one of the one or more pressure control devices (e.g., pressure controller 130 and/or 131). Further, the temperature indicator and/or controller 321 can be configured to actuate the control valve (not shown) to control the pressure on the first heat exchange surface second side 114 and/or second heat exchange surface first side 213 (or first heat exchange medium) in response to the reaction mixture temperature (or average reaction mixture temperature). In another aspect, the temperature indicator and/or controller 321 is a) coupled to at least one of the pressure control devices (e.g. pressure control devices 130 and/or 131 and configured to actuate a control valve (not shown) control a pressure set point of the one or more pressure control devices in response to reaction mixture temperature (or average reaction mixture temperature)); b) coupled to the liquid control valve 308 and configured to actuate liquid control valve 308 to i) control the first level of the liquid phase of the first heat exchange medium on the first heat exchange surface second side (114), ii) control the second level of the liquid phase of the first heat exchange medium on the second heat exchange surface first side 213, or iii) any combination thereof; c) coupled with the first level indicator or controller 140 and configured to i) actuate the first control valve 302 to allow the addition of first heat exchange medium to the heat exchange system (or the first heat exchange medium circulation loop), and/or ii) actuate the second control valve 306 to allow the removal of first heat exchange medium from the heat exchange system (or the first heat exchange medium circulation loop) in response to reaction mixture temperature (or average reaction mixture temperature); or d) a combination thereof.

In an aspect, pressure controller 131 (with or without non-shown optional pressure sensor), temperature controller 321, temperature indicator 324 (which may or may not operate as the optional pressure sensor of pressure controller 131), at least one of the one or more pressure control devices (e.g., pressure control devices 130 and/or 131) and liquid control valve 308 can work together to control a) the reaction mixture temperature (or average reaction mixture temperature), b) the pressure on the first heat exchange surface second side 114 (or second heat exchange surface first side 213 or first heat exchange medium), and/or c) the first level of the first heat exchange medium on the first heat exchange surface second side 114 (and/or the second level of the first heat exchange medium on the second heat exchange surface first side 213). In an aspect, temperature indicator 134 in conjunction with a device and process logic to convert the temperature reading to pressure can serve as a pressure sensor for pressure controller 131. In an aspect, at least one of the one or more pressure controllers (e.g., pressure controller 131) and/or a temperature controller (e.g., temperature controller 321) can be configured to actuate a liquid control valve (e.g., liquid control valve 308) to control the second level of liquid phase first heat exchange medium on the second heat exchange surface first side 213 (and/or the first level of the first heat exchange medium on the first heat exchange surface second side 114) in response to the pressure measured by at least one of the one or more pressure control devices (e.g., pressure controller 131) and/or the reaction mixture temperature measured by the temperature controller (e.g., temperature controller 321). In an aspect, pressure control device 131 can be a pressure controller having a pressure sensor (not shown) in process line 202 (or utilize the reading from temperature indicator 324) and, optionally in conjunction with temperature controller 321, can be configured to: 1) receive pressure measurement signals from the pressure sensor (or converted temperature reading from temperature indicator 324), 2) optionally receive temperature measurement signals from temperature sensor 321, and 3) perform control logic to actuate control valve 308 (e.g., a liquid control valve) to control (maintain, adjust, increase and/or decrease) the second level of the first heat exchange medium on the second heat exchange surface first side 213 (and/or the first level of the first heat exchange medium on the first heat exchange surface second side 114). In some aspects, pressure controller can perform control logic that causes pressure control device 130 to control the pressure on the first heat exchange surface second side 114 (or second heat exchange surface first side 213, or first heat exchange medium) and/or remove non-condensable components in the first heat exchange medium out of the heat exchange medium via process lines 107 and 109.

In aspects, the components of reaction system 300 can work together to control the reaction mixture temperature (or average reaction mixture temperature by performing at least one or more of: a) controlling the pressure on the first heat exchange surface second side (or second heat exchange surface first side 213 and/or first heat exchange medium), b) controlling a first level of liquid phase of the first heat exchange medium on the first heat exchange surface second side 114 (and/or a second level of the first heat exchange medium on the second heat exchange surface first side 213), c) adding first heat exchange medium (liquid or vapor phase) to the heat exchange system 310 or removing a portion of the first heat exchange medium (liquid or vapor phase) from the heat exchange system 310; or d) controlling a flow of the first heat exchange medium out of the second heat exchanger 211 via liquid control valve 308.

In aspects, the components of reaction system 300 can work together to control a pressure on the first heat exchange surface second side 114 (or second heat exchange surface first side 213 or the first heat exchange medium) in the heat exchange system 310 by performing at least one or more of: a) utilizing a pressure control device to provide and/or control the pressure on the first heat exchange surface second side 114 (or second heat exchange surface first side 213 or the first heat exchange medium), b) controlling a first level of first heat exchange medium on the first heat exchange surface second side 114 (and/or a second level of first heat exchange medium on the second heat exchange surface first side 213, c) adding first heat exchange medium (liquid or vapor phase) to the heat exchange system 310 or removing a portion of the first heat exchange medium (liquid or vapor phase) from the heat exchange system 310, and d) controlling a flow of the first heat exchange medium out of the second heat exchanger 211 via liquid control valve 308.

As discussed herein, temperature controller 321, pressure controller 131 (in conjunction with a control valve (not shown) and/or temperature indicator and/or controller 324), liquid control valve 308, and/or level controller 140 (in conjunction with inlet line 301 and outlet line 305 and with their respective control values 302 and 306) can interact and/or can be integrated to control the reaction mixture temperature (or average reaction mixture temperature). For example, any combination, of 1) maintaining, increasing, or decreasing the second level of liquid phase of the first heat exchange medium in the second heat exchanger 211 (or on the second heat exchange surface first side 213) by controlling liquid control valve 308 to control the flow rate of liquid phase of the first heat exchange medium out of the second heat exchange 211, 2) maintaining, increasing, or decreasing the pressure set point on (or maintaining, increasing, or decreasing the pressure via) at least one of the one or more pressure controller devices (e.g., pressure control devices 130 and/or 131), and/or 3) maintaining, increasing, or decreasing the first level of liquid phase of the first heat exchange medium in the first heat exchanger Ill (or on the first heat exchange surface second side 114) by controlling the amount of first heat exchange medium in the first heat exchange medium circulation loop via action by level controller 140 to open control valve 302 or removing a portion of first heat exchange medium from the first heat exchange medium circulation loop via action of level controller 140 on first control valve 306 and/or second control valve can be utilized to achieve the desired control of the reaction mixture temperature (average reaction mixture temperature). It should be noted that when two or more of the interactive and/or integrated controls are utilized to achieve a desired control in the reaction mixture temperature (or the average reaction mixture temperature), not all of the interactive and/or integrated controls must have the same effect on reaction mixture temperature (average reaction mixture temperature) control as long as the desired control in the reaction mixture temperature (average reaction mixture temperature) is achieved. In these situations, other controls of the reaction system and/or heat exchange system may require adjustment (increase or decrease) to maintain proper operation of the reaction system and/or heat exchange system. For example, 1) maintenance of the reaction mixture temperature (average reaction mixture temperature) can be achieved by an appropriate adjustment (increase or decrease) of at least one of the control mechanisms that would result in an increase of the reaction mixture temperature (average reaction mixture temperature) and an appropriate adjustment (increase or decrease) of at least one of the control mechanisms that would result in an equal decrease of the reaction mixture temperature (average reaction mixture temperature), 2) increasing the reaction mixture temperature (average reaction mixture temperature) can be achieved by an adjustment (increase or decrease) of at least one of the control mechanisms that would result in an increase of the reaction mixture temperature (average reaction mixture temperature) and an adjustment (increase or decrease) of at least one of the control mechanisms that would result in a lessor decrease in the reaction mixture temperature (average reaction mixture temperature), and 3) decreasing the reaction mixture temperature (average reaction mixture temperature) can be achieved by an adjustment (increase or decrease) of at least one of the control mechanism that would result in an decrease of the reaction mixture temperature (average reaction mixture temperature) and an adjustment (increase or decrease) of at least one of the control mechanism that would result in a lessor increase of the reaction mixture temperature (average reaction mixture temperature), among other possibilities.

As discussed herein, pressure controller 131 (in conjunction with a control valve (not shown) and or temperature indicator and/or controller 324), liquid control valve 308, and/or level controller 140 (in conjunction with inlet line 301 and outlet line 305 and with their respective control values 302 and 306) can interact and/or can be integrated to control (maintain, adjust, increase or decrease) the pressure on the first heat exchange surface second 114 and/or the second heat exchange surface first side 213 (or the first heat exchange medium). For example, any combination, of 1) maintaining, increasing, or decreasing the second level of liquid phase of the first heat exchange medium in the second heat exchanger 211 (or on the second heat exchange surface first side 213) by controlling liquid control valve 308 to control the flow rate of liquid phase of the first heat exchange medium out of the second heat exchange 211, 2) maintaining, increasing, or decreasing the pressure set point on (or maintaining, increasing, or decreasing the pressure via) at least one of the one or more pressure controller devices (e.g., pressure control devices 130 and/or 131), and/or 3) maintaining, increasing, or decreasing the first level of liquid phase of the first heat exchange medium in the first heat exchanger 111 (or on the first heat exchange surface second side 114) by controlling the amount of first heat exchange medium in the first heat exchange medium circulation loop via action of level controller 140 on first control valve 302 and/or second control valve can be utilized to achieve the desired control (maintenance, adjustment, increase or decrease) of the pressure on the first heat exchange surface second side 114 and/or the second heat exchange surface first side 213 (or the first heat exchange medium). It should be noted that when two or more of the interactive and/or integrated controls are utilized to achieve a desired control of the pressure on the first heat exchange surface second side 114 and/or the second heat exchange surface first side 213 (or the first heat exchange medium), not all of the interactive and/or integrated controls must have the same effect on the pressure on the first heat exchange surface second side 114 and/or the second heat exchange surface first side 213 (or the first heat exchange medium) control as long as the desired control of the pressure on the first heat exchange surface second side 114 and/or the second heat exchange surface first side 213 (or the first heat exchange medium) is achieved. In these situations, other controls of the reaction system and/or heat exchange system may require adjustment (increase or decrease) to maintain proper operation of the reaction system and/or heat exchange system. For example, 1) maintenance of the pressure on the first heat exchange surface second side 114 and/or the second heat exchange surface first side 213 (or the first heat exchange medium) can be achieved by an appropriate adjustment (increase or decrease) of at least one of the control mechanisms that would result in an increase of the pressure and an appropriate adjustment (increase or decrease) of at least one of the control mechanisms that would result in an equal decrease of the pressure on the first heat exchange surface second side 114 and/or the second heat exchange surface first side 213 (or the first heat exchange medium), 2) increasing the pressure on the first heat exchange surface second side 114 and/or the second heat exchange surface first side 213 (or the first heat exchange medium) can be achieved by an adjustment (increase or decrease) of at least one of the control mechanisms that would result in an increase of the pressure and an adjustment of at least one of the control mechanisms that would result in a lessor decrease in the pressure on the first heat exchange surface second side 114 and/or the second heat exchange surface first side 213 (or the first heat exchange medium), and 3) decreasing the pressure on the first heat exchange surface second side 114 and/or the second heat exchange surface first side 213 (or the first heat exchange medium) can be achieved by an adjustment (increase or decrease) of at least one of the control mechanism that would result in an decrease of the pressure and an adjustment (increase or decrease) of at least one of the control mechanism that would result in a lessor increase of the pressure on the first heat exchange surface second side 114 and/or the second heat exchange surface first side 213 (or the first heat exchange medium), among other possibilities.

Generally, pressure control device 130 can be any pressure control device capable of providing less than 1 atmosphere (101.3 kPa) described herein. FIG. 4 illustrates a non-limiting example of the pressure control device 130 of FIG. 1, FIG. 2, and/or FIG. 3. Pressure control device 130 can be embodied as a control valve 401 (e.g., a motive fluid control valve) and an eductor 402. The motive fluid control valve 401 can be connected to the pressure controller 131 of FIG. 1, FIG. 2, and/or FIG. 3 and can be configured to actuate between a closed position and an open position so as to disallow or allow a motive fluid (e.g., steam or liquid water) in line 403 to flow into the eductor 402. The eductor 402 is fluidly connected to the motive fluid line 403 via a motive fluid inlet 402a. Eductor 402 is fluidly connected to the first heat exchange fluid process line (e.g. first heat exchange medium process line 202) via line 301 and eductor suction inlet 402b. The first heat exchange medium and/or non-condensable components in the first heat exchange medium process line 202 (or first heat exchange medium circulation loop) exit the eductor (and the heat exchange system) along with the motive fluid via outlet line 309 through eductor outlet 402c. When the control valve 401 is actuated to an open position, motive fluid flows in line 403 to the eductor 402, and the flow of motive fluid through the eductor 402 creates a suction or vacuum on line 301, which removes the first heat exchange medium and/or non-condensable components in first heat exchange medium process line 202 (or the first heat exchange medium circulation loop) from the heat exchange system. The first heat exchange medium, and/or non-condensable components in first heat exchange medium process line 202 (or the first heat exchange medium circulation loop) can flow from process line 202, into the eductor 402 via line 301 and out of the eductor 402 along with the motive fluid in line 309. When operating the heat exchange system such that a pressure on the heat exchange surface second side 114 (and/or second heat exchange surface first side 213 and/or heat exchange medium depending upon the actual heat exchange system) is any pressure less than 1 atmosphere (101.3 kPa) as disclosed herein, the suction or vacuum provided by the eductor 402 to the heat exchange surface second side 114 (and/or second heat exchange surface first side 213 and/or heat exchange medium depending upon the actual heat exchange system) is a pressure that is lower than the pressure on the heat exchange surface second side 114 (and/or second heat exchange surface first side 213 and/or heat exchange medium depending upon the actual heat exchange system). In some aspects, it is contemplated that the pressure on the heat exchange surface second side 114 (and/or second heat exchange surface first side 213 and/or heat exchange medium depending upon the actual heat exchange system) can be provided and/or controlled to be any pressure less than 1 atmosphere (101.3 kPa) using eductor 402 (e.g., in the heat exchange system 110 of reaction system 100); alternatively, eductor 402 can be utilized to provide the initial pressure in the heat exchange system and/or remove non-condensable components in first heat exchange medium process line 202 (e.g., in heat exchange system 210 of reaction system 200 or heat exchange system 310 of reaction system 300).

FIG. 5 illustrates the pressure control device of FIG. 1, FIG. 2, and/or FIG. 3 embodied as the control valve 401. Control valve 401 can be connected to, via process line 109, a vacuum system (not shown) or vacuum supplying device (not shown). The control valve 401 can be connected to the pressure controller 131 (and/or temperature controller 321 in the case of heat exchange system 310 of reaction system 300) and be configured to actuate between a closed position and an open position (upon receiving signals from the pressure controller 131) so as to disallow or allow the flow of first heat exchange medium and/or non-condensable components in first heat exchange medium process line 202 (or the first heat exchange medium circulation loop) from the heat exchange system. The pressure controller 131 (and/or temperature controller 321 in the case of heat exchange system 310 of reaction system 300) can be configured to open the control valve 401 when a pressure on the heat exchange surface first side 113 (in heat exchange system 210 of reaction system 200 or heat exchange system 310 of reaction system 300) of the first heat exchange medium is greater than the desired pressure that is any pressure less than 1 atmosphere (101.3 kPa) as described herein to i) provide an initial pressure on the heat exchange surface second side 114 (and/or the second heat exchange surface first side 213 and/or first heat exchange medium depending upon the actual heat exchange system), ii) control the pressure to any pressure less than any pressure less than 1 atmosphere (101.3 kPa) as described herein on the heat exchange surface first side 113 (and/or the second heat exchange surface first side 213 and/or first heat exchange medium depending upon the actual heat exchange system), and/or iii) remove non-condensable components in the first heat exchange medium. In an aspect, control valve 401 (along with the non-shown vacuum system or vacuum supplying device) can replace or be utilized in conjunction with eductor 402 as described herein.

Reaction systems 100, 200, and 300 of FIG. 1, FIG. 2, and FIG. 3, respectively, can further comprise one or more reaction zone inlets (not shown) to introduce one or more reaction mixture components into the reaction zone. The reaction mixture components can comprise at least ethylene, a catalyst system or catalyst system components, optionally an organic reaction medium, and optionally hydrogen. Reaction systems 100, 200, and 300 of FIG. 1, FIG. 2, and FIG. 3, respectively, can also further comprise one or more reaction zone outlets (not shown) to remove reaction mixture from the reaction zone. Reaction mixture removed from the reaction zone can be referred to as a reaction zone effluent. The reaction zone effluent can comprise at least ethylene, catalyst system (or its components), oligomer product, optionally reaction medium, and optionally hydrogen.

The reaction zone passing through heat exchange systems 110, 210 and 310 of reaction systems 100, 200, and 300 (respectively) can be any reaction zone 101 where heat can be exchanged between a reaction mixture within reaction zone 101 on the heat exchange surface first side 113 and the first heat exchange medium on the first heat exchange surface second side 114. In an aspect, the reaction zone 101 can be one where the reaction mixture can make a single pass through the first heat exchanger 111 (herein referred to as a single pass reaction zone or as a single pass heat exchange system), or the reaction zone can be one where the reaction mixture can make several passes through the heat exchanger 111 (herein referred to as a recycle reaction zone or a recycle heat exchange system). In an aspect, the reaction zone can be a single pass reaction zone; or alternatively, a recycle reaction zone. It should be noted that the single pass reaction zone or single pass heat exchange system referred to herein should not be confused with single, 2-pass, 3-pass, 4-pass, multipass, etc., heat exchangers where a fluid (e.g., a reaction mixture) makes one or multiple passes through a single heat exchanger before finally exiting the heat exchanger (which can have areas where the reaction mixture is not in contact the heat exchange surface). The single pass reaction zone or single pass heat exchange system refers to a reaction zone or using a heat exchange system where the reaction mixture enters (or passes through) the heat exchange system a single time, exits the heat exchange system, and is then processed to isolate the desired product (e.g., oligomer product). The recycle reaction zone or recycle heat exchange system refers to a reaction zone having a circulation loop where the reaction mixture is circulated through the heat exchange system multiple times prior to all of the reaction mixture being removed from the reaction zone (e.g., used in a batch reaction) or a portion of the reaction mixture being continuously or intermittently being removed from the reaction zone (e.g., used in a continuous reaction) to be processed to isolate the desired product (e.g., oligomer product).

Heat exchange systems 110, 210 and 310 of reaction systems 100, 200, and 300 (respectively) can be utilized in conjunction with a variety of reaction zones 101. Reaction system 100, 200, and 300 as depicted include process lines 102 and 103. Reaction systems 100, 200, and 300 only show process line 102 entering the heat exchanger 111 and process line 103 exiting heat exchanger 111, and thus reaction systems 100, 200, and 300 may, in some aspects, only show a portion of the entire reaction zone 101. One having ordinary skill in the art would recognize that heat exchange systems 110, 210 and 310 of reaction systems 100, 200, and 300 (respectively) can be utilized for any reaction zone operating at a reaction zone temperature less than the normal boiling point (i.e., boiling point at 1 atmosphere (101.3 kPa)) of a utilized first heat exchange medium. For brevity, only process line 102 entering and process line 103 exiting and heat exchanger 110 relating to the reaction zone 101 of reaction systems 100, 200, and/or 300 are shown in FIGS. 1, 2, and 3. Depending upon the specific reaction system, process lines 102 and 103 can be part of the reaction zone 101; or alternatively, process lines 102 and/or process line 103 may not be part of the reaction zone; i.e. process line 102 can represent one or more reaction mixture component feed lines which can introduce one or more reaction mixtures (e.g., at least ethylene, a catalyst system or catalyst system components, optionally an organic reaction medium, and optionally hydrogen) to reaction zone 101 or into reaction zone 101 within heat exchanger 111 while process line 103 can represent a reaction zone outlet line which can remove/withdrawn reaction mixture from the reaction zone 101 (or the first heat exchanger 111) and/or reaction zone 101 within heat exchanger 111.

In an aspect, reaction zone 101 of reaction systems 100, 200, and 300 of FIG. 1. FIG. 2, and FIG. 3 minimally comprise the portion of the heat exchanger 111 through which the reaction mixture flows (and contacts the first heat exchange surface first side) and which has all the necessary reaction components and reaction conditions such that the reaction can occur at a desired rate. In an aspect, at least a portion of process line 102 and/or process line 103 can form part of the reaction zone if all the necessary reaction components and reaction conditions are present such that the reaction can occur at a desired rate. In one aspect, process line 102 can represent one or more reaction mixture component feed lines which can introduce one or more reaction mixture components into the first heat exchanger 111. The reaction mixture components which can be introduced via the one or more reaction mixture component feed lines represented by process line 102 can comprise ethylene, catalyst system or catalyst system components, optionally organic reaction medium, optionally hydrogen, or combinations thereof. In a combinable aspect, process line 103 can represent the reaction zone outlet lines which remove the reaction mixture from the reaction zone (or the first heat exchanger 111). In an aspect, at least a portion of process lines 102 and 103 can represent a portion of the reaction zone if all the necessary reaction components and reaction conditions are present in process lines 102 and/or 103 such that the reaction can occur at a desired rate. In an aspect, heat exchanger 111 can be a typical heat exchanger (e.g., one or more plug flow reactors set up as a heat exchanger). In other aspects heat exchanger 111 can be one or more reactors independently selected from autoclave reactor, stirred tank reactor, or a continuous stirred tank reactor (CSTR) having internal heat exchange coils and/or external heat exchange jackets.

In an aspect, reaction zone 101 of reaction systems 100, 200, and 300 of FIG. 1, FIG. 2, and FIG. 3 (respectively) can comprise first heat exchanger 111 (i.e., the first heat exchange surface first side 112 through which the reaction mixture flows) and two or more reaction zone lines (e.g., process lines 102 and 103) through which the reaction mixture flows. Generally, the two or more reaction zone lines can comprise the reaction mixture. At least one of the two or more reaction zone lines is a reaction zone first heat exchanger inlet line(s) (e.g., process line 102) coupled to one or more first heat exchanger inlets (not numbered) and configured to introduce the reaction mixture into the first heat exchanger 111. The reaction mixture entering the first heat exchanger 111 is thus contacted with the first heat exchange surface first side 113. At least one of the two or more reaction zone lines is a reaction zone first heat exchanger outlet line(s) (e.g., process line 103) coupled to one or more first heat exchanger outlets (not numbered) and configured to remove reaction mixture from the first heat exchanger 111. The reaction mixture exiting the first heat exchanger 111 via at least one of the two or more reaction zone lines is a reaction zone first heat exchanger outlet line(s) (e.g., process line 103) is thus removed from contacting the first heat exchange surface first side 113. FIG. 6, illustrates an aspect of a portion of reaction systems 100, 200, and 300 of FIG. 1, FIG. 2, and FIG. 3 (respectively), wherein the reaction mixture is circulated through a reaction mixture circulation loop comprising first heat exchanger 111 (i.e., the first heat exchange surface first side 113 through which the reaction mixture flows) and two or more reaction zone lines (e.g., process lines 102 and 103). The reaction zone 101 portion of reaction systems 100, 200, and 300 differ from the reaction systems 100, 200, and 300 in that the reaction zone 101 can further comprise a motive device fluidly connecting the reaction zone first heat exchanger inlet line(s) and the reaction zone first heat exchanger outlet line(s) configured to form a reaction mixture circulation loop, where the motive device is configured to circulate the reaction mixture through the reaction mixture circulation loop.

The motive device 120 of the reaction zone 101 of reaction systems 100, 200, and 300 of FIG. 1, FIG. 2, and FIG. 3 (respectively) can be any device which can cause the reaction mixture to circulate through the reaction mixture circulation loop. In an aspect the motive device 120 can be any type of pump which can circulate the reaction mixture (e.g., an in-line axial flow pump with a pump impeller, among others) through motive device 120 via motive device line 121. In an aspect, the motive device, during operation, can provide turbulent flow for the reaction mixture circulating through the reaction mixture circulation loop or at least through the portion of the circulation loop where the reaction mixture contacts the first heat exchange surface second side. The impeller can be driven by a motor or other motive force. In some aspects, insulation can be placed around process lines 102 and/or 103, or any other part of the reaction zone 101 (e.g., a vessel) that is/are not part of the heat exchange system 110 to reduce reaction mixture heat loss in these sections of the reaction zone.

In an aspect, the reaction zone 101 of reaction systems 100, 200, and/or 300 depicted in FIG. 6 can further comprise one or more reactors (not shown). Each reactor can be located within the reaction mixture circulation loop. In an aspect, each reactor independently, can be located upstream of the motive device (at a position on the intake side of a pump) or downstream of the motive device (on the discharge side of the pump). Each reactor independently can be fluidly connected to the reaction zone first heat exchanger inlet line(s) (e.g., process line 102), the reaction zone first heat exchanger outlet line(s) (e.g., process line 103), and the first heat exchange surface first side 113. In an aspect, each reactor independently can be located between motive device 120 and first heat exchanger inlet (e.g., on process line 102) or between the first heat exchanger outlet (e.g., process line 103). In aspects where one or more other reactors are included as part of the reaction zone 101, each of the one or more reactors independently can be an autoclave reactor, a stirred tank reactor, a continuous stirred tank reactor, a plug flow reactor, or any combination thereof; alternatively, a stirred tank reactor, alternatively, a continuous stirred tank reactor, or alternatively, a plug flow reactor. In an aspect, each of the one or more reactors included as part of the reaction zone 101 independently can have or not have internal heat exchange coil(s) and/or external heat exchange jacket(s). In some aspects, where one or more other reactors are included as part of the reaction zone 101, each of the one or more reactors can be an autoclave reactor, continuous stirred tank reactor, a gas phase reactor, a solution reactor, a tubular reactor, a bubble reactor, or any combination thereof; alternatively, autoclave reactor; alternatively, stirred tank reactor; alternatively, a gas phase reactor; alternatively, a solution reactor; alternatively, a tubular reactor; or alternatively, a bubble reactor. In some embodiments, the reaction zone can comprise different types of reactors in combination, and in various arrangements. In an embodiment, where one or more other reactors are included as part of the reaction zone 101, each of the one or more reactors can have a mechanical agitator to stir and/or create turbulent flow within the vessel; alternatively, in place of, or in conjunction with the mechanical agitator the one or more reactors can have internal baffles, a gas sparger, or any combination thereof. Each of the one or more reactors included as part of the reaction zone independently can be located within process line 102 and/or process line 103. In another aspect, the reaction zone 101 of reaction systems 100, 200, and/or 300 depicted in FIG. 6 may not comprise an independent reactor.

The processes and reaction of reaction systems described herein can be a batch process or a continuous process; alternatively, a batch process; or alternatively, a continuous process. In a batch process, the components of the reaction mixture (e.g., at least ethylene, a catalyst system or catalyst system components, optionally an organic reaction medium, and optionally hydrogen) are introduced into the reaction zone via one or more reaction zone inlets (not shown) and reaction mixture circulated through the reaction zone, thereby passing through the first heat exchanger 111 of heat exchange systems 110, 210, or 310 to form the desired product (e.g., an oligomer product). Generally, the reaction mixture is circulated through the reaction zone until a desired feedstock (e.g., ethylene) conversion is achieved, a desired catalyst system productivity is achieved, and/or a desired quantity of product (e.g., oligomer product) is produced. In the continuous process, the components of the reaction mixture (e.g., at least ethylene, a catalyst system or catalyst system components, optionally an organic reaction medium, and optionally hydrogen) are continuously or intermittently introduced into the reaction zone via one or more reaction zone inlets (not shown) while reaction mixture is continuously or intermittently withdrawn from the reaction zone (alternatively a reaction zone effluent is withdrawn from the reaction zone). The continuous reaction zone is operated to provide a desired feedstock (e.g., ethylene) conversion, a desired catalyst system productivity, and/or a desired product (e.g., oligomer product) discharge rate.

The reaction systems described herein can be selected from the group consisting of an ethylene oligomerization reaction system, an ethylene trimerization reaction system, an ethylene tetramerization reaction system, and an ethylene trimerization and tetramerization reaction system; alternatively, an ethylene oligomerization reaction system; alternatively, an ethylene trimerization reaction system; alternatively, an ethylene tetramerization reaction system; or alternatively, an ethylene trimerization and tetramerization reaction system. Designs for reactor/reaction zone are described in U.S. Pat. No. 10,513,473 to Kreischer, entitled "Ethylene Oligomerization/Trimerization/Tetramerization Reactor". The designs described therein and the features of the processes, reactors, reaction zones, and/or reaction systems can be utilized to further describe processes, reactors, reaction zones, and/or reaction systems described herein. In an aspect, of the processes and reaction systems described herein, not all of the reaction mixture may contact the first heat exchange surface first side or indirectly contact the first heat exchange medium at the same time. Consequently, in an aspect, at least a portion of the reaction mixture can contact the first heat exchange surface first side or can indirectly contact the first heat exchange medium. Generally, the portion of the reaction mixture that contacts the first heat exchange surface first side or indirectly contacts the first heat exchange medium is considered to be the volume of the reaction mixture included in the interior volume of the first heat exchange surface. For example, for a cylindrical portion of the reaction zone, the at least a portion of the reaction mixture that contacts the first heat exchange surface first side, or indirectly contacts the first heat exchange medium, is the portion of the reaction mixture within the interior volume of the cylinder having theoretical end planes at the location between where the first heat exchange surface begins and ends. The portion of the reaction mixture that falls within the theoretical end planes at the location between where the first heat exchange surface begins and ends can be referred to as the heat exchanged reaction mixture volume. In an aspect, a ratio of heat exchanged reaction mixture volume to the total reaction mixture volume within the reaction zone can have a minimum value of (i.e., or greater than or equal to) 1:1, 1.5:1, 2:1, 2.5:1, 3:1, or 4:1; alternatively or additionally, a maximum value of (i.e., less than or equal to) 100:1, 50:1, 20:1, 15:1, 12:1, or 9:1. In an aspect, the ratio of heat exchanged reaction mixture volume to the total reaction mixture volume within the reaction zone can range from any minimum value disclosed herein to any maximum value disclosed herein. In some non-limiting aspects, the ratio of heat exchanged reaction mixture volume to the total reaction mixture volume within the reaction zone can range from 1:1 to 100:1, from 1.5:1 to 100:1, from 2:1 to 100:1, from 3:1 to 100:1, from 4:1 to 100:1, from 3:1 to 50:1, from 3:1 to 20:1, from 4:1 to 50:1, from 4:1 to 15:1, or from 4:1 to 12:1. Other ratios of heat exchanged reaction mixture volume to the total reaction mixture volume within the reaction zone are readily apparent to those skilled in the art with the aid of this disclosure.

The processes and reaction systems described herein can provide advantageous temperature control. In an aspect, a temperature difference between an average reaction mixture temperature on the first heat exchange surface first side and a first heat exchange medium temperature on the first heat exchange surface second side can be, or can be controlled to be less than 20° C., 15° C., 10° C. 7.5° C., 5° C., 4° C., or 3° C.; alternatively, or additionally, the first heat exchange medium temperature on the first heat exchange surface second side can be (or can be controlled to be) within any percentage of an average reaction mixture temperature on the first heat exchange surface first side disclosed herein (e.g., 20%, 15%, 12.5%, 10%, 7.5%, 6%, 5%, or 4.5%). In an aspect, a reaction mixture temperature at any point in the reaction zone can be, or can be controlled to be, within 15° C., 10° C., 7.5° C., 5° C., 4° C., 3° C., or 2° C. of an average reaction mixture temperature in the reaction zone; alternatively or additionally, a reaction mixture temperature at any point in the reaction zone can be, or can be controlled to be, within 3%, 2%, 1.5%, 1%, 0.8%, 0.6%, 0.5%, 0.45%, 0.4%, 0.35%, 0.3%, 0.25%, or 0.2% of an average reaction mixture temperature in the reaction zone. The temperature percentage values refer to a comparison of the temperatures on an absolute temperature scale (i.e., K or ° R).

The reaction system can have a ratio of the heat exchanged reaction mixture volume to the total reaction mixture volume selected to maintain a desired temperature and/or temperature profile of the reaction mixture within the reaction zone. In an embodiment, the minimum ratio of the heat exchanged reaction mixture volume to the total reaction mixture volume can be greater than or equal to 0.7, 0.75, or 0.8; alternatively or additionally, the maximum ratio of the heat exchanged reaction mixture volume to the total reaction mixture volume can be less than or equal to 1.0, 0.975, 0.95, 0.925, or 0.9. In an embodiment, the ratio of the heat exchanged reaction mixture volume to the total reaction mixture volume can range from any minimum the ratio of the heat exchanged reaction mixture volume to the total reaction mixture volume described herein to any maximum the ratio of the heat exchanged reaction mixture volume to the total reaction mixture volume described herein. In some embodiments, suitable ranges for the ratio of the heat exchanged reaction mixture volume to the total reaction mixture volume can include, but are not limited to, from 0.7 to 1.0, from 0.75 to 1, from 0.8 to 1, from 0.75 to 0.975, from 0.75 to 0.95, from 0.8 to 0.975, from 0.8 to 0.95, or from 0.8 to 0.925. Other suitable ranges for the ratio of the heat exchanged reaction mixture volume to the total reaction mixture volume are readily apparent from the present disclosure.

The process described herein can further comprise a) introducing at least 1) ethylene, 2) a catalyst system or catalyst system components comprising i) a heteroatomic ligand transition metal compound complex and an organoaluminum compound or ii) a heteroatomic ligand, a transition metal compound, and an organoaluminum compound, 3) optionally, an organic reaction medium, and 4) optionally, hydrogen into a reaction zone (or into a reaction mixture within a reaction zone); and b) forming an oligomer product in the reaction zone. For the reaction systems described herein, at least 1) ethylene, 2) a catalyst system or catalyst system components comprising i) a heteroatomic ligand transition metal compound complex and an organoaluminum compound or ii) a heteroatomic ligand, a transition metal compound, and an organoaluminum compound, 3) optionally, an organic reaction medium, and 4) optionally, hydrogen can be introduced into the reaction zone (or into the reaction mixture in the reaction zone). Generally, the reaction mixture of the process described herein and the reaction zone of the reaction systems described herein can comprise at least 1) ethylene, 2) a catalyst system or catalyst system components comprising i) a heteroatomic ligand transition metal compound complex and an organoaluminum compound or ii) a heteroatomic ligand, a transition metal compound, and an organoaluminum compound, 3) an oligomer product, 4) optionally, an organic reaction medium, and 5) optionally, hydrogen. The catalyst system, catalyst components, heteroatomic ligand transition metal compound complex, heteroatomic ligand, transition metal compound, organoaluminum compound, and optional organic reaction medium, are independently described herein and these independent descriptions can be utilized without limitation and in any combination to further describe the processes and reactions systems described herein.

The processes and reaction systems disclosed herein can utilize a catalyst system or catalyst system components comprising i) a heteroatomic ligand transition metal compound complex and an organoaluminum compound or ii) a heteroatomic ligand, a transition metal compound, and an organoaluminum compound; alternatively, a heteroatomic ligand transition metal compound complex and an organoaluminum compound; or alternatively, a heteroatomic ligand, a transition metal compound, and an organoaluminum compound. In some aspects, the catalyst system (or catalyst system mixture) comprising i) a heteroatomic ligand transition metal compound complex and an organoaluminum compound or ii) a heteroatomic ligand, a transition metal compound, and an organoaluminum compound) is introduced into the reaction mixture within the reaction zone. In other aspects, the two or more of catalyst system components (e.g., catalyst system components) comprising a heteroatomic ligand transition metal compound complex and an organoaluminum compound or ii) a heteroatomic ligand, a transition metal compound, and an organoaluminum compound) are separately introduced into the reaction mixture within the reaction zone. The heteroatomic ligand, the heteroatomic ligand of the heteroatomic ligand transition metal compound complex, the transition metal compound, the transition metal compound of the heteroatomic ligand transition metal compound, the heteroatomic ligand transition metal compound complex, and the organoaluminum compound are independent elements of the catalyst system or catalyst system components used in the processes described herein and are independently described herein. These independently described catalyst system or catalyst system component elements can be utilized in any combination, and without limitation, to further describe the processes provided herein.

In an aspect, the catalyst system or the catalyst system components can comprise 1) a heteroatomic ligand and a transition metal compound or ii) a heteroatomic ligand transition metal compound complex; alternatively, a heteroatomic ligand and a transition metal compound; or alternatively, a heteroatomic ligand transition metal compound complex. Generally, the heteroatomic ligand transition metal compound complex of the catalyst systems described herein can be composed of the heteroatomic ligand and the transition metal compound. The heteroatomic ligand and the transition metal compound are independent elements of the heteroatomic ligand transition metal compound complex and are independently described herein. The independent descriptions of the heteroatomic ligand and the transition metal compound can be utilized without limitation, and in any combination, to further describe the catalyst system heteroatomic ligand transition metal compound complex or the heteroatomic ligand and transition metal compound of the catalyst systems described herein.

Generally, the heteroatomic ligand or the heteroatomic ligand of the heteroatomic ligand transition metal compound complex can be any heteroatomic ligand, which when utilized in the catalysts systems (or as a component in the catalyst systems) described herein for the processes and/or reaction systems described herein, can form an oligomer production in the reaction zone. In an aspect, the heteroatomic ligand or the heteroatomic ligand of the heteroatomic ligand transition metal compound complex can be a neutral heteroatomic ligand or an anionic heteroatomic ligand; alternatively, a neutral heteroatomic ligand; or alternatively, an anionic heteroatomic ligand. In an aspect, the neutral heteroatomic ligand can comprise one or more heteroatomic complexing moieties; alternatively, two heteroatomic complexing; or alternatively, three heteroatomic complexing moieties. In an aspect, the anionic heteroatomic ligand can also comprise one or more neutral heteroatomic complexing moieties; alternatively, two heteroatomic complexing; or alternatively, three heteroatomic complexing moieties. In an aspect, the each neutral heteroatomic complexing moiety of the neutral ligand or the anionic ligand comprising a neutral heteroatomic complexing moiety independently can be an ether group, a sulfide group, an amine group, an imine group, a phosphine group, a phosphinite group, a phosphonite group, or a phosphite group; alternatively, an ether group, a sulfide group, an amine group, an imine group, or a phosphine group; alternatively, an ether group; alternatively, a sulfide group; alternatively, an amine group; alternatively, an imine group; or alternatively, a phosphine group. In an aspect, the anion atom of the anionic heteroatomic ligand (which forms a covalent or ionic bond with the transition metal of the transition metal compound) can be an anionic carbon atom, an anionic oxygen atom, or an anion nitrogen atom; alternatively, an anionic carbon atom; alternatively, an anionic oxygen atom; or alternatively, an anion nitrogen atom.

In an aspect, the heteroatomic ligand transition metal compound complex can have the general formula $[(HetLig)MX_pQ_q]^{s-p}$; wherein HetLig represents the heteroatomic ligand, M represents the transition metal, X is an monoanionic ligand and p is an integer, Q is a neutral ligand, q is an integer, s is an integer representing the oxidation state of the transition metal M. and wherein any two or more of the X and Q ligands may be linked to form a multidentate ligand. Therefore, for the general and specific structures disclosed hereinbelow, it is envisioned that any two or more of the X and Q ligands can form a chelating ligand in which a bridging moiety links X ligands, Q ligands, or a combination of X and Q ligands. In an non-limiting aspect, the heteroatomic ligand-metal compound complex can be heteroatomic ligand chromium compound complex and can have the general formula $[(HetLig)CrX_pQ_q]^{s-p}$; wherein HetLig represents the one or more first training heteroatomic ligands, X is an monoanionic ligand and p is an integer, Q is a neutral ligand, q is an integer, and s is an integer representing the oxidation state of the chromium atom, and wherein any two or more of the X and Q ligands may be linked to form a multidentate ligand. Therefore, for the general and specific structures disclosed hereinbelow, it is envisioned that any two or more of the X and Q ligands can form a chelating ligand in which a bridging moiety links X ligands, Q ligands, or a combination of X and Q ligands.

In any aspect, the heteroatomic ligand or the heteroatomic ligand of the heteroatomic ligand transition metal compound complex can comprise, can consist essentially of, or can be, an $N^2$-phosphinyl formamidine, an $N^2$-phosphinyl amidine, an $N^2$-phosphinyl guanidine, a heterocyclic 2-[(phosphinyl)aminyl]imine, or any combination thereof; alternatively, an $N^2$-phosphinyl formamidine; alternatively, an $N^2$-phosphinyl amidine; alternatively, an $N^2$-phosphinyl guanidine; or alternatively, a heterocyclic 2-[(phosphinyl)aminyl]imine. Generally, the an $N^2$-phosphinyl formamidine can have Structure NPF1, the $N^2$-phosphinyl amidine can have Structure NPA1, the $N^2$-phosphinyl guanidine can have Structure Gu1, Structure Gu2, Structure Gu3, Structure Gu4, or Structure Gu5, and the heterocyclic 2-[(phosphinyl)aminyl]imine can have structure HCPA1. In some aspects, the $N^2$-phosphinyl guanidine have Structure Gu2, Structure Gu3, or Structure Gu4; alternatively, Structure Gu1; alternatively, Structure Gu2; alternatively, Structure Gu3; alternatively, Structure Gu4; or alternatively, Structure Gu5.

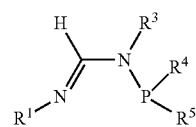

Structure NPF1

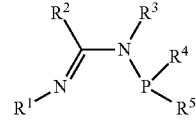

Structure NPA1

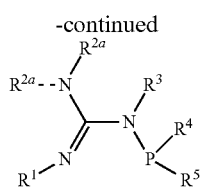

Structure Gu1

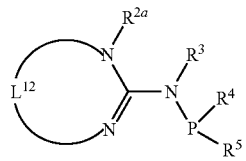

Structure Gu2

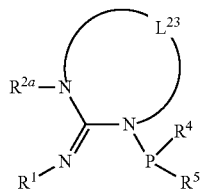

Structure Gu3

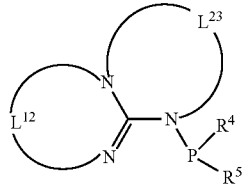

Structure Gu4

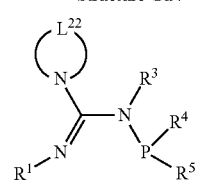

Structure Gu5

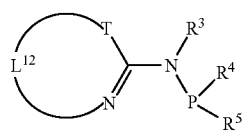

Structure HCPA1

In any aspect, the heteroatomic ligand transition metal compound complex can comprise, can consist essentially of, or can be, an $N^2$-phosphinyl formamidine transition metal compound complex, an $N^2$-phosphinyl amidine transition metal compound complex, an $N^2$-phosphinyl guanidine transition metal compound complex, a heterocyclic 2-[(phosphinyl)aminyl]imine transition metal compound complex, or any combination thereof; alternatively, an $N^2$-phosphinyl formamidine transition metal compound complex; alternatively, an $N^2$-phosphinyl amidine transition metal compound complex; alternatively, an $N^2$-phosphinyl guanidine transition metal compound complex; or alternatively, a heterocyclic 2-[(phosphinyl)aminyl]imine transition metal compound complex. Generally, the an $N^2$-phosphinyl formamidine transition metal compound complex can have Structure NPFM1, the $N^2$-phosphinyl amidine transition metal compound complex can have Structure NPAM1, the $N^2$-phosphinyl guanidine transition metal compound complex can have Structure GuM1, Structure GuM2, Structure GuM3, Structure GuM4, or Structure GuM5, and the heterocyclic 2-[(phosphinyl)aminyl]imine transition metal compound complex can have Structure HCPAM1. In some aspects, the $N^2$-phosphinyl guanidine transition metal compound complex have Structure GuM2, Structure GuM3, or Structure GuM4; alternatively, Structure GuM1; alternatively, Structure GuM2; alternatively, Structure GuM3; alternatively, Structure GuM4; or alternatively, Structure GuM5.

Structure NPFM1

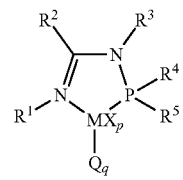

Structure NPAM1

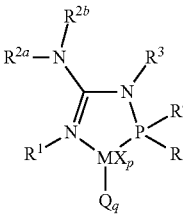

Structure GuM1

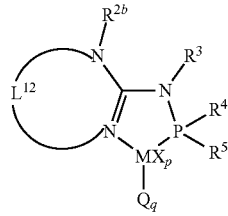

Structure GuM2

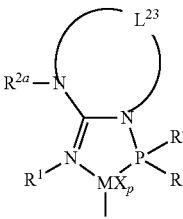

Structure GuM3

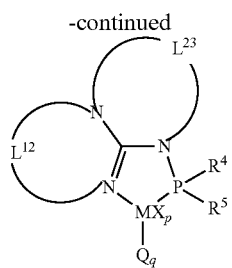

Structure GuM4

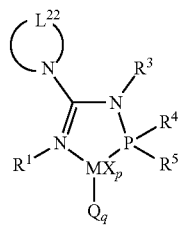

Structure GuM5

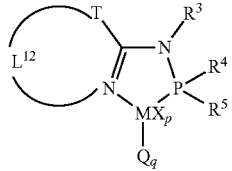

Structure HCPAM1

Within the $N^2$-phosphinyl formamidines, the $N^2$-phosphinyl formamidine transition metal compound complexes, the $N^2$-phosphinyl amidines, the $N^2$-phosphinyl amidine transition metal compound complexes, and the heterocyclic 2-[(phosphinyl)aminyl]imine transition metal compound complexes the nitrogen participating in a double bond with the central carbon atom is referred to as the $N^1$ nitrogen and the nitrogen atom participating in a single bond with the central carbon atom is referred to as the $N^2$ nitrogen. Similarly, within the $N^2$-phosphinyl guanidines and the $N^2$-phosphinyl guanidine transition metal compound complexes, the nitrogen participating in a double bond with the central carbon atom of the guanidine core is referred to as the $N^1$ nitrogen, the nitrogen atom participating in a single bond with the central carbon atom of the guanidine core and a bond with the phosphorus atom of the phosphinyl group is referred to as the $N^2$ nitrogen, and the remaining nitrogen atom participating in a single bond with the central carbon atom of the guanidine core is referred to as the $N^3$ nitrogen. It should be noted that the guanidine group of the guanidine in the $N^2$-phosphinyl guanidines and the $N^2$-phosphinyl guanidine transition metal compound complexes can be a portion of a larger group which does not contain guanidine in it name. For example, while the compound 7-dimethylphosphinylimidazo[1,2-a]imidazole could be classified as a compound having an imidazo[1,2-a]imidazole core (or a compound having a phosphinylimidazo[1,2-a]imidazole group), 7-dimethylphosphinylimidazo[1,2-a]imidazole would still be classified as a compound having a guanidine core (or as a compound having an guanidine group) since it contains the defined general structure of the guanidine compound.

The $R^1$, $R^3$, $R^4$, and $R^5$ groups within the $N^2$-phosphinyl formamidine structures and the $N^2$-phosphinyl formamidine transition metal compound complex structures, $R^1$, $R^2$, $R^3$, $R^4$, and $R^5$ within the $N^2$-phosphinyl amidine structures and the $N^2$-phosphinyl amidine transition metal compound complex structures, $R^1$, $R^{2a}$, $R^{2b}$, $R^3$, $R^4$, $R^5$, $L^{12}$, $L^{22}$, and $L^{23}$ within the $N^2$-phosphinyl guanidine structures and the $N^2$-phosphinyl guanidine transition metal compound complex structures, and $L^{12}$, T, $R^3$, $R^4$, and $R^5$ within the heterocyclic 2-[(phosphinyl)aminyl]imine structures and heterocyclic 2-[(phosphinyl)aminyl]imine transition metal compound complex structures are independently described herein and can be utilized in any combination and without limitation to further describe the $N^2$-phosphinyl formamidine structures, the $N^2$-phosphinyl formamidine transition metal compound complex structures, the $N^2$-phosphinyl amidine structures, the $N^2$-phosphinyl amidine transition metal compound complex structures, the $N^2$-phosphinyl guanidine structures, the $N^2$-phosphinyl guanidine transition metal compound complex structures, the heterocyclic 2-[(phosphinyl)aminyl]imine structures, and the heterocyclic 2-[(phosphinyl)aminyl]imine transition metal compound complex structures disclosed herein. $X_p$, Q, and q of the $N^2$-phosphinyl formamidine transition metal compound complex structures, the $N^2$-phosphinyl amidine transition metal compound complex structures, the $N^2$-phosphinyl guanidine transition metal compound complex structures, and the heterocyclic 2-[(phosphinyl)aminyl]imine transition metal compound complex structures are independently described herein and can be utilized in any combination, and without limitation, to further describe the $N^2$-phosphinyl formamidine transition metal compound complex structures, the $N^2$-phosphinyl amidine transition metal compound complex structures, the $N^2$-phosphinyl guanidine transition metal compound complex structures, and the heterocyclic 2-[(phosphinyl)aminyl]imine transition metal compound complex structures disclosed herein. Additionally, the independent descriptions of $X_p$, Q, and q can be combined, without limitation, with the independently described $R^1$, $R^2$, $R^{2a}$, $R^{2b}$, $R^3$, $R^4$, $R^5$, $L^{12}$, $L^{22}$, and $L^{23}$ to further describe the appropriate $N^2$-phosphinyl formamidine transition metal compound complex structures, the $N^2$-phosphinyl amidine transition metal compound complex structures, the $N^2$-phosphinyl guanidine transition metal compound complex structures, and the heterocyclic 2-[(phosphinyl)aminyl]imine transition metal compound complex structures contemplated herein.

Generally, $R^1$ of the $N^2$-phosphinyl formamidines, the $N^2$-phosphinyl formamidine transition metal compound complexes, the $N^2$-phosphinyl amidines, the $N^2$-phosphinyl amidine transition metal compound complexes, the $N^2$-phosphinyl guanidines, and/or the $N^2$-phosphinyl guanidine transition metal compound complexes which have an R group can be an organyl group; alternatively, an organyl group consisting of inert functional groups; or alternatively, a hydrocarbyl group. In an aspect, the $R^1$ organyl group can be a $C_1$ to $C_{20}$, a $C_1$ to $C_{15}$, a $C_1$ to $C_{10}$, or a $C_1$ to $C_5$ organyl group. In an aspect, the $R^1$ organyl group consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, the $R^1$ hydrocarbyl group can be a $C_1$ to $C_{20}$, a $C_1$ to $C_{15}$, a $C_1$ to $C_{10}$, or a $C_1$ to $C_5$ hydrocarbyl group.

In an aspect, $R^1$ of the $N^2$-phosphinyl formamidines, the $N^2$-phosphinyl formamidine transition metal compound complexes, the $N^2$-phosphinyl amidines, the $N^2$-phosphinyl amidine transition metal compound complexes, the $N^2$-phosphinyl guanidines, and/or the $N^2$-phosphinyl guanidine transition metal compound complexes which have an R group can be an alkyl group, a substituted alkyl group, a cycloalkyl group, a substituted cycloalkyl group, an aryl group, a substituted aryl group, an aralkyl group, or a substituted aralkyl group; alternatively an alkyl group or a substituted alkyl group; alternatively, a cycloalkyl group or a substituted cycloalkyl group; alternatively, an aryl group or a substituted aryl group; alternatively, an aralkyl group or a substituted aralkyl group; alternatively, an alkyl group, a cycloalkyl group, an aryl group, or an aralkyl group; alternatively, an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the $R^1$ alkyl group can be a $C_1$ to $C_{20}$, a $C_1$ to $C_{10}$, or a $C_1$ to $C_5$ alkyl group. In any aspect disclosed herein, the $R^1$ substituted alkyl group can be a $C_1$ to $C_{20}$, a $C_1$ to $C_{10}$, or a $C_1$ to $C_5$ substituted alkyl group. In any aspect disclosed herein, the $R^1$ cycloalkyl group can be a $C_4$ to $C_{20}$, a $C_4$ to $C_{15}$, or a $C_4$ to $C_{10}$ cycloalkyl group. In any aspect disclosed herein, the $R^1$ substituted cycloalkyl group can be a $C_4$ to $C_{20}$, a $C_4$ to $C_{15}$, or a $C_4$ to $C_{10}$ substituted cycloalkyl group. In any aspect disclosed herein, the $R^1$ aryl group can be a $C_6$ to $C_{20}$, a $C_6$ to $C_{15}$, or a $C_6$ to $C_{10}$ aryl group. In any aspect disclosed herein, the $R^1$ substituted aryl group can be a $C_6$ to $C_{20}$, a $C_6$ to $C_{15}$, or a $C_6$ to $C_{10}$ substituted aryl group. In any aspect disclosed herein, the $R^1$ aralkyl group can be a $C_7$ to $C_{20}$, a $C_7$ to $C_{15}$, or a $C_7$ to $C_{10}$ aralkyl group. In any aspect disclosed herein, the $R^1$ substituted aralkyl group can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted $R^1$ group.

In an aspect, $R^1$ can be a methyl group, an ethyl group, a propyl group, a butyl group, a pentyl group, a hexyl group, a heptyl group, or an octyl group; or alternatively, a methyl group, an ethyl group, a n-propyl (1-propyl) group, an iso-propyl (2-propyl) group, a tert-butyl (2-methyl-2-propyl) group, or a neopentyl (2,2-dimethyl-1-propyl) group. In some aspects, the alkyl groups which can be utilized as $R^1$ can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as $R^1$.

In an aspect, $R^1$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group. In an aspect, the substituted cycloalkyl group, which can be utilized as $R^1$, can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect, one or more substituents of a multi-substituted cycloalkyl group utilized as $R^1$ can be the same or different; alternatively, all the substituents of a multi-substituted cycloalkyl group can be the same, or alternatively, all the substituents of a multi-substituted cycloalkyl group can be different. Each substituent of a substituted cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy (general and specific) groups are independently disclosed herein. These substituent halogens, substituent hydrocarbyl groups, and substituent hydrocarboxy groups can be utilized without limitation to further describe a substituted cycloalkyl group (general or specific) which can be utilized as $R^1$.

In a non-limiting aspect, $R^1$ can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further describe alkylcyclohexyl groups (general and specific), dialkylcyclohexyl groups (general and specific), alkylcyclopentyl groups (general or specific), and/or dialkylcyclopentyl groups (general and specific) which can be utilized as $R^1$. Generally, the alkyl substituents of a dialkylcyclohexyl group or a dialkylcyclopentyl group can be the same; or alternatively, the alkyl substituents of a dialkylcyclohexyl group or a dialkylcyclopentyl group can be different. In some non-limiting aspects, $R^1$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^1$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, $R^1$ can be a phenyl group, a substituted phenyl group; alternatively, a phenyl group; or alternatively, a substituted phenyl group. In an aspect, the substituted phenyl group, which can be utilized as $R^1$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; or alternatively, a 2,4,6-trisubstituted phenyl group. In an aspect, one or more substituents of a multi-substituted phenyl group utilized as $R^1$ can be the same or different, alternatively, all the substituents of a multi-substituted cycloalkyl group can be the same; or alternatively, all the substituents of a multi-substituted cycloalkyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^1$.

In a non-limiting aspect, $R^1$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^1$. Generally, the alkyl substituents of a dialkylphenyl group (general or specific) or a trialkylphenyl group (general or specific) can be the same; or alternatively, the alkyl substituents of a dialkylphenyl group or trialkylphenyl group can be different. In some non-limiting aspects, $R^1$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In an aspect, $R^1$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group: alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group (general or specific) which can be utilized as $R^1$.

Generally, $R^2$ of the $N^2$-phosphinyl amidines and/or the $N^2$-phosphinyl amidine transition metal compound complexes can be an organyl group; alternatively, an organyl group consisting of inert functional groups; or alternatively, a hydrocarbyl group. In an aspect, the $R^2$ organyl group can be a $C_1$ to $C_{20}$, a $C_1$ to $C_{15}$, a $C_1$ to $C_{10}$, or a $C_1$ to $C_5$ organyl group. In an aspect, $R^2$ organyl group consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, $R^2$ hydrocarbyl group can be a $C_1$ to $C_{20}$, a $C_1$ to $C_{15}$, a $C_1$ to $C_{10}$, or a $C_1$ to $C_5$ hydrocarbyl group.

In an aspect, $R^2$ of the $N^2$-phosphinyl amidines and/or the $N^2$-phosphinyl amidine transition metal compound complexes can be an acyl group or a substituted acyl group; an acyl group; or alternatively, a substituted acyl group. In an aspect, the acyl group can be a $C_1$ to $C_{20}$, a $C_1$ to $C_{15}$, a $C_1$ to $C_{10}$, or a $C_1$ to $C_5$ acyl group. In an aspect, the substituted acyl group can be a $C_1$ to $C_{20}$, a $C_1$ to $C_{15}$, a $C_1$ to $C_{10}$, or a $C_1$ to $C_5$ a substituted acyl group. In some aspects, $R^2$ of the $N^2$-phosphinyl amidines and/or the $N^2$-phosphinyl amidine transition metal compound complexes can be an alkanoyl group, a substituted alkanoyl group, a benzoyl group, or a substituted benzoyl group; alternatively, an alkanoyl group or a substituted alkanoyl group; alternatively, a benzoyl group, or a substituted benzoyl group; alternatively, an alkanoyl group; alternatively, a substituted alkanoyl group; alternatively, a benzoyl group; or alternatively, a substituted benzoyl group. In any aspect disclosed herein, the $R^2$ alkanoyl group can be a $C_1$ to $C_{20}$, a $C_1$ to $C_{10}$, or a $C_1$ to $C_5$ alkanoyl group. In any aspect disclosed herein, the $R^2$ substituted alkanoyl group can be a $C_1$ to $C_{20}$, a $C_1$ to $C_{10}$, or a $C_1$ to $C_5$ substituted $R^2$ alkanoyl group. In any aspect disclosed herein, the $R^2$ benzoyl group can be a $C_7$ to $C_{20}$, a $C_7$ to $C_{15}$, or a $C_7$ to $C_{10}$ benzoyl group. In any aspect disclosed herein, the $R^2$ substituted benzoyl group can be a $C_7$ to $C_{20}$, a $C_1$ to $C_{15}$, or a $C_1$ to $C_{10}$ substituted $R^2$ benzoyl group. Each substituent of a substituted alkanoyl group (general or specific), and/or substituted benzoyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe substituted alkanoyl groups and/or substituted benzoyl group which can be utilized as $R^2$.

In an aspect, $R^2$ of the $N^2$-phosphinyl amidines and/or the $N^2$-phosphinyl amidine transition metal compound complexes can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, $R^2$ of the $N^2$-phosphinyl amidine and/or the $N^2$-phosphinyl amidine transition metal compound complexes can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the $R^2$ alkyl group can be a $C_1$ to $C_{20}$, a $C_1$ to $C_{10}$, or a $C_1$ to $C_5$ alkyl group. In any aspect disclosed herein, the $R^2$ substituted alkyl group can be a $C_1$ to $C_{20}$, a $C_1$ to $C_{10}$, or a $C_1$ to $C_5$ substituted alkyl group. In any aspect disclosed herein, the $R^2$ cycloalkyl group can be a $C_4$ to $C_{20}$, a $C_4$ to $C_{15}$, or a $C_4$ to $C_{10}$ cycloalkyl group. In any aspect disclosed herein, the $R^2$ substituted cycloalkyl group can be a $C_4$ to $C_{20}$, a $C_4$ to $C_{15}$, or a $C_4$ to $C_{10}$ substituted cycloalkyl group. In any aspect disclosed herein, the $R^2$ aryl group can be a $C_6$ to $C_{20}$, a $C_6$ to $C_{15}$, or a $C_6$ to $C_{10}$ aryl group. In any aspect disclosed herein, the $R^2$ substituted aryl group can be a $C_6$ to $C_{20}$, a $C_6$ to $C_{15}$, or a $C_6$ to $C_{10}$ substituted aryl group. In any aspect disclosed herein, the $R^2$ aralkyl group can be a $C_7$ to $C_{20}$, a $C_7$ to $C_{15}$, or a $C_7$ to $C_{10}$ aralkyl group. In any aspect disclosed herein, the $R^2$ substituted aryl group can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^2$.

In an aspect, $R^2$ can be a methyl group, an ethyl group, a propyl group, a butyl group, a pentyl group, a hexyl group, a heptyl group, or an octyl group; or alternatively, a methyl group, an ethyl group, an n-propyl (1-propyl) group, an iso-propyl (2-propyl) group, a tert-butyl (2-methyl-2-propyl) group, or a neopentyl (2,2-dimethyl-1-propyl) group. In some aspects, the alkyl groups which can be utilized as $R^2$ can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group (general or specific) which can be utilized as $R^2$.

In an aspect, $R^2$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group. In an aspect, the substituted cycloalkyl group, which can be utilized as $R^2$, can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect, one or more substituents of a multi-substituted cycloalkyl group utilized as $R^2$ can be the same or different; alternatively, all the substituents of a multi-substituted cycloalkyl group can be the same; or alternatively, all the substituents of a multi-substituted cycloalkyl group can be different. Each substituent of a cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^2$.

In a non-limiting aspect. $R^2$ can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^2$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting aspects. $R^2$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^2$ can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, $R^2$ can be a phenyl group, a substituted phenyl group; alternatively, a phenyl group; or alternatively, a substituted phenyl group. In an aspect, the substituted phenyl group, which can be utilized as $R^2$ can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; or alternatively, a 2,4,6-trisubstituted phenyl group. In an aspect, one or more substituents of a multi-substituted phenyl group utilized as $R^2$ can be the same or different; alternatively, all the substituents of a multi-substituted cycloalkyl group can be the same; or alternatively, all the substituents of a multi-substituted cycloalkyl group can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^2$.

In a non-limiting aspect, $R^2$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^2$. Generally, the alkyl substituents of a dialkylphenyl group (general or specific) or trialkylphenyl group (general or specific) can be the same; or alternatively, the alkyl substituents of a dialkylphenyl group or trialkylphenyl group can be different. In some non-limiting aspects, $R^2$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting aspect, $R^2$ can be a phenyl group, a 2-alkoxyphenyl group, or a 4-alkoxyphenyl group. In some non-limiting aspects, $R^2$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group. In another non-limiting aspect, $R^2$ can be a phenyl group, a 2-halophenyl group, a 4-halophenyl group, or a 2,6-dihalophenyl group. Generally, the halides of a dihalophenyl group can be the same; or alternatively, the halides of a dihalophenyl group can be different. In some aspects, $R^2$ can be a phenyl group, a 2-fluorophenyl group, a 4-fluorophenyl group, or a 2,6-difluorophenyl group.

In an aspect, $R^2$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group which can be utilized as $R^2$.

In further aspects. $R^1$ and $R^2$ can be joined to form a ring or a ring system containing the carbon-nitrogen double bond of the $N^2$-phosphinyl amidines and/or the $N^2$-phosphinyl amidine transition metal compound complexes. The joining of $R^1$ and $R^2$ can be designated as $L^{12r}$ and can be an organylene group; alternatively, an organylene group consisting of inert functional groups; alternatively, a hydrocarbylene group; or alternatively, an alkylene group. In an aspect, the $L^{12r}$ organylene group, when present, can be a $C_3$ to $C_{30}$, a $C_3$ to $C_{20}$, a $C_3$ to $C_{15}$, or a $C_3$ to $C_{10}$ organylene group. In some aspects, the $L^{12r}$ organylene group consisting of inert functional groups, when present, can be a $C_3$ to $C_{30}$, a $C_3$ to $C_{20}$, a $C_3$ to $C_{15}$, or a $C_3$ to $C_{10}$ organylene group consisting of inert functional groups. In other aspects, the $L^{12r}$ hydrocarbyl group, when present, independently can be a $C_3$ to $C_{30}$, a $C_3$ to $C_{20}$, a $C_3$ to $C_{15}$, or a $C_3$ to $C_{10}$ hydrocarbylene group. In a further aspect, the $L^{12r}$ alkylene group, when present, independently can be a $C_3$ to $C_{30}$, a $C_3$ to $C_{20}$, a $C_3$ to $C_{15}$, or a $C_3$ to $C_{10}$ alkylene group. In an aspect, $L^{12r}$ can be prop-1,3-ylene group, a but-1,3-ylene group, a 3-methylbut-1,3-ylene group ($-CH_2CH_2C(CH_3)_2-$), a but-1,4-ylene group, a 1,4-pent-1,4-ylene group.

Generally, T of the heterocyclic 2-[(phosphinyl)aminyl] imines and/or the heterocyclic 2-[(phosphinyl)aminyl]imine transition metal compound complexes can be oxygen or sulfur. In and aspect, T of the heterocyclic 2-[(phosphinyl)aminyl]imines and/or the heterocyclic 2-[(phosphinyl)aminyl]imine transition metal compound complexes can be oxygen; or alternatively, sulfur.

Generally, $R^{2a}$ and/or $R^{2b}$, of the $N^2$-phosphinyl guanidines and/or the $N^2$-phosphinyl guanidine transition metal compound complexes which have an $R^{2a}$ and/or $R^{2b}$ group, independently can be hydrogen or an organyl group; alternatively, hydrogen or an organyl group consisting of inert functional groups; alternatively, hydrogen or a hydrocarbyl group; alternatively, hydrogen; alternatively, an organyl group; alternatively, an organyl group consisting of inert functional groups, or alternatively, a hydrocarbyl group. In an aspect, the $R^{2a}$ and/or $R^{2b}$ organyl groups independently can be a $C_1$ to $C_{20}$, a $C_1$ to $C_{15}$, a $C_1$ to $C_{10}$, or a $C_1$ to $C_5$ organyl group. In some aspects, the $R^{2a}$ and/or $R^{2b}$ organyl groups consisting of inert functional groups independently can be a $C_1$ to $C_{20}$, a $C_1$ to $C_{15}$, a $C_1$ to $C_{10}$, or a $C_1$ to $C_5$ organyl group consisting of inert functional groups. In other aspects, the $R^{2a}$ and/or $R^{2b}$ hydrocarbyl groups independently can be a $C_1$ to $C_{20}$, a $C_1$ to $C_{15}$, a $C_1$ to $C_{10}$, or a $C_1$ to $C_5$ hydrocarbyl group.

In an aspect, $R^{2a}$ and $R^{2b}$, of the $N^2$-phosphinyl guanidines and/or the $N^2$-phosphinyl guanidine transition metal compound complexes which have an $R^{2a}$ and/or $R^{2b}$ organyl group, independently can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; alternatively, an alkyl group, a cycloalkyl group, an aryl group, or an aralkyl group; alternatively, an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the $R^{2a}$ and/or $R^{2b}$ alkyl group independently can be $C_1$ to $C_{20}$, a $C_1$ to $C_{10}$, or a $C_1$ to $C_5$ alkyl group. In any aspect disclosed herein, the $R^{2a}$ and/or $R^{2b}$ cycloalkyl group independently can be a $C_4$ to $C_{20}$, a $C_4$ to $C_{15}$, or a $C_4$ to $C_{10}$ cycloalkyl group. In any aspect disclosed herein, the $R^{2a}$ and/or $R^{2b}$ substituted cycloalkyl group independently can be a $C_4$ to $C_{20}$, a $C_4$ to $C_{15}$, or a $C_4$ to $C_{10}$ substituted cycloalkyl group. In any aspect disclosed herein, the $R^{2a}$ and/or $R^{2b}$ aryl group independently can be a $C_6$ to $C_{20}$, a $C_6$ to $C_{15}$, or a $C_6$ to $C_{10}$ aryl group. In any aspect disclosed herein, the $R^{2a}$ and/or $R^{2b}$ substituted aryl group independently can be a $C_6$ to $C_{20}$, a $C_6$ to $C_{15}$, or a $C_6$ to $C_{10}$ substituted aryl group. Each substituent of a substituted cycloalkyl group (general or specific) and/or a substituted aryl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^{2a}$ and/or $R^{2b}$.

In an aspect, $R^1$ and $R^2$ of the $N^2$-phosphinyl guanidines and/or the $N^2$-phosphinyl guanidine transition metal compound complexes can be joined to form a group, $L^{12}$, wherein $L^{12}$, the $N^1$ nitrogen atom, and the $N^3$ nitrogen atom form a ring or a ring system. In another aspect. $R^3$ and $R^{2b}$ of the $N^2$-phosphinyl guanidines and/or the $N^2$-phosphinyl guanidine transition metal compound complexes can be joined to form a group, $L^{23}$, wherein $L^{23}$, the $N^2$ nitrogen atom, and the $N^3$ nitrogen atom form a ring or a ring system. In an aspect, $L^{12}$ and/or $L^{23}$, of the $N^2$-phosphinyl guanidines and/or the $N^2$-phosphinyl guanidine transition metal compound complexes which have an $L^{12}$ group and/or an $L^{23}$ group, independently can be an organylene group; alternatively, an organylene group consisting of inert functional groups; or alternatively, a hydrocarbylene group. The $L^{12}$ and/or $L^{23}$ organylene groups independently can be a $C_2$ to $C_{20}$, a $C_2$ to $C_{15}$, a $C_2$ to $C_{10}$, or a $C_2$ to $C_5$ organylene group. The $L^{12}$ and/or $L^{23}$ organylene groups consisting of inert functional groups independently can be a $C_2$ to $C_{20}$, a $C_2$ to $C_{15}$, a $C_2$ to $C_{10}$, or a $C_2$ to $C_5$ organylene group consisting of inert functional groups. The $L^{12}$ and/or $L^{23}$ hydrocarbylene groups can be a $C_2$ to $C_{20}$, a $C_2$ to $C_{15}$, a $C_2$ to $C_{10}$, or a $C_2$ to $C_5$ hydrocarbylene group.

In an aspect, $L^{12}$ of the $N^2$-phosphinyl guanidines, the $N^2$-phosphinyl guanidine transition metal compound complexes, the heterocyclic 2-[(phosphinyl)aminyl]imines and/or the heterocyclic 2-[(phosphinyl)aminyl]imine transition metal compound complexes which have an $L^{12}$ and $L^{23}$ of the $N^2$-phosphinyl guanidines and/or the $N^2$-phosphinyl guanidine transition metal compound complexes which have an $L^{23}$, can have any structure provided in Table 1. In some aspects, $L^{12}$ and/or $L^{23}$ can have Structure 1L, Structure 2L, Structure 3L, Structure 4L or Structure 5L. In some aspects, $L^{12}$ and/or $L^{23}$ can have Structure 2L or Structure 3L; alternatively, Structure 4L or Structure 5L. In other aspects, $L^{12}$ and/or $L^{23}$ can have Structure 1L; alternatively, Structure 2L; alternatively, Structure 3L; alternatively, Structure 4L; or alternatively, Structure 5L. In some $N^2$-phosphinyl guanidine and $N^2$-phosphinyl guanidine transition metal compound complex aspects, $L^{12}$ and/or $L^{23}$ can have Structure 6L. It should be noted that when $L^{12}$ or $L^{23}$ has Structure 6L the corresponding $R^{2b}$ or $R^{2a}$ is null because of the double bond link with the $N^3$ nitrogen atom of the $N^2$-phosphinyl guanidine and/or the $N^2$-phosphinyl guanidine transition metal compound complex.

TABLE 1

Structures for Linking Groups $L^{12}$ and/or $L^{23}$.

| —(CR$^{L1}$R$^{L2}$)$_m$— | —CR$^{L3}$R$^{L4}$—CR$^{L5}$R$^{L6}$— | —CR$^{L3}$R$^{L4}$—CR$^{L7}$R$^{L8}$—CR$^{L5}$R$^{L6}$— |
|---|---|---|
| Structure 1L | Structure 2L | Structure 3L |
| —CR$^{L11}$=CR$^{L12}$— | (ring structure with R$^{L23}$, R$^{L24}$, R$^{L25}$, R$^{L26}$) | =CR$^{L27}$—CR$^{L28}$=CR$^{L29}$ |
| Structure 4L | Structure 5L | Structure 6L |

Within the structures of Table 1, the undesignated valences of $L^{12}$ and/or $L^{23}$ represent the points at which $L^{12}$ and/or $L^{23}$, when present, attach to the respective nitrogen atoms of the $N^2$-phosphinyl guanidine and the $N^2$-phosphinyl guanidine transition metal compound complex. Additionally, with the structures of Table 1, the undesignated valences of $L^{12}$ represent the points at which $L^{12}$ attach to T and the respective nitrogen atom of the heterocyclic 2-[(phosphinyl)aminyl]imine and/or the heterocyclic 2-[(phosphinyl)aminyl]imine transition metal compound complex. Generally, m can be an integer ranging from 2 to 5. In further aspects, m can be 2 or 3; alternatively, m can be 2; or alternatively, m can be 3. $R^{L1}$ and $R^{L2}$ of the linking group having Structure 1L, $R^{L3}$, $R^{L4}$, $R^{L5}$, and $R^{L6}$ of the linking group having Structure 2L, $R^{L3}$, $R^{L4}$, $R^{L5}$, $R^{L6}$, $R^{L7}$, and $R^{L8}$, of the linking group having Structure 3L, $R^{L11}$ and $R^{L12}$ of the linking group having Structure 4L, $R^{L23}$, $R^{L24}$, $R^{L25}$, and $R^{L26}$ of the linking group having Structure 5L, $R^{L27}$, $R^{L28}$, and $R^{L29}$ of the linking group having Structure 6L independently can be a hydrogen or a non-hydrogen substituent group; or alternatively, hydrogen. Non-hydrogen substituent groups (general and specific) are independently disclosed herein and can be utilized without limitation to further describe the linking group having Structure 1L, Structure 2L, Structure 3L, Structure 4L, Structure 5L, and/or Structure 6L. In an aspect, $L^{12}$ and/or $L^{23}$ independently can be an eth-1,2-ylene group (—CH$_2$CH$_2$—), an ethen-1,2-ylene group (—CH=CH—), a prop-1,3-ylene group (—CH$_2$CH$_2$CH$_2$—), a 1-methylethen-1,2-ylene group (—C(CH$_3$)=CH—), a but-1,3-ylene group (—CH$_2$CH$_2$CH(CH)—), a 3-methylbut-1,3-ylene group (—CH$_2$CH$_2$C(CH)$_2$—), or a phen-1,2-ylene group. In some non-limiting aspects, L$^{12}$ and/or L$^{23}$ be an eth-1,2-ylene group (—CH$_2$CH$_2$—), a prop-1,3-ylene group (—CH$_2$CH$_2$CH$_2$—), a 1-methylethen-1,2-ylene group (—C(CH$_3$)=CH—), a but-1,3-ylene group (—CH$_2$CH$_2$CH(CH$_3$)—), or a 3-methylbut-1,3-ylene group (—CH$_2$CH$_2$C(CH$_3$)$_2$—); alternatively, an eth-1,2-ylene group (—CH$_2$CH$_2$—), an ethen-1,2-ylene group (—CH=CH—), a prop-1,3-ylene group (—CH$_2$CH$_2$CH$_2$—), or a phen-1,2-ylene group; alternatively, an eth-1,2-ylene group (—CH$_2$CH$_2$—) or a prop-1,3-ylene group (—CH$_2$CH$_2$CH$_2$—); alternatively, an ethen-1,2-ylene group (—CH=CH—) or a phen-1,2-ylene group.

In an aspect, L$^{12}$ can have a structure that can comprise at least one substituent located on the carbon atom attached to the N$^1$ nitrogen atom of the N$^2$-phosphinyl guanidine and/or the N$^2$-phosphinyl guanidine transition metal compound complex; alternatively, can comprise only one substituent located on the carbon atom attached to the N$^1$ nitrogen atom of the N$^2$-phosphinyl guanidine and/or the N$^2$-phosphinyl guanidine transition metal compound complex; or alternatively, can comprise two substituents located on the carbon atom attached to the N$^1$ nitrogen atom of the N$^2$-phosphinyl guanidine and/or the N$^2$-phosphinyl guanidine transition metal compound complex. In another aspect, L$^{12}$ can have a structure that can consist of one substituent located on the carbon atom attached to the N$^1$ nitrogen atom the N$^2$-phosphinyl guanidine and/or the N$^2$-phosphinyl guanidine transition metal compound complex; or alternatively, can consist of two substituents located on the carbon atom attached to the N$^1$ nitrogen atom of the N$^2$-phosphinyl guanidine and/or the N$^2$-phosphinyl guanidine transition metal compound complex.

In an aspect, R$^{2a}$ and R$^{2b}$ of the N$^2$-phosphinyl guanidines and/or the N$^2$-phosphinyl guanidine transition metal compound complexes can be joined to form a group, L$^{22}$, wherein R$^{2a}$, R$^{2b}$, and the N$^3$ nitrogen (or L$^{22}$ and the N$^3$ nitrogen) form a ring or ring system. In an aspect, L$^{22}$ of the N$^2$-phosphinyl guanidines and/or the N$^2$-phosphinyl guanidine transition metal compound complexes having an L$^{22}$ group can be an organylene group; alternatively, an organylene group consisting of inert functional groups; or alternatively, a hydrocarbylene group. The L$^{22}$ organylene group can be a C$_3$ to C$_{20}$, a C$_3$ to C$_{15}$, or a C$_3$ to C$_{10}$ organylene group. The L$^{22}$ organylene group consisting of inert functional groups can be a C$_3$ to C$_{20}$, a C$_3$ to C$_{15}$, or a C$_3$ to C$_{10}$ organylene group consisting of inert functional groups. The L$^{22}$ hydrocarbylene group can be a C$_4$ to C$_{20}$, a C$_4$ to C$_{15}$, or a C$_4$ to C$_{10}$ hydrocarbylene group.

In an aspect, L$^{22}$ can have any structure provided in Table 2. In some aspects, L$^{22}$ can have Structure 11L, Structure 12L, Structure 13L, Structure 14L, Structure 15L, or Structure 16L. In other aspects, L$^2$ can have Structure 11L; alternatively, Structure 12L; alternatively, Structure 13L; alternatively, Structure 14L; or alternatively, Structure 15L.

TABLE 2

Structures for Linking Groups L$^{22}$.

| | |
|---|---|
| —(CR$^{L31}$R$^{L32}$)$_n$— | Structure 11L |
| —CR$^{L41}$R$^{L42}$—CR$^{L45}$R$^{L46}$ CR$^{L47}$R$^{L48}$ CR$^{L43}$R$^{L44}$— | Structure 12L |
| —CR$^{L41}$R$^{L42}$—CR$^{L45}$R$^{L46}$—CR$^{L49}$R$^{L50}$—CR$^{L47}$R$^{L48}$—CR$^{L43}$R$^{L44}$— | Structure 13L |
| —CR$^{L41}$R$^{L42}$—CR$^{L45}$R$^{L46}$—O—CR$^{L47}$R$^{L48}$—CR$^{L43}$R$^{L44}$— | Structure 14L |
| —CR$^{L51}$=CR$^{L53}$—CR$^{L54}$=CR$^{L52}$— | Structure 15L |

Within the structures of Table 2, the undesignated valences represent the points at which L$^{22}$ of the N$^2$-phosphinyl guanidine and/or the N$^2$-phosphinyl guanidine transition metal compound complex, when present, attach to the N$^3$ nitrogen atom of the N$^2$-phosphinyl guanidine and/or the N$^2$-phosphinyl guanidine transition metal compound complex. Generally, n can be an integer ranging from 4 to 7. In further aspects, n can be 4 or 5; alternatively, n can be 4; or alternatively, n can be 5. R$^{L31}$ and R$^{L32}$ of the linking group having Structure 11L, R$^{L41}$, R$^{L42}$, R$^{L43}$, R$^{L44}$, R$^{L45}$, R$^{L46}$, R$^{L47}$, and R$^{L48}$ of the linking group having Structure 12L, R$^{L41}$, R$^{L42}$, R$^{L43}$, R$^{L44}$, R$^{L45}$, R$^{L46}$, R$^{L47}$, R$^{L48}$, R$^{L49}$, and R$^{L50}$ of the linking group having Structure 13L, R$^{L41}$, R$^{L42}$, R$^{L43}$, R$^{L44}$, R$^{L45}$, R$^{L46}$, R$^{L47}$, and R$^{L48}$ of the linking group having Structure 14L, and R$^{L41}$, R$^{L42}$, R$^{L43}$, R$^{L44}$, R$^{L45}$, R$^{L46}$, R$^{L47}$, and R$^{L48}$ of the linking group having Structure 15L independently can be a hydrogen or a non-hydrogen substituent group; alternatively, hydrogen. Non-hydrogen substituent groups are independently disclosed herein and can be utilized without limitation to further describe the linking group having Structure 11L, Structure 12L, Structure 13L, Structure 14L, and/or Structure 15L. In an aspect, L$^{22}$ can be a but-1,4-ylene group, a pent-1,4-ylene group, a pent-1,5-ylene group, a hex-2,5-ylene group, a hex-1,5-ylene group, a hept-2,5-ylene group, a buta-1,3-dien-1,4-ylene group, or a bis(eth-2-yl)ether group; or alternatively, a but-1,4-ylene group, a pent-1,5-ylene group, or a bis(eth-2-yl)ether group.

Generally, R$^3$ of the N$^2$-phosphinyl formamidines, the N$^2$-phosphinyl formamidine transition metal compound complexes, the N$^2$-phosphinyl amidines, the N$^2$-phosphinyl amidine transition metal compound complexes, the N$^2$-phosphinyl guanidines, the N$^2$-phosphinyl guanidine transition metal compound complexes, the heterocyclic 2-[(phosphinyl)aminyl]imines, and/or the heterocyclic 2-[(phosphinyl)aminyl]imine transition metal compound complexes which have an R$^3$ group can be hydrogen or an organyl group; hydrogen or an organyl group consisting of inert functional group; alternatively, hydrogen or a hydrocarbyl group; alternatively, hydrogen; alternatively, an organyl group; alternatively, an organyl group consisting of inert functional group; or alternatively, a hydrocarbyl group. In an aspect, the R$^3$ organyl group can be a C$_1$ to C$_{20}$, a C$_1$ to C$_{15}$, a C$_1$ to C$_{10}$, or a C$_1$ to C$_5$ organyl group. In an aspect, the R$^3$ organyl group consisting of inert functional groups can be a C$_1$ to C$_{20}$, a C$_1$ to C$_{15}$, a C$_1$ to C$_{10}$, or a C$_1$ to C$_5$ organyl group consisting of inert functional groups. In an aspect, the R$^3$ hydrocarbyl group can be a, a C$_1$ to C$_{20}$, a C$_1$ to C$_{15}$, a C$_1$ to C$_{10}$, or a C$_1$ to C$_5$ hydrocarbyl group. In other aspects, R$^3$ of the N$^2$-phosphinyl formamidine, the N$^2$-phosphinyl formamidine transition metal compound complexes, the N$^2$-phosphinyl amidines, the N$^2$-phosphinyl amidine transition metal compound complexes, the N$^2$-phosphinyl guanidines, the N$^2$-phosphinyl guanidine transition metal compound complexes, the heterocyclic 2-[(phosphinyl)aminyl] imines, and/or the heterocyclic 2-[(phosphinyl)aminyl] imine transition metal compound complexes which have an $R^3$ group can be a $C_1$ to $C_{30}$, a $C_1$ to $C_{20}$, a $C_1$ to $C_{15}$, a $C_1$ to $C_{10}$, or a $C_1$ to $C_5$ alkyl group. In yet other aspects, $R^3$ of the $N^2$-phosphinyl formamidine, the $N^2$-phosphinyl formamidine transition metal compound complexes, the $N^2$-phosphinyl amidines, the $N^2$-phosphinyl amidine transition metal compound complexes, the $N^2$-phosphinyl guanidines, the $N^2$-phosphinyl guanidine transition metal compound complexes, the heterocyclic 2-[(phosphinyl)aminyl]imines, and/or the heterocyclic 2-[(phosphinyl)aminyl]imine transition metal compound complexes can be a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. Substituent groups (general and specific) are provided herein and these substituent groups can be utilized to further describe the substituted phenyl groups which can be utilized as $R^3$ the $N^2$-phosphinyl formamidine, the $N^2$-phosphinyl formamidine transition metal compound complexes, the $N^2$-phosphinyl amidines, the $N^2$-phosphinyl amidine transition metal compound complexes, the $N^2$-phosphinyl guanidines, and/or the $N^2$-phosphinyl guanidine transition metal compound complexes having a non-hydrogen $R^3$ group.

Generally, $R^4$ and/or $R^5$ of the $N^2$-phosphinyl formamidines, the $N^2$-phosphinyl formamidine transition metal compound complexes, the $N^2$-phosphinyl amidines, the $N^2$-phosphinyl amidine transition metal compound complexes, the $N^2$-phosphinyl guanidines, the $N^2$-phosphinyl guanidine transition metal compound complexes, the heterocyclic 2-[(phosphinyl)aminyl]imines, and/or the heterocyclic 2-[(phosphinyl)aminyl]imine transition metal compound complexes independently can be an organyl group; alternatively, an organyl group consisting of inert functional groups, or alternatively, a hydrocarbyl group. In an aspect, the $R^4$ and/or $R^5$ organyl groups can be a $C_1$ to $C_{20}$, a $C_1$ to $C_{15}$, a $C_1$ to $C_{10}$, or a $C_1$ to $C_5$ organyl group. In an aspect, the $R^4$ and/or $R^5$ organyl groups consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, the $R^4$ and/or $R^5$ hydrocarbyl groups can be a, a $C_1$ to $C_{20}$, a $C_1$ to $C_{15}$, a $C_1$ to $C_{10}$, or a $C_1$ to $C_5$ hydrocarbyl group. In an aspect, $R^4$ and/or $R^5$ of the $N^2$-phosphinyl formamidine, the $N^2$-phosphinyl formamidine transition metal compound complexes, the $N^2$-phosphinyl amidines, the $N^2$-phosphinyl amidine transition metal compound complexes, the $N^2$-phosphinyl guanidines, the $N^2$-phosphinyl guanidine transition metal compound complexes, the heterocyclic 2-[(phosphinyl)aminyl]imines, and/or the heterocyclic 2-[(phosphinyl)aminyl]imine transition metal compound complexes independently can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; alternatively, an alkyl group, a cycloalkyl group, an aryl group, or an aralkyl group; alternatively, an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect disclosed herein, the $R^4$ and/or $R^5$ alkyl groups independently can be a $C_1$ to $C_{20}$, a $C_1$ to $C_{10}$, or a $C_1$ to $C_5$ alkyl group. In any aspect disclosed herein, the $R^4$ and/or $R^5$ substituted alkyl groups independently can be a $C_1$ to $C_{20}$, a $C_1$ to $C_{10}$, or $C_1$ to $C_5$ substituted alkyl group. In any aspect disclosed herein, the $R^4$ and/or $R^5$ cycloalkyl groups independently can be a $C_4$ to $C_{20}$, a $C_4$ to $C_{15}$, or a $C_4$ to $C_{10}$ cycloalkyl group. In any aspect disclosed herein, the $R^4$ and/or $R^5$ substituted cycloalkyl groups independently can be a $C_4$ to $C_{20}$, a $C_4$ to $C_{15}$, or a $C_4$ to $C_{10}$ substituted cycloalkyl group. In any aspect disclosed herein, the $R^4$ and/or $R^5$ aryl groups independently can be a $C_6$ to $C_{20}$, a $C_6$ to $C_{15}$, or a $C_6$ to $C_{10}$ aryl group. In any aspect disclosed herein, the $R^4$ and/or $R^5$ substituted aryl group independently can be a $C_6$ to $C_{20}$, a $C_6$ to $C_{15}$, or a $C_6$ to $C_{10}$ substituted aryl group. In any aspect disclosed herein, the $R^4$ and/or $R^5$ aralkyl groups independently can be a $C_7$ to $C_{20}$, a $C_1$ to $C_{15}$, or a $C_7$ to $C_{10}$ aralkyl group. In any aspect disclosed herein, the $R^4$ and/or $R^5$ substituted aryl groups independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^4$ and/or $R^5$.

In an aspect, $R^4$ and $R^5$ independently can be a methyl group, an ethyl group, a propyl group, a butyl group, a pentyl group, a hexyl group, a heptyl group, or an octyl group; or alternatively, a methyl group, an ethyl group, an n-propyl (1-propyl) group, an iso-propyl (2-propyl) group, a 2-methyl-1-propyl group, a tert-butyl (2-methyl-2-propyl) group, or a neopentyl (2,2-dimethyl-1-propyl) group. In some aspects, the alkyl groups which can be utilized as $R^4$ and/or $R^5$ can be substituted. Each substituent of a substituted alkyl group independently can be a halogen or a hydrocarboxy group; alternatively, a halogen; or alternatively, a hydrocarboxy group. Substituent halogens and substituent hydrocarboxy (general and specific) groups are independently disclosed herein. These substituent halogens and substituent hydrocarboxy groups can be utilized without limitation to further describe a substituted alkyl group which can be utilized as $R^4$ and/or $R^5$.

In an aspect, $R^4$ and $R^5$ independently can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group. In an aspect, the substituted cycloalkyl group, which can be utilized for $R^4$ and/or $R^5$, can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect where the substituted cycloalkyl group (general or specific) has more the one substituent, the substituents can be the same or different; alternatively, the same; or alternatively, different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^4$ and/or $R^5$.

In a non-limiting aspect. $R^4$ and $R^5$ independently can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further described alkylcyclohexyl groups (general or specific), dialkylcyclohexyl groups (general or specific), alkylcyclopentyl groups (general or specific), and/or dialkylcyclopentyl groups (general or specific) which can be utilized as $R^4$ and/or $R^5$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting aspects, $R^4$ and $R^5$ independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^4$ and $R^5$ independently can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, $R^4$ and $R^5$ independently can be a phenyl group, a substituted phenyl group; alternatively, a phenyl group; or alternatively, a substituted phenyl group. In an aspect, the substituted phenyl group, which can be utilized for $R^4$ and/or $R^5$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; or alternatively, a 2,4,6-trisubstituted phenyl group. In an aspect, one or more substituents of a multi-substituted phenyl group utilized as $R^4$ and/or $R^5$ can be the same or different; alternatively, all the substituents of a multi-substituted cycloalkyl group can be the same; or alternatively, all the substituents of a multi-substituted cycloalkyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^4$ and/or $R^5$.

Ina non-limiting aspect, $R^4$ and $R^5$ independently can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^4$ and/or $R^5$. Generally, the alkyl substituents of a dialkylphenyl group (general or specific) or a trialkylphenyl group (general or specific) can be the same; or alternatively, the alkyl substituents of a dialkylphenyl group (general or specific) or a trialkyl phenyl group (general or specific) can be different. In some non-limiting aspects, $R^4$ and $R^5$ independently can be a phenyl group, a 2-methylphenyl group, a 2-ethylphenyl group, a 2-n-propylphenyl group, a 2-isopropylphenyl group, a 2-tert-butylphenyl group, a 26-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting aspect, $R^4$ and $R^5$ can be a phenyl group, a 2-alkoxyphenyl group, or a 4-alkoxyphenyl group. In some non-limiting aspects, $R^4$ and/or $R^5$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group. In a non-limiting aspect. $R^4$ and R independently can be a phenyl group, a 2-halophenyl group, a 4-halophenyl group, or a 2,6-dihalophenyl group. Generally, the halides of a dihalophenyl group can be the same; or alternatively, the halides of a dihalophenyl group can be different. In some aspects, $R^4$ and $R^5$ independently can be a phenyl group, a 2-fluorophenyl group, a 4-fluorophenyl group, or a 2,6-difluorophenyl group.

In an aspect, $R^4$ and $R^5$ independently can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl which can be utilized as $R^4$ and/or $R^5$.

In further aspects, $R^4$ and $R^5$ can be joined to form a ring or a ring system containing the phosphorus atom. The joining of $R^4$ and $R^5$ can be designated as $L^{45}$ and can be an organylene group; alternatively, an organylene group consisting of inert functional groups, alternatively, a hydrocarbylene group; or alternatively, an alkylene group. In an aspect, the $L^{45}$ organylene group, when present, can be a $C_4$ to $C_{30}$, a $C_4$ to $C_{20}$, a $C_4$ to $C_{15}$, or a $C_4$ to $C_{10}$ organylene group. In an aspect, the $L^{45}$ organylene group consisting of inert functional groups, when present, can be a $C_4$ to $C_{30}$, a $C_4$ to $C_{20}$, a $C_4$ to $C_{15}$, or a $C_4$ to $C_{10}$ organylene group consisting of inert functional groups. In an aspect, the $L^{45}$ hydrocarbyl group, when present, independently can be a $C_4$ to $C_{30}$, a $C_4$ to $C_{20}$, a $C_4$ to $C_{15}$, or a $C_4$ to $C_{10}$ hydrocarbylene group. In a further aspect, the $L^{45}$ alkylene group, when present, independently can be a $C_4$ to $C_{30}$, a $C_4$ to $C_{20}$, a $C_4$ to $C_{15}$, or a $C_4$ to $C_{10}$ alkylene group. In an aspect, $L^{45}$ can be a but-1,4-ylene group, a 1,4-diphenylbut-1,4-ylene group, a 1,4-di(2-methylphenyl)but-1,4-ylene group, 1,4-di(4-methylphenyl)but-1,4-ylene group, 1,4-di(4-t-butylphenyl)but-1,4-ylene group, a 1,4-di(3,5-dimethylphenyl)but-1,4-ylene group, a pent-1,4-ylene group, a 1-phenylpenta-1,4-ylene group, a 4-phenylpenta-1,4-ylene group, a hex-2,5-ylene group, a 2,2'-biphenylene group, a 2,2'-(methandiyl)dipheylene group, or a 2,2'-(1,2-ethandiyl)diphenylene group.

In an aspect, the heteroatomic ligand or the heteroatomic ligand of the heteroatomic ligand transition metal compound complex can have the formula $(R^{1s})_m X^{1s}(L^{1s})X^{2s}(R^{2s})_n$ while the heteroatomic ligand transition metal compound complex can have the formula:

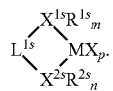

In some aspects, the heteroatomic ligand or the heteroatomic ligand of the heteroatomic ligand transition metal compound complex can have two groups capable of being described by the formula $(R^{1s})_m X^{1s}(L^{1s})X^{2s}(R^{2s})_n$. In instances wherein the heteroatomic ligand can have two groups capable of being described by the formula $(R^{1s})_m X^{1s}(L^{1s})X^{2s}(R^{2s})_n$, the two $L^{1s}$ groups are linked and the heteroatomic ligand and the heteroatomic ligand transition metal compound complex can have the formulas:

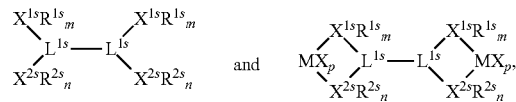

respectively.

In the heteroatomic ligand or the heteroatomic ligand of the heteroatomic ligand transition metal compound complex having formula $(R^{1s})_m X^{1s}(L^{1s})X^{2s}(R^{2s})_n$ or having two linked $(R^{1s})_m X^{1s}(L^{1s})X^{2s}(R^{2s})_n$ groups, each $X^{1s}$ and each $X^{2s}$ independently can be selected from the group consisting of N, P, O, and S; each $L^{1s}$ can be an independent linking group between the respective $X^{1s}$s and $X^{2s}$s; each m and each n independently can be 1 or 2; and each $R^{1s}$ and each $R^{2s}$ independently can be a hydrogen, an organyl group (or alternatively, an organyl group consisting of inert functional group; or alternatively, a hydrocarbyl group), or a heterohydrocarbyl group, where when there are two or more $R^{1s}$s and/or two $R^{2s}$s, each $R^{1s}$ can be the same or different (alternatively, the same; or alternatively, different) and/or each $R^{2s}$ can be the same or different (alternatively, the same; or alternatively, different). $L^{1s}$, $X^{1s}$, $X^{2s}$, $R^{1s}$, $R^{2s}$, m, and n are independent elements of any heteroatomic ligand or any heteroatomic ligand of the heteroatomic ligand transition metal compound complex which have an $L^{1s}$, $X^{1s}$, $X^{2s}$, $R^{1s}$, $R^{2s}$, m, and/or n and are independently described herein. These independent descriptions of $L^{1s}$, $X^{1s}$, $X^{2s}$, $R^{1s}$, $R^{2s}$, m, and n can be utilized without limitation, and in any combination, to further describe any heteroatomic ligand or any heteroatomic ligand of the heteroatomic ligand transition metal compound complex which have an $L^{1s}$, $X^{1s}$, $X^{2s}$, $R^{1s}$, $R^{2s}$, m, and/or n. Additionally, $CrX_p$ is an independent element of the heteroatomic ligand transition metal compound complex, and is independently described herein, and can be utilized without limitation, and in any combination with $L^{1s}$, $X^{1s}$, $X^{2s}$, $R^{1s}$, $R^{2s}$, m, and n of the heteroatomic ligand to further describe the heteroatomic ligand transition metal compound complexes contemplated herein.

In an aspect, each $X^{1s}$ and each $X^{2s}$ of any heteroatomic ligand or any heteroatomic ligand of any heteroatomic ligand transition metal compound complex described herein having an $X_{1s}$ and/or $X^{2s}$ can be independently selected from N, P, O, and S; alternatively, independently selected from N and P; or alternatively, independently selected from O and S. In some aspects, each $X^{1s}$ and each $X^{2s}$ can be N; alternatively, P; alternatively, O; or alternatively, S. Each m and each n of any heteroatomic ligand or any heteroatomic ligand of any heteroatomic ligand transition metal compound complex described herein having an m and/or n can be independently selected from 1 or 2; alternatively, 1; or alternatively, 2. Is some particular aspects, each m and/or each n can be 1 when $X^{1s}$ and/or $X^{2s}$, respectively, is O or S; alternatively, O; or alternatively, S. In some other particular aspects, each m and/or each n can be 2 when $X^{1s}$ and/or $X^{2s}$, respectively, is N or P; alternatively, N; or alternatively, P.

In a non-limiting aspect, the heteroatomic ligand can have the formula $R^{1s}S(L^{1s})SR^{2s}$, $(R^{1s})_2P(L^{1s})P(R^{2s})_2$, or $(R^{1s})_2N(L^{1s})N(R^{2s})_2$; alternatively, $R^{1s}S(L^{1s})SR^{2s}$; alternatively, $(R^{1s})_2P(L^{1s})P(R^{2s})_2$; or alternatively, $(R^{1s})_2N(L^{1s})N(R^{2s})_2$ while the heteroatomic ligand transition metal compound complex can have any one of the formulas

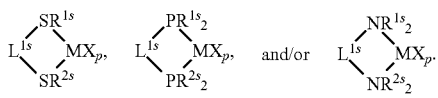

In non-limiting aspects where the heteroatomic ligand or the heteroatomic ligand of the heteroatomic ligand transition metal compound complex has two linked heteroatomic groups, the heteroatomic ligand can have the formula selected from one or more of

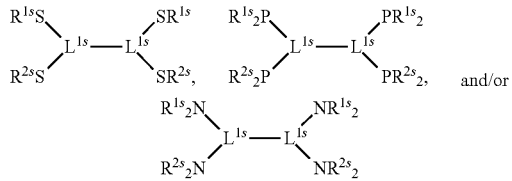

while the heteroatomic ligand transition metal compound complex can have any one of the formulas

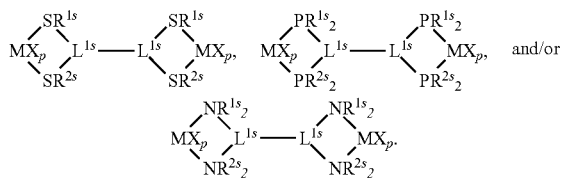

In an aspect, each $L^{1s}$ of any heteroatomic ligand or any heteroatomic ligand of the heteroatomic ligand transition metal compound complex described herein independently can be any group capable of linking group $X^{1s}$ and $X^{2s}$ (and other $L^{1s}$ group when the heteroatomic ligand or heteroatomic ligand of the heteroatomic ligand transition metal compound complex when there are more than one $L^{1s}$ group). In some aspects, each LIS independently can be an organylene group, an amin-di-yl group, or a phosphin-di-yl group; alternatively, an organylene group consisting of inert functional groups, an amin-di-yl group, or a phosphin-di-yl group; alternatively, a hydrocarbylene group, an amin-di-yl group, or a phosphin-di-yl group; alternatively an amin-di-yl group or a phosphin-di-yl group; alternatively, an organylene group; alternatively, an organylene group consisting of inert functional groups; alternatively, a hydrocarbylene group; alternatively, an amin-di-yl group; or alternatively, a phosphin-di-yl group. When there is more than one $L^{1s}$ group in the heteroatomic ligand or heteroatomic ligand of the heteroatomic ligand transition metal compound complex each $L^{1s}$ independently can be an organic, an amine group, or a phosphine group; alternatively, an organic group consisting of inert functional groups, an amine group, or a phosphine group; alternatively, a hydrocarbon group, an amine group, or a phosphine group; alternatively an amine group or a phosphine group; alternatively, an organic group; alternatively, an organic group consisting of inert functional groups; alternatively, a hydrocarbon group; alternatively, an amine group; or alternatively, a phosphine group. In an aspect, the $L^{1s}$ organylene group or organic group can be a $C_1$ to $C_{20}$, a $C_1$ to $C_{15}$, a $C_1$ to $C_{10}$, or, a $C_1$ to $C_5$ organylene or organic group. In an aspect, the $L^{1s}$ organylene group consisting of inert functional groups can be a $C_1$ to $C_{20}$, a $C_1$ to $C_{15}$, a $C_1$ to $C_{10}$, or, a $C_1$ to $C_5$ organylene or organic group consisting of inert functional groups. In an aspect, the $L^{1s}$ hydrocarbylene group can be a $C_1$ to $C_{20}$, a $C_1$ to $C_{15}$, a $C_1$ to $C_{10}$, or a $C_1$ to $C_5$ hydrocarbylene or hydrocarbon group. In an aspect, the amin-di-yl or amine group can be a $C_1$ to $C_{30}$, a $C_1$ to $C_{20}$, a $C_1$ to $C_{15}$, or a $C_1$ to $C_{10}$ amin-di-yl or amine group. In an aspect, the phosphin-di-yl or phosphine group can be a $C_1$ to $C_{30}$, a $C_1$ to $C_{20}$, a $C_1$ to $C_{15}$, or a $C_1$ to $C_{10}$ phosphin-di-yl or phosphine group.

In an aspect, each $L^{1s}$ organylene or organic group can have the formula $-(L^{3s})NR^{5s}(L^{4s})-$ or $-(L^{3s})PR^{5s}(L^{4s})-$; alternatively, $-(L^{3s})NR^{5s}(L^{4s})-$; or alternatively, $-(L^{3s})PR^{5s}(L^{4s})-$. In an aspect, the each amin-di-yl group can have the formula $-N(R^{5s})-$. In an aspect, each phosphin-di-yl group can have the formula $-P(R^{5s})-$. In these $L^{1s}$ group formulas, the dashes represent the undesignated valance to which the $X^{1s}$ and $X^{2s}$ of the heteroatomic ligand or the heteroatomic ligand of the heteroatomic ligand transition metal compound complex described herein attach. When there is more than one $L^{1s}$ group in the heteroatomic ligand or heteroatomic ligand of the heteroatomic ligand transition metal compound complex, the $R^{5s}$ of each $L_{1s}$ group can be combined into a linking group designated as $L^{2s}$. In some non-limiting aspects, the heteroatomic ligand can have Structure PNP1, Structure PNP2, Structure NRNRN, Structure PRPRP, Structure SRNRS, Structure PRNRP, and Structure NRPRN; alternatively, Structure PNP1 or Structure PNP2; alternatively, Structure PRPRP, Structure SRNRS, or Structure PRNRP; alternatively, Structure PNP; alternatively, Structure PNP2; alternatively, Structure NRNRN; alternatively, Structure PRPRP; alternatively, Structure SRNRS; alternatively, Structure PRNRP; or alternatively, Structure NRPRN. In some non-limiting aspects, the heteroatomic ligand transition metal compound complex having a heteroatomic ligand $(R^{1s})_m X^{1s}(L^{1s})X^{2s}(R^{2s})_n$, which can be utilized in catalyst systems described herein can have Structure PNPM1, Structure PNPM2, Structure NRNRNM1, Structure PRPRPCr1, Structure SRNRSM1, Structure PRNRPC-1r, and Structure NRPRNM1; alternatively, Structure PNPM1 or Structure PNPM2; alternatively, Structure PRPRPM1, Structure SRNRSM1, or Structure PRNRPC-1r; alternatively, Structure PNPM1; alternatively, Structure PNPM2; alternatively, Structure NRNRNC-1r; alternatively, Structure PRPRPM1; alternatively, Structure SRNRSM1; alternatively, Structure PRNRPM1; or alternatively, Structure NRPRNC-1r.

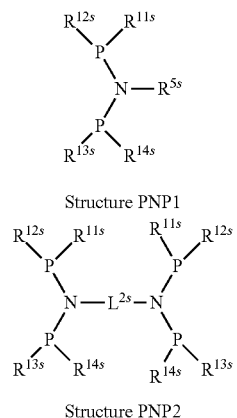

Structure PNP1

Structure PNP2

-continued

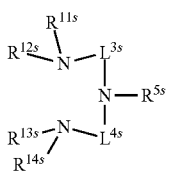

Structure NRNR1

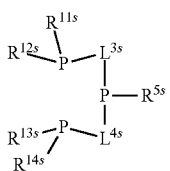

Structure NRNR1

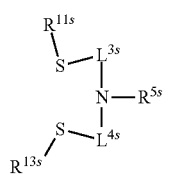

Structure SRNRS-1

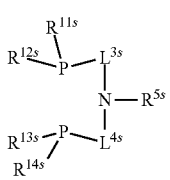

Structure PRNRP1

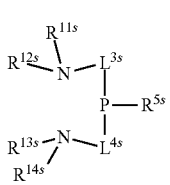

Structure NRPRN1

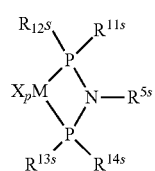

Structure PNPM1

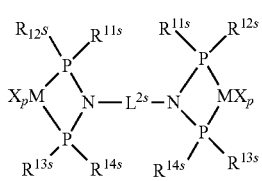

Structure PNPM2

-continued

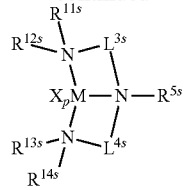

Structure NRNRNM1

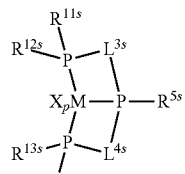

Structure PRPRPM1

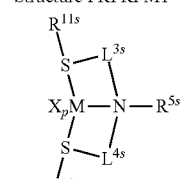

Structure PRPRPM1

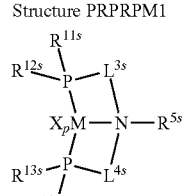

Structure PRNRPM1

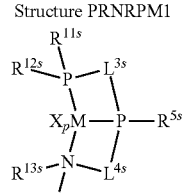

Structure NRPRNM1

The $R^{5s}$, $L^{2s}$, $L^{3s}$, $L^{4s}$, $R^{11s}$, $R^{12s}$, $R^{13s}$, and $R^{14s}$ are each independent elements of the heteroatomic ligands having Structure PNP1, Structure PNP2, Structure NRNRN1, Structure PRPRP1, Structure SRNRS1. Structure PRNRP1, or Structure NRPRN1, and/or the heteroatomic ligand of the heteroatomic ligand transition metal compound complexes having Structure PNPM1, Structure PNPM2, Structure NRNRNM1, Structure PRPRPM1, Structure SRNRSM1, Structure PRNRPM1, and Structure NRPRNM1 in which they occur and are independently described herein. The independent descriptions of $R^{5s}$, $L^{2s}$, $L^{3s}$, $L^{4s}$, $R^{11s}$, $R^{12s}$, $R^{13s}$, and $R^{14s}$ can be utilized without limitation, and in any combination, to further describe the heteroatomic ligand structures and/or the heteroatomic ligand transition metal compound complex structure in which they occur. Similarly, X and p are independent elements of the heteroatomic ligand transition metal compound complexes having Structure PNPM1, Structure PNPM2, Structure NRNRNM1, Structure PRPRPM1, Structure SRNRSM1, Structure PRNRPM1, and Structure NRPRNM1 and are independently described herein. The independent description of X and p can be utilized without limitation, and in any combination, with the independently described $R^{5s}$, $L^{2s}$, $L^{3s}$, $L^{4s}$, $R^{11s}$, $R^{12s}$, $R^{13s}$, and $R^{14s}$ provided herein to further describe any heteroatomic ligand transition metal compound complex having Structure PNPM1, Structure PNPM2, Structure NRNRNM1, Structure PRPRPM1, Structure SRNRSM1, Structure PRNRPM1, and/or Structure NRPRNM1.

Generally, $R^{1s}$, $R^{2s}$, $R^{11s}$, $R^{12s}$, $R^{13s}$, and/or $R^{14s}$, of any heteroatomic ligand structure depicted herein and/or any heteroatomic ligand transition metal compound complex depicted herein having an $R^{1s}$, $R^{2s}$, $R^{11s}$, $R^{12s}$, $R^{13s}$, and/or $R^{14s}$ group, independently can be an organyl group; alternatively, an organyl group consisting of inert functional groups; or alternatively, a hydrocarbyl group. In an aspect, the organyl group which can be utilized as $R^{1s}$, $R^{2s}$, $R^{11s}$, $R^{12s}$, $R^{13s}$, and/or $R^{14s}$ independently can be a $C_1$ to $C_{20}$, a $C_1$ to $C_{15}$, a $C_1$ to $C_{10}$, or a $C_1$ to $C_5$ organyl group. In an aspect, the organyl group consisting of inert functional groups which can be utilized as $R^{1s}$, $R^{2s}$, $R^{11s}$, $R^{12s}$, $R^{13s}$, and/or $R^{14s}$ independently can be a $C_1$ to $C_{20}$, a $C_1$ to $C_{15}$, a $C_1$ to $C_{10}$, or a $C_1$ to $C_5$ organyl group consisting of inert functional groups. In an aspect, the hydrocarbyl group which can be utilized as $R^{1s}$, $R^{2s}$, $R^{11s}$, $R^{12s}$, $R^{13s}$, and/or $R^{14s}$ independently can be a $C_1$ to $C_{20}$, a $C_1$ to $C_{15}$, a $C_1$ to $C_{10}$, or a $C_1$ to $C_5$ hydrocarbyl group.

In an aspect, each $R^{1s}$, $R^{2s}$, $R^{11s}$, $R^{12s}$, $R^{13s}$, and/or $R^{14s}$ of any heteroatomic ligand structure depicted herein and/or any heteroatomic ligand transition metal compound complex depicted herein having an $R^{1s}$, $R^{2s}$, $R^{11s}$, $R^{12s}$, $R^{13s}$, and/or $R^{14s}$ group independently can an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, each $R^{1s}$, $R^{2s}$, $R^{11s}$, $R^{12s}$, $R^{13s}$, and/or $R^{14s}$ of any heteroatomic ligand structure depicted herein and/or any heteroatomic ligand transition metal compound complex depicted herein having an $R^{1s}$, $R^{2s}$, $R^{11s}$, $R^{12s}$, $R^{13s}$, and/or $R^{14s}$ group independently can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect disclosed herein, each $R^{1s}$, $R^{2s}$, $R^{11s}$, $R^{12s}$, $R^{13s}$, and/or $R^{14s}$ alkyl group independently can be a $C_1$ to $C_{20}$, a $C_1$ to $C_{10}$, or a $C_1$ to $C_5$ alkyl group. In any aspect disclosed herein, each $R^{1s}$, $R^{2s}$, $R^{11s}$, $R^{12s}$, $R^{13s}$, and/or $R^{14s}$ substituted alkyl group independently can be a $C_1$ to $C_{20}$, a $C_1$ to $C_{10}$, or a $C_1$ to $C_5$ substituted alkyl group. In any aspect disclosed herein, each $R^{1s}$, $R^{2s}$, $R^{11s}$, $R^{12s}$, $R^{13s}$, and/or $R^{14s}$ cycloalkyl group independently can be a $C_4$ to $C_{20}$, a $C_4$ to $C_{15}$, or a $C_4$ to $C_{10}$ cycloalkyl group. In any aspect disclosed herein, each $R^{1s}$, $R^{2s}$, $R^{11s}$, $R^{12s}$, $R^{13s}$, and/or $R^{14s}$ substituted cycloalkyl group independently can be a $C_4$ to $C_{20}$, a $C_4$ to $C_{15}$, or a $C_4$ to $C_{10}$ substituted cycloalkyl group. In any aspect disclosed herein, each $R^{1s}$, $R^{2s}$, $R^{11s}$, $R^{12s}$, $R^{13s}$, and/or $R^{14s}$ aryl group independently can be a $C_6$ to $C_{20}$, a $C_6$ to $C_{15}$, or a $C_6$ to $C_{10}$ aryl group. In any aspect disclosed herein, each $R^{1s}$, $R^{2s}$, $R^{11s}$, $R^{12s}$, $R^{13s}$, and/or $R^{14s}$ substituted aryl group independently can be a $C_6$ to $C_{20}$, a $C_6$ to $C_{15}$, or a $C_6$ to $C_{10}$ substituted aryl group. In any aspect disclosed herein, each $R^{1s}$, $R^{2s}$, $R^{11s}$, $R^{12s}$, $R^{13s}$, and/or $R^{14s}$ aralkyl group independently can be a $C_7$ to $C_{20}$, a $C_7$ to $C_{15}$, or a $C_7$ to $C_{10}$ aralkyl group. In any aspect disclosed herein, each $R^{1s}$, $R^{2s}$, $R^{11s}$, $R^{12s}$, $R^{13s}$, and/or $R^{14s}$ substituted aralkyl group independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarboxy groups, and substituent hydrocarboxy groups can be utilized without limitation to further describe a substituted group (general or specific) which can be utilized $R^{1s}$, $R^{2s}$, $R^{11s}$, $R^{12s}$, $R^{13s}$, and/or $R^{14s}$.

In an aspect, each $R^{1s}$, $R^{2s}$, $R^{11s}$, $R^{12s}$, $R^{13s}$, and/or $R^{14s}$ independently can be a methyl group, an ethyl group, a propyl group, a butyl group, a pentyl group, a hexyl group, a heptyl group, or an octyl group; or alternatively, a methyl group, an ethyl group, an iso-propyl (2-propyl) group, a tert-butyl (2-methyl-2-propyl) group, or a neopentyl (2,2-dimethyl-1-propyl) group. In some aspects, the alkyl groups which can be utilized as each $R^{1s}$, $R^{2s}$, $R^{11s}$, $R^{12s}$, $R^{13s}$, and/or $R^{14s}$ independently can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group (general or specific) which can be utilized as $R^{1s}$, $R^{2s}$, $R^{11s}$, $R^{12s}$, $R^{13s}$, and/or $R^{14s}$.

In an aspect, each $R^{1s}$, $R^{2s}$, $R^{11s}$, $R^{12s}$, $R^{13s}$, and/or $R^{14s}$ independently can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an aspect, the substituted cycloalkyl group, which can be utilized for any of $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand transition metal compound complex described herein, any heteroatomic ligand formula or structure provided herein, and/or any heteroatomic ligand transition metal compound complex structure provided herein, independently can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect, one or more substituents of a multi-substituted cycloalkyl group utilized as $R^{1s}$, $R^{2s}$, $R^{11s}$, $R^{12s}$, $R^{13s}$, and/or $R^{14s}$ can be the same or different; alternatively, all the substituents of a multi-substituted cycloalkyl group can be the same; or alternatively, all the substituents of a multi-substituted cycloalkyl group can be different. Each substituent of a substituted cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^{1s}$, $R^{2s}$, $R^{11s}$, $R^{12s}$, $R^{13s}$, and/or $R^{14s}$.

In a non-limiting aspect, each $R^{1s}$, $R^{2s}$, $R^{11s}$, $R^{12s}$, $R^{13s}$, and/or $R^{14s}$ independently can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^{1s}$, $R^{2s}$, $R^{11s}$, $R^{12s}$, $R^{13s}$, and/or $R^{14}$. Generally, the alkyl substituents of a disubstituted cyclohexyl or cyclopentyl group can be the same, or alternatively, the alkyl substituents can be different. In some non-limiting aspects, each $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand transition metal compound complex described herein, any heteroatomic ligand formula or structure provided herein, and/or any heteroatomic ligand transition metal compound complex structure provided herein, independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, each $R^{1s}$, $R^{2s}$, $R^{11s}$, $R^{12s}$, $R^{13s}$, and/or $R^{14s}$ independently can be a phenyl group or a substituted phenyl group; alternatively, a phenyl group; or alternatively, a substituted phenyl group. In an aspect, the substituted phenyl group which can be utilized for each $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand transition metal compound complex described herein, any heteroatomic ligand formula or structure provided herein, and/or any heteroatomic ligand transition metal compound complex structure provided herein, independently can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an aspect, one or more substituents of a multi-substituted phenyl group utilized as $R^{1s}$, $R^{2s}$, $R^{11s}$, $R^{12s}$, $R^{13s}$, and/or $R^{14s}$ can be the same or different; alternatively, all the substituents can be the same; or alternatively, all the substituents can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy group can be utilized without limitation to further describe a substituted phenyl group (general or specific) which can be utilized as $R^{1s}$, $R^{2s}$, $R^{11s}$, $R^{12s}$, $R^{13s}$, and/or $R^{14s}$.

In a non-limiting aspect, each $R^{1s}$, $R^{2s}$, $R^{11s}$, $R^{12s}$, $R^{13s}$, and/or $R^{14s}$ independently can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^{1s}$, $R^{2s}$, $R^{11s}$, $R^{12s}$, $R^{13s}$, and/or $R^{14s}$. Generally, the alkyl substituents of dialkylphenyl groups (general or specific) or trialkylphenyl groups (general or specific) can be the same, or alternatively, the alkyl substituents can be different. In some non-limiting aspects, each $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand transition metal compound complex described herein, any heteroatomic ligand formula or structure provided herein, and/or any heteroatomic ligand transition metal compound complex structure provided herein, independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n- propylphenyl group, a 2-isopropylphenyl group, or a 2-tert-butylphenyl group; or alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting aspect, each $R^{1s}$, $R^{2s}$, $R^{11s}$, $R^{12s}$, $R^{13s}$, and/or $R^{14s}$ independently can be a phenyl group, a 2-alkoxyphenyl group, or a 4-alkoxyphenyl group. In some non-limiting aspects, each $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand transition metal compound complex described herein, any heteroatomic ligand formula or structure provided herein, and/or any heteroatomic ligand transition metal compound complex structure provided herein, independently can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group. In a non-limiting aspect, each $R^{1s}$, $R^{2s}$, $R^{11s}$, $R^{12s}$, $R^{13s}$, and/or $R^{14s}$ independently can be a phenyl group, a 2-halophenyl group, a 4-halophenyl group, or a 2,6-dihalophenyl group. Generally, the halides of a dihalophenyl group can be the same, or alternatively, the halides can be different. In some aspects, each $R^{1s}$, $R^{2s}$, $R^{11s}$, $R^{12s}$, $R^{13s}$, and/or $R^{14s}$ independently can be a phenyl group, a 2-fluorophenyl group, a 4-fluorophenyl group, or a 2,6-difluorophenyl group.

In an aspect, each $R^{1s}$, $R^{2s}$, $R^{11s}$, $R^{12s}$, $R^{13s}$, and/or $R^{14s}$ independently can be a benzyl group or a substituted benzyl group; alternatively, a benzyl group; or alternatively, a substituted benzyl group. Each substituent of a substituted benzyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group (general or specific) which can be utilized as $R^{1s}$, $R^{2s}$, $R^{11s}$, $R^{12s}$, $R^{13s}$, and/or $R^{14s}$.

In further aspects, two geminal RNs, two geminal $R^{2s}$s, geminal $R^{11s}$ and $R^{12s}$, and/or geminal $R^{13s}$ and $R^{14s}$ independently can be joined to form a ring or a ring system containing the heteroatom to which they are attached. The joining of two geminal $R^{1s}$s can be designated $L^{11s}$. The joining of two geminal $R^{2s}$s can be designated $L^{22s}$. The joining of geminal $R^{11s}$ and $R^{12s}$ can be designated $L^{12s}$. The joining of geminal $R^{13s}$ and $R^{14s}$ can be designated $L^{34s}$. In an aspect, $L^{11s}$, $L^{22s}$, $L^{12s}$, and/or $L^{34s}$ independently can be an organylene group; alternatively, an organylene group consisting of inert functional groups; alternatively, a hydrocarbylene group; or alternatively, an alkylene group. In an aspect, the $L^{11s}$, $L^{22s}$, $L^{12s}$, and/or $L^{34s}$ organylene group, when present, independently can be a $C_4$ to $C_{30}$, a $C_4$ to $C_{20}$, a $C_4$ to $C_{15}$, or a $C_4$ to $C_{10}$ organylene group. In some aspects, the $L^{11s}$, $L^{22s}$, $L^{12s}$, and/or $L^{34s}$ organylene group consisting of inert functional groups, when present, independently can be a $C_4$ to $C_{30}$, a $C_4$ to $C_{20}$, a $C_4$ to $C_{15}$, or a $C_4$ to $C_{10}$ organylene group consisting of inert functional groups. In other aspects, the $L^{11s}$, $L^{12s}$, $L^{12s}$, and/or $L^{34s}$ hydrocarbyl group, when present, independently can be a $C_4$ to $C_{30}$, a $C_4$ to $C_{20}$, a $C_4$ to $C_{15}$, or a $C_4$ to $C_{10}$ hydrocarbylene group. In a further aspect, the $L^{11s}$, $L^{12s}$, $L^{12s}$, and/or $L^{34s}$ alkylene group, when present, independently can be a $C_4$ to $C_{30}$, a $C_4$ to $C_{20}$, a $C_4$ to $C_{15}$, or a $C_4$ to $C_{10}$ alkylene group. In an aspect, $L^{12s}$ and/or $L^{34s}$, when present, independently can be a can be but-1,4-ylene group, a 1,4-diphenylbut-1,4-ylene group, a 1,4-di(2-methylphenyl)but-1,4-ylene group, 1,4-di(4-methylphenyl)but-1,4-ylene group, 1,4-di(4-t-butylphenyl)but-1,4-ylene group, a 1,4-di (3,5-dimethylphenyl)but-1,4-ylene group, a pent-1,4-ylene group, a 1-phenylpenta-1,4-ylene group, a 4-phenylpenta-1,4-ylene group, a hex-2,5-ylene group, a 2,2'-biphenylene group, a 2,2'-(methandiyl)diphenylene group, or a 2,2'-(1,2-ethandiyl)diphenylene group.

Generally, $R^{5s}$, of any heteroatomic ligand structure depicted herein and any heteroatomic ligand transition metal compound complex depicted herein having an $R^{5s}$ group, can be an organyl group; alternatively, an organyl group consisting of inert functional groups; or alternatively, a hydrocarbyl group. In an aspect, the $R^{5s}$ organyl group can be a $C_1$ to $C_{20}$, a $C_1$ to $C_{15}$, a $C_1$ to $C_{10}$, or a $C_1$ to $C_5$ organyl group. In an aspect, the $R^{5s}$ organyl group consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, the $R^{5s}$ hydrocarbyl group can be a $C_1$ to $C_{20}$, a $C_1$ to $C_{15}$, a $C_1$ to $C_{10}$, or a $C_1$ to $C_5$ hydrocarbyl group.

In an aspect, $R^{5s}$, of any heteroatomic ligand structure depicted herein and any heteroatomic ligand transition metal compound complex depicted herein having an $R^{5s}$ group, can be an alkyl group, a substituted alkyl group, a cycloalkyl group, a substituted cycloalkyl group, an aryl group, a substituted aryl group, an aralkyl group, or a substituted aralkyl group; can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, $R^{5s}$ of any heteroatomic ligand structure depicted herein and any heteroatomic ligand transition metal compound complex depicted herein having an $R^{5s}$ group, can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the $R^{5s}$ alkyl group can be a $C_1$ to $C_{20}$, a $C_1$ to $C_{15}$, or a $C_1$ to $C_{10}$ alkyl group. In any aspect disclosed herein, the $R^{5s}$ substituted alkyl group can be a $C_1$ to $C_{20}$, a $C_1$ to $C_{15}$, or a $C_1$ to $C_{10}$ substituted alkyl group. In any aspect disclosed herein, the $R^{5s}$ cycloalkyl group can be a $C_4$ to $C_{20}$, a $C_4$ to $C_{15}$, or a $C_4$ to $C_{10}$ cycloalkyl group. In any aspect disclosed herein, the $R^{5s}$ substituted cycloalkyl group can be a $C_4$ to $C_{20}$, a $C_4$ to, or a $C_4$ to $C_{10}$ substituted cycloalkyl group. In any aspect disclosed herein, the $R^{5s}$ aryl group can be a $C_6$ to $C_{20}$, a $C_6$ to $C_{15}$, or a $C_6$ to $C_{10}$ aryl group. In any aspect disclosed herein, the $R^{5s}$ substituted aryl group can be a $C_6$ to $C_{20}$, a $C_6$ to $C_{15}$, or a $C_6$ to $C_{10}$ substituted aryl group. In any aspect disclosed herein, the $R^{5s}$ aralkyl group can be a $C_7$ to $C_{20}$, a $C_7$ to $C_{15}$, or a $C_7$ to $C_{10}$ aralkyl group. In any aspect disclosed herein, the $R^{5s}$ substituted aralkyl group can be a $C_7$ to $C_{20}$, a $C_7$ to $C_{15}$, or a $C_7$ to $C_{10}$ substituted aralkyl group. Each substituent of a substituted alkyl group (general or specific), substituted cycloalkyl group (general or specific), substituted aryl group (general or specific), and/or substituted aralkyl group (general or specific) can be a halogen, hydrocarbyl group, or a hydrocarboxy group; alternatively, a halogen or a hydrocarbyl group; alternatively, a halogen or a hydrocarboxyl group; alternatively, a hydrocarbyl group or a hydrocarboxy group; alternatively, a halogen; alternatively, a hydrocarbyl group; or alternatively, a hydrocarboxy group. Substituent halogens, hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted group (general or specific) which can be utilized $R^{5s}$.

In an aspect, $R^{5s}$ can be a methyl group, an ethyl group, a propyl group, a butyl group, a pentyl group, a hexyl group, a heptyl group, or an octyl group; alternatively, a methyl group, an ethyl group, an n-propyl (1-propyl) group, an isopropyl (2-propyl) group, an n-butyl (1-butyl) group, a sec-butyl (2-butyl) group, an isobutyl (2-methyl-1-propyl) group, a tert-butyl (2-methyl-2-propyl) group, an n-pentyl (1-pentyl) group, a 2-pentyl group, a 3-pentyl group, a 2-methyl-1-butyl group, a tert-pentyl (2-methyl-2-butyl) group, a 3-methyl-1-butyl group, a 3-methyl-2-butyl group, or a neo-pentyl (2,2-dimethyl-1-propyl) group; or alternatively, a methyl group, an ethyl group, an iso-propyl (2-propyl) group, a tert-butyl (2-methyl-2-propyl) group, or a neopentyl (2,2-dimethyl-1-propyl) group. In some aspects, the $R^{5s}$ alkyl groups can be substituted. Each substituent of a $R^{5s}$ substituted alkyl group independently can be a halogen or a hydrocarboxy group; alternatively, a halogen; or alternatively, a hydrocarboxy group. Substituent halogens and substituent hydrocarboxy groups (general and specific) are independently described herein and these substituent groups can be utilized without limitation to further describe a substituted alkyl group (general or specific) which can be utilized as $R^{5s}$.

In an aspect, $R^{5s}$ can be a cyclopentyl group, a substituted cyclopentyl group, a cyclohexyl group, a substituted cyclohexyl group; alternatively, a cyclopentyl group or a substituted cyclopentyl group; or alternatively, a cyclohexyl group or a substituted cyclohexyl group. In further aspects. $R^{5s}$ can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect, one or more substituents of a multi-substituted cycloalkyl group utilized as R can be the same or different; alternatively, all the substituents of a multi-substituted cycloalkyl group can be the same; or alternatively, all the substituents of a multi-substituted cycloalkyl group can be different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently described herein and these substituent groups can be utilized without limitation to further describe a substituted cycloalkyl group (general or specific) which can be utilized as $R^{5s}$.

In a non-limiting aspect, $R^{5s}$ can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^{5s}$. Generally, the alkyl substituents of a disubstituted cyclohexyl or cyclopentyl group can be the same, or alternatively, the alkyl substituents can be different. In some non-limiting aspects, $R^{5s}$ heteroatomic ligand structure provided herein, and/or any heteroatomic ligand transition metal compound complex structure provided herein can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^{5s}$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group. In an aspect, R-heteroatomic ligand structure provided herein, and/or any heteroatomic ligand transition metal compound complex structure provided herein can be a cyclopentyl group, a 2-methylcyclopentyl group, a cyclohexyl group, or a 2-methylcyclohexyl group; alternatively, a cyclopentyl group or a cyclohexyl group; or alternatively, a 2-methylcyclopentyl group or a 2-methylcyclohexyl group.

In an aspect, $R^{5s}$ can be a phenyl group or a substituted phenyl group; alternatively, a phenyl group; or alternatively, a substituted phenyl group. In some aspects, $R^{5s}$ can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,4-disubstituted phenyl group or a 2,6-disubstituted phenyl group; alternatively, a 2-substituted phenyl group; alternatively, a 4-substituted phenyl group; alternatively, a 2,4-disubstituted phenyl group; alternatively, a 2,6-disubstituted phenyl group; or alternatively, a 2,4,6-trisubstituted phenyl group. In an aspect, one or more substituents of a multi-substituted phenyl group utilized as $R^{5s}$ can be the same or different; alternatively, all the substituents can be the same, or alternatively, all the substituents can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently described herein and these substituent groups can be utilized without limitation to further describe a substituted phenyl group (general or specific) which can be utilized as $R^{5s}$.

In a non-limiting aspect, $R^{5s}$ can be a phenyl group, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group, a 2,4-dialkylphenyl group, a 2,6-dialkylphenyl group, or a 2,4,6-trialkylphenyl group. Alkyl substituent groups (general and specific) are independently described herein and these alkyl substituent groups can be utilized, without limitation, to further describe any alkyl substituted phenyl group which can be utilized as $R^{5s}$. Generally, the alkyl substituents of dialkylphenyl groups (general of specific) or trialkylphenyl groups (general or specific) can be the same, or alternatively, the alkyl substituents can be different. In some non-limiting aspects, $R^{5s}$ can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2,6-dimethylphenyl group, or a 2,4,6-trimethylphenyl group.

Generally, $L^{2s}$, of any heteroatomic ligand and/or any heteroatomic ligand transition metal compound complex having an $L^{2s}$ group, can be an organylene group; alternatively, an organylene group consisting of inert functional groups; alternatively, a hydrocarbylene group; or alternatively, an alkylene group. In an aspect, the $L^{2s}$ organylene group can be a $C_1$ to $C_{20}$, a $C_1$ to $C_{15}$, or a $C_1$ to $C_{10}$ organylene group. In an aspect, the $L^{2s}$ organylene group consisting of inert functional groups can be a $C_1$ to $C_{20}$, a $C_1$ to $C_{15}$, or a $C_1$ to $C_{10}$ organylene group consisting of inert functional groups. In an aspect, the $L^{2s}$ alkylene group can be a $C_1$ to $C_{20}$, $C_1$ to $C_{15}$, or a $C_1$ to $C_{10}$ alkylene group.

In an aspect, $L^{2s}$ of any heteroatomic ligand and/or any heteroatomic ligand transition metal compound complex having an $L^{2s}$ group can be —$(CR^pR^{p'})_m$— where each $R^p$ and $R^{p'}$ can independently be hydrogen, methyl, ethyl, propyl, isopropyl, or butyl groups and m can be an integer from 1 to 12. In some aspects, $L^{2s}$ of any heteroatomic ligand and/or any heteroatomic ligand transition metal compound complex having an $L^{2s}$ group can be a methylene group (—CH$_2$—), an eth-1,2-ylene group (—CH$_2$CH$_2$—), a prop-1,3-ylene group (—CH$_2$CH$_2$CH$_2$—), a prop-1,2-ylene group (—CH(CH$_3$)CH$_2$—), a prop-2,2-ylene group (—C(CH$_3$)$_2$—) group, a but-1,4-ylene group (—CH$_2$CH$_2$CH$_2$CH$_2$), or a 2-methylprop-1,3-ylene group (—CH$_2$CH(CH$_3$)CH$_2$—); or alternatively a methylene group (—CH$_2$—), an eth-1,2-ylene group (—CH$_2$CH—), or a prop-1,2-ylene group (—CH(CH$_3$)CH$_2$).

In an aspect, $L^{2s}$ of any heteroatomic ligand and/or any heteroatomic ligand transition metal compound complex having an $L^{2s}$ group, can be 1,2-cyclohexylene, a substituted 1,2-cyclohexylene, 1,3-cyclohexylene, a substituted 1,3-cyclohexylene, 1,4-cyclohexylene, a substituted 1,4-cyclohexylene, 3,3'-bicyclohexylene, a substituted 3,3'-bicyclohexylene, 4,4'-bicyclohexylene, a substituted 4,4'-bicyclohexylene, bis(3-cyclohexylene)methane, a substituted bis(3-cyclohexylene)methane, bis(4-cyclohexylene)methane, a substituted bis(4-cyclohexylene)methane, 1,2-bis(3-cyclohexylene)ethane, a substituted 1,2-bis(3-cyclohexylene)ethane, 1,2-bis(4-cyclohexylene)ethane, a substituted 1,2-bis(4-cyclohexylene)ethane, 1,2-bis(3-cyclohexylene)propane, a substituted 1,2-bis(3-cyclohexylene)propane, 1,2-bis(4-cyclohexylene)propane, a substituted 1,2-bis(4-cyclohexylene)propane, 2,2-bis(3-cyclohexylene)-propane, a substituted 2,2-bis(3-cyclohexylene)propane, 2,2-bis(4-cyclohexylene)propane, or a substituted 2,2-bis(4-cyclohexylene)propane. In some aspects, $L^{2s}$ of any heteroatomic ligand and/or any heteroatomic ligand transition metal compound complex having an $L^{2s}$ group can be a substituted 1,2-cyclohexylene, a substituted 1,3-cyclohexylene, a substituted 1,4-cyclohexylene, a substituted 3,3'-bicyclohexylene, a substituted 4,4'-bicyclohexylene, a substituted bis(3-cyclohexylene)methane, a substituted bis(4-cyclohexylene)methane, a substituted 1,2-bis(3-cyclohexylene)ethane, a substituted 1,2-bis(4-cyclohexylene)ethane, a substituted 1,2-bis(3-cyclohexylene)propane, a substituted 1,2-bis(4-cyclohexylene)-propane, a substituted 2,2-bis(3-cyclohexylene)propane, or a substituted 2,2-bis(4-cyclohexylene)propane. In an aspect, each substituent of a substituted cyclohexylene, a substituted bis(cyclohexylene)methane, a substituted bis(cyclohexylene)ethane, or a substituted 1,2-bis(3-cyclohexylene)propane which can be utilized as $L^{2s}$ can be a hydrocarbyl group. Substituent groups (general and specific) are independently disclosed herein and can be utilized without limitation to further describe a substituted cyclohexylene (general or specific), a substituted bis(cyclohexylene)methane (general or specific), a substituted bis(cyclohexylene)ethane (general or specific), or a substituted 1,2-bis(3-cyclohexylene)propane (general or specific) which can be utilized as $L^{2s}$.

In an aspect, $L^{2s}$ of any heteroatomic ligand and/or any heteroatomic ligand transition metal compound complex having an $L^{2s}$ group can be 1,2-phenylene, a substituted 1,2-phenylene, 1,3-phenylene, a substituted 1,3-phenylene, 1,4-phenylene, a substituted 1,4-phenylene, 3,3'-biphenylene, a substituted 3,3'-biphenylene, 4,4'-biphenylene, a substituted 4,4'-biphenylene, bis(3-phenylene)methane, a substituted bis(3-phenylene)methane, bis(4-phenylene)methane, a substituted bis(4-phenylene)methane, 1,2-bis(3-phenylene)ethane, a substituted 1,2-bis(3-phenylene)ethane, 1,2-bis(4-phenylene)ethane, a substituted 1,2-bis(4-phenylene)ethane, 1,2-bis(3-phenylene)propane, a substituted 1,2-bis(3-phenylene)propane, 1,2-bis(4-phenylene)propane, a substituted 1,2-bis(4-phenylene)propane, 2,2-bis(3-phenylene)propane, a substituted 2,2-bis(3-phenylene)propane, 2,2-bis(4-phenylene)propane, or a substituted 2,2-bis(4-phenylene)propane. In some aspects, $L^{2s}$ of any heteroatomic ligand and/or any heteroatomic ligand transition metal compound complex having an $L^{2s}$ group can be a substituted 1,2-phenylene, a substituted 1,3-phenylene, a substituted 1,4-phenylene, a substituted 3,3'-biphenylene, a substituted 4,4'-biphenylene, a substituted bis(3-phenylene)methane, a substituted bis(4-phenylene)methane, a substituted 1,2-bis(3-phenylene)ethane, a substituted 1,2-bis(4-phenylene)ethane, a substituted 1,2-bis(3-phenylene)propane, a substituted 1,2-bis(4-phenylene)propane, a substituted 2,2-bis(3-phenylene)propane, or a substituted 2,2-bis(4-phenylene) propane. In an aspect, each substituent of a substituted phenylene (general or specific), a substituted biphenylene (general or specific), a substituted bis(phenylene)methane (general or specific), a substituted bis(phenylene)ethane (general or specific), and/or a substituted bis(phenylene) propane (general or specific) which can be utilized as $L^{2s}$ can be a hydrocarbyl group. Substituent hydrocarbyl groups (general and specific) are independently disclosed herein and can be utilized without limitation to further describe a substituted phenylene (general or specific), a substituted biphenylene (general or specific), a substituted bis(phenylene)methane (general or specific), a substituted bis(phenylene)ethane (general or specific), and/or a substituted bis (phenylene)propane (general or specific) which can be utilized as $L^{2s}$.

Generally, $L^{3s}$ and/or $L^{4s}$, of any heteroatomic ligand and/or any heteroatomic ligand transition metal compound complex having an $L^{3s}$ and/or $L^{4s}$ group, independently can be an organylene group; alternatively, an organylene group consisting of inert functional groups; alternatively, a hydrocarbylene group; alternatively, an alkylene group. In an aspect, the $L^{3s}$ and/or $L^{4s}$ organylene group independently can be a $C_1$ to $C_{20}$, a $C_1$ to $C_{15}$, or a $C_1$ to $C_{10}$ organylene group. In an aspect, the $L^{3s}$ and/or $L^{4s}$ organylene group consisting of inert functional groups independently can be a $C_1$ to $C_{20}$, a $C_1$ to $C_{15}$, or a $C_1$ to $C_{10}$ organylene group consisting of inert functional groups. In an aspect, the $L^{3s}$ and/or $L^{4s}$ hydrocarbylene group independently can be a $C_1$ to $C_{20}$, a $C_1$ to $C_{15}$, or a $C_1$ to $C_{10}$ hydrocarbylene group. In an aspect, the $L^{3s}$ and/or $L^{4s}$ alkylene group independently can be a $C_1$ to $C_{20}$, $C_1$ to $C_{15}$, or a $C_1$ to $C_{10}$ alkylene group.

In an aspect, $L^{3s}$ and/or $L^{4s}$ of any heteroatomic ligand structure and/or any heteroatomic ligand transition metal compound complex having an $L^{3s}$ and/or $L^{4s}$ group independently can be —(CR$^p$R$^{p'}$)$_m$— where each R$^p$ and R$^{p'}$ can independently be hydrogen, methyl, ethyl, propyl, isopropyl, or butyl groups and m can be an integer from 1 to 12. In some aspects, $L^{3s}$ and/or $L^{4s}$ of any heteroatomic ligand structure and/or any heteroatomic ligand transition metal compound complex having an $L^{3s}$ and/or $L^{4s}$ group independently can be a methylene group (—CH$_2$—), an eth-1, 2-ylene group (—CH$_2$CH$_2$—), an ethen-1,2-ylene group (—CH=CH—), a prop-1,3-ylene group (—CH$_2$CH$_2$CH$_2$—), a prop-1,2-ylene group (—CH(CH$_3$)CH$_2$—), a prop-2,2-ylene group (—C(CH$_3$)$_2$—), a 1-methylethen-1,2-ylene group (—C(CH$_3$)=CH—), a but-1,4-ylene group (—CH$_2$CH$_2$CH$_2$—CH$_2$—), a but-1,3-ylene group (—CH$_2$CH$_2$CH(CH$_3$)—), a but-2,3-ylene group (—CH(CH$_3$)CH(CH$_3$)—), a but-2-en-2,3-ylene group (—C(CH$_3$)C(CH$_3$)—), a 3-methylbut-1,3-ylene group (—CH$_2$CH$_2$C(CH$_3$)$_2$—), a 1,2-cyclopentylene group, a 1,2-cyclohexylene group, or a phen-1,2-ylene group; alternatively, a methylene group (—CH$_2$—), an eth-1,2-ylene group (—CH$_2$CH$_2$—), a prop-1,3-ylene group (—CH$_2$CH$_2$CH$_2$—), a prop-1,2-ylene group (—CH(CH$_3$)CH$_2$—), a prop-2,2-ylene group (—C(CH$_3$)$_2$—), a but-1,4-ylene group (—CH$_2$CH$_2$CH$_2$—CH$_2$—), a but-1,3-ylene group (—CH$_2$CH$_2$CH(CH$_3$)—), a but-2,3-ylene group (—CH(CH$_3$)CH(CH$_3$)—), a 1,2-cyclopentylene group, a 1,2-cyclohexylene group, or a phen-1,2-ylene group; or alternatively, an eth-1,2-ylene group (—CH$_2$CH—), a prop-1,3-ylene group (—CH$_2$CH$_2$CH$_2$—), a prop-1,2-ylene group (—CH(CH$_3$)CH$_2$—), a but-1,3-ylene group (—CH$_2$CH$_2$CH(CH$_3$)—), a but-2,3-ylene group (—CH(CH$_3$)CH(CH$_3$)—), a 1,2-cyclopentylene group, a 1,2-cyclohexylene group, or a phen-1,2-ylene group.

Generally, the transition metal of the heteroatomic ligand transition metal compound complex or the transition metal compound, MX$_p$, can be any transition metal atom. In an embodiment, the transition metal atom of the transition metal compound can comprise, or consist essentially of, a Group 3-12, a Group 4-10, a Group 6-9, or a Group 7-8 transition metal. In some embodiments, the transition metal atom of the transition metal compound can comprise, or consist essentially of, a Group 4 transition metal; alternatively, a Group 5 transition metal; alternatively, a Group 6 transition metal; alternatively, a Group 7 transition metal; alternatively, a Group 8 transition metal; alternatively, a Group 9 transition metal; or alternatively, a Group 10 transition metal. In an embodiment, the transition metal atom of the transition metal compound can comprise, or consist essentially of, titanium, zirconium, hafnium, vanadium, niobium, tantalum, chromium, molybdenum, tungsten, manganese, iron, cobalt, nickel, palladium, platinum, copper, or zinc; alternatively, titanium, zirconium, vanadium, chromium, molybdenum, tungsten, iron, cobalt, nickel, palladium, or platinum; alternatively, chromium, iron, cobalt, or nickel; alternatively, titanium, zirconium, or hafnium; alternatively, vanadium or niobium; alternatively, chromium, molybdenum, or tungsten; alternatively, iron or cobalt; or alternatively, nickel, palladium, platinum, copper, or zinc. In other embodiments, the metal salt can comprise titanium; alternatively, zirconium; alternatively, hafnium; alternatively, vanadium; alternatively, niobium; alternatively, tantalum; alternatively, chromium; alternatively, molybdenum; alternatively, tungsten; alternatively, manganese; alternatively, iron; alternatively, cobalt; alternatively, nickel; alternatively, palladium; alternatively, platinum; alternatively, copper; or alternatively, zinc. Generally, the transition metal atom of the heteroatomic ligand transition metal compound complex or the transition metal compound, MX$_p$, can have any positive oxidation state available to the transition metal atom. In an embodiment, the transition metal atom can have an oxidation state of from +2 to +6; alternatively, from +2 to +4; or alternatively, from +2 to +3. In some embodiments, the transition metal atom of the transition metal compound, MX$_p$, can have an oxidation state of +1; alternatively, +2; alternatively, +3; or alternatively, +4.

In an aspect, the transition metal of the heteroatomic ligand transition metal compound complex or the transition metal compound, MX$_p$ can be chromium, Cr. The chromium compound or the chromium compound of the heteroatomic ligand chromium compound complexes described herein can have formula CrX$_p$ where X represents a monoanionic ligand, and p represents the number of monoanionic ligands (and the oxidation state of the chromium in the chromium compound. The monoanionic ligand (X), and p are independent elements of the chromium compound or the chromium compound of the heteroatomic ligand chromium compound complexes described herein and are independently described herein. The independent descriptions of the monoanionic ligand (X), and p can be utilized without limitation, and in any combination, to further describe the chromium compound or the chromium compound of the heteroatomic ligand chromium compound complexes described herein. The chromium atom of the chromium compound (CrX$_p$) can have any positive oxidation state available to a chromium atom. In an aspect, the chromium atom can have an oxidation state of from +2 to +6; alternatively, from +2 to +4; or alternatively, from +2 to +3. In some aspects, the chromium atom of the chromium compound (CrX$_p$) can have an oxidation state of +1; alternatively, +2; alternatively, +3; or alternatively, +4.

The monoanion (X) of the transition metal compound can be any monoanion. In an aspect, the monoanion (X) can be a halide, a carboxylate, a β-diketonate, a hydrocarboxide, a nitrate, or a chlorate. In some aspects, the monoanion (X) can be a halide, a carboxylate, a β-diketonate, or a hydrocarboxide. In any aspect, the hydrocarboxide can be an alkoxide, an aryloxide, or an aralkoxide. Generally, hydrocarboxide (and subdivisions of hydrocarboxide) are the anion analogues of the hydrocarboxy group. In other aspects, the monoanion (X) can be a halide, a carboxylate, a β-diketonate, or an alkoxide; or alternatively, a halide or a β-diketonate. In other aspects, the monoanion (X) can be a halide; alternatively, a carboxylate; alternatively, a β-diketonate; alternatively, a hydrocarboxide; alternatively, an alkoxide; or alternatively, an aryloxide. Generally, when the heteroatomic ligand of the heteroatomic ligand transition metal compound complex is a neutral heteroatomic ligand the number of monoanions (p) can equal the oxidation state of the transition metal atom. When the heteroatomic ligand of the heteroatomic ligand transition metal compound complex is an anionic heteroatomic ligand the number of monoanions (p) can equal one less than the oxidation state of the transition metal atom. In an aspect, the number of monoanions can be from 2 to 6; alternatively, from 2 to 4; alternatively, from 2 to 3; alternatively, 1; alternatively, 2; alternatively, 3; or alternatively, 4.

Generally, each halide of the transition metal compound independently can be fluorine, chlorine, bromine, or iodine; or alternatively, chlorine, bromine, or iodine. In an aspect, each halide monoanion of the transition metal compound can be chlorine; alternatively, bromine; or alternatively, iodine.

Generally, each carboxylate of the transition metal compound independently can be a $C_1$ to $C_{20}$ carboxylate; or alternatively, a $C_1$ to $C_{10}$ carboxylate. In an aspect, each carboxylate of the transition metal compound independently can be acetate, a propionate, a butyrate, a pentanoate, a hexanoate, a heptanoate, an octanoate, a nonanoate, a decanoate, an undecanoate, or a dodecanoate; or alternatively, a pentanoate, a hexanoate, a heptanoate, an octanoate, a nonanoate, a decanoate, an undecanoate, or a dodecanoate. In some aspects, each carboxylate of the transition metal compound independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate); or alternatively, 2-ethylhexanoate. In some aspects, the carboxylate of the transition metal compound can be triflate (trifluoroacetate).

Generally, each β-diketonate of the transition metal compound independently can be any $C_1$ to $C_{20}$ a β-diketonate; or alternatively, any $C_1$ to $C_{10}$ β-diketonate. In an aspect, each β-diketonate of the chromium compound independently can be acetylacetonate (i.e., 2,4-pentanedionate), hexafluoroacetylacetonate (i.e., 1,1,1,5,5,5-hexafluoro-2,4-pentanedionate), or benzoylacetonate); alternatively, acetylacetonate; alternatively, hexafluoroacetylacetonate; or alternatively, benzoylacetonate.

Generally, each hydrocarboxide of the transition metal compound independently can be any $C_1$ to $C_{20}$ hydrocarboxide; or alternatively, any $C_1$ to $C_{20}$ hydrocarboxide. In an aspect, each hydrocarboxide of the transition metal compound independently can be a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide. In an aspect, each alkoxide of the transition metal compound independently can be methoxide, ethoxide, a propoxide, or a butoxide; alternatively, methoxide, ethoxide, isopropoxide, or tert-butoxide; alternatively, methoxide; alternatively, an ethoxide; alternatively, an iso-propoxide; or alternatively, a tert-butoxide. In an aspect, the aryloxide can be phenoxide.

In some aspects, the transition metal of the transition metal compound and/or the transition metal compound of the heteroatomic ligand transition metal compound complex can be chromium. When the transition metal is chromium the transition metal compound can be referred to as a chromium compound and the heteroatomic ligand transition metal compound complex of the catalyst systems described herein can be referred to as a heteroatomic ligand chromium compound complex. In an aspect where the transition metal is chromium, the heteroatomic ligand chromium compound complex of the catalyst system can be comprise an $N^2$-phosphinyl formamidine chromium compound complex, an $N^2$-phosphinyl amidine chromium compound complex, an $N^2$-phosphinyl guanidine chromium compound complex, or any combination thereof; alternatively, an $N^2$-phosphinyl formamidine chromium compound complex; alternatively, an $N^2$-phosphinyl amidine chromium compound complex; or alternatively, an $N^2$-phosphinyl guanidine chromium compound complex.

In an aspect, the $N^2$-phosphinyl formamidine chromium compound complex utilized in the catalyst systems described herein can have Structure NPFCr1. In an aspect, the $N^2$-phosphinyl amidine chromium compound complex can have Structure NPACr1. In an aspect, the $N^2$-phosphinyl guanidine chromium compound complex can have Structure GuCr1, GuCr2, GuCr3, GuCr4, or GuCr5; alternatively, Structure GuCr1; alternatively, Structure GuCr2; alternatively, Structure GuCr3; alternatively, Structure GuCr4; or alternatively, Structure GuCr5. In an aspect, the heterocyclic 2-[(phosphinyl)aminyl]imine transition metal compound complex can have Structure HCPACr1.

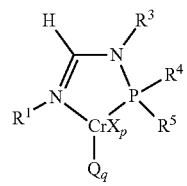 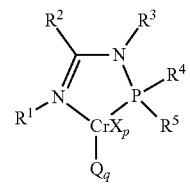

Structure NPFCr1  Structure NPACr1

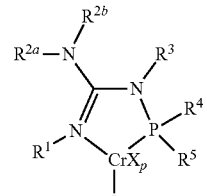 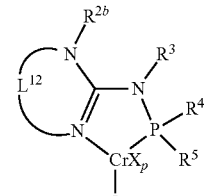

Structure GuCr1  Structure GuCr2

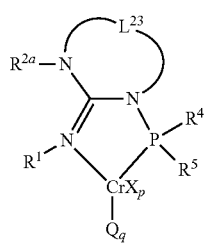 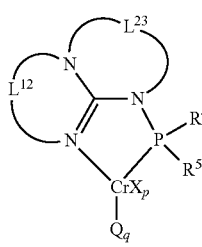

Structure GuCr3  Structure GuCr4

-continued

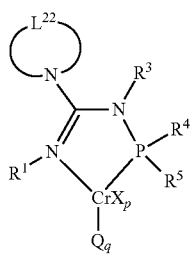
Structure GuCr5

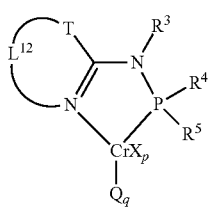
Structure HCPACrM1

Descriptions and options for $R^1$, $R^2$, $R^{2a}$, $R^{2b}$, $R^3$, $R^4$, $R^5$, $L^{12}$, $L^{22}$, $L^{23}$, X, p, Q, and q are independently described herein and these independent descriptions and options can be utilized without limitation and in any combination to further describe the $N^2$-phosphinyl formamidine chromium compound complexes, the $N^2$-phosphinyl amidine chromium compound complexes, the $N^2$-phosphinyl guanidine chromium compound complexes, and the heterocyclic 2-[(phosphinyl)aminyl]imine transition metal compound complexes contemplated by Structures NPFCr1, Structure NPACr1, Structure GuCr1, Structure GuCr2, Structure GuCr3, Structure GuCr4, Structure GuCr5, and/or Structure HCPACr1.

In another aspect where the transition metal is chromium, the transition metal compound can have any of one of the formulas

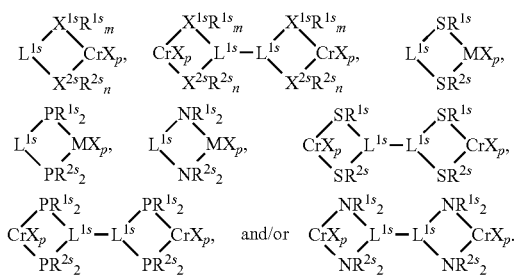

Descriptions and options for $R^{1s}$, $R^{2s}$, $X^{1s}$, $X^{2s}$, $L^{1s}$, m, n, X, and p, are independently described herein and these independent descriptions and options can be utilized without limitation and in any combination to further describe the heteroatomic ligand chromium compound complexes having the depicted formulas.

In further aspects where the transition metal is chromium, the transition metal compound can have Structure PNPCr1, Structure PNPCr2, Structure NRNCr1, Structure PRPCr1, Structure SRNCr1, Structure PRNCr1, and/or Structure NRPCr1.

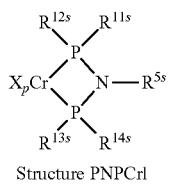
Structure PNPCr1

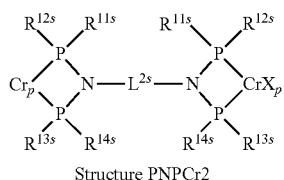
Structure PNPCr2

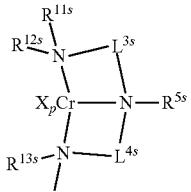
Structure NRNCr1

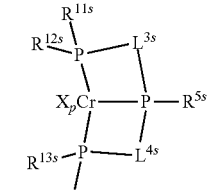
Structure PRPCr1

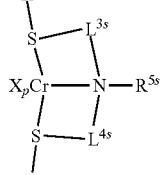
Structure SRNCr1

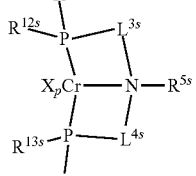
Structure PRNCr1

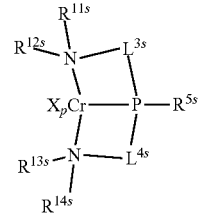
Structure NRPCr1

Descriptions and options for $R^{5s}$, $R^{11s}$, $R^{12s}$, $R^{13s}$, $R^{14s}$, $L^{2s}$, $L^{3s}$, $L^{4s}$, X, and p are independently described herein and these independent descriptions and options can be utilized without limitation and in any combination to further describe the heteroatomic ligand chromium compound complexes having Structure PNPCr1, Structure PNPCr2, Structure NRNCr1, Structure PRPCr1, Structure SRNCr1, Structure PRNCr1, and/or Structure NRPCr1.

In some non-limiting aspects, the chromium compound and/or the chromium compound of the heteroatomic ligand chromium compound complex can comprise, can consist essentially of, or consist of, a chromium(II) halide, a chromium(II) carboxylate, or a chromium(II) β-diketonate; or alternatively, a chromium(III) halide, a chromium(III) carboxylate, or a chromium(III) β-diketonate. In other non-limiting aspects, the chromium compound and/or the chromium compound of the heteroatomic ligand chromium compound complex can comprise, can consist essentially of or consist of, a chromium(II) halide; alternatively, a chromium(III) halide; alternatively, a chromium (II) carboxylate; alternatively, a chromium(III) carboxylate; alternatively, a chromium(II) β-diketonate; or alternatively, a chromium(III) β-diketonate. Halides, carboxylates, β-diketonates are independently described herein and these halides, carboxylates, β-diketonate and these independently described halides, carboxylates, β-diketonates can be utilized without limitation and in any combination to further described the chromium compound and/or the chromium compound of the heteroatomic ligand chromium compound complex. In further non-limiting aspects, the chromium compound and/or the chromium compound of the heteroatomic ligand chromium compound complex can comprise, can consist essentially of, or consist of, chromium(II) chloride, chromium(III) chloride, chromium(II) fluoride, chromium(III) fluoride, chromium(II) bromide, chromium(III) bromide, chromium (II) iodide, chromium(III) iodide, chromium(II) acetate, chromium(III) acetate, chromium(II) 2-ethylhexanoate, chromium(III) 2-ethylhexanoate, chromium(II) triflate, chromium(III) triflate, chromium(II) nitrate, chromium(III) nitrate, chromium(II) acetylacetonate, chromium(III) acetylacetonate, chromium(II) hexafluoracetylacetonate, chromium(III) hexafluoracetylacetonate, chromium(III) benzoylacetonate, or chromium(III) benzoylacetonate; alternatively, chromium(III) chloride, chromium(III) fluoride, chromium(III) bromide, chromium(III) iodide, chromium(III) chloride (THF) complex, chromium(III) acetate, chromium(III) 2-ethylhexanoate, chromium(III) triflate, chromium(III) nitrate, chromium(III) acetylacetonate, chromium(III) hexafluoracetylacetonate, or chromium(III) benzoylacetonate; alternatively, chromium(III) chloride, or chromium(III) acetylacetonate; alternatively, chromium(III) chloride; or alternatively, chromium(III) acetylacetonate.

In a non-limiting aspect, the heteroatomic ligand chromium compound complex can be selected from any one or more of a heteroatomic ligand chromium compound complex having i) Structure NPFCr1 where $R^1$ is 2,6-dimethylphenyl, $R^3$ is H, $R^4$ and $R^5$ are isopropyl, and X is chlorine; $R^1$ is 2,6-dimethylphenyl. $R^3$ is H, $R^4$ and $R^5$ are phenyl, and X is chlorine; $R^1$ is 2,6-dimethylphenyl, $R^3$ is H, $R^4$ and $R^5$ are 4-methoxyphenyl, and X is chlorine; $R^1$ is 2,4,6-trimethylphenyl, $R^3$ is H, $R^4$ and $R^5$ are isopropyl, and X is chlorine; $R^1$ is 2,4,6-trimethylphenyl, $R^3$ is H, $R^4$ and $R^5$ are phenyl, and X is chlorine; and $R^1$ is 2,4,6-trimethylphenyl, $R^3$ is H, $R^4$ and $R^5$ are 4-methoxyphenyl, and X is chlorine; ii) Structure NPACr1 where $R^1$ is 2,6-dimethylphenyl, $R^2$ is phenyl, $R^3$ is H, $R^4$ and $R^5$ are isopropyl, and X is chlorine; $R^1$ is 2,4,6-trimethylphenyl, $R^2$ is phenyl, $R^3$ is H, $R^4$ and $R^5$ are isopropyl, and X is chlorine; $R^1$ is 2,6-dimethylphenyl, $R^2$ is phenyl, $R^3$ is H, $R^4$ and $R^5$ are phenyl, and X is chlorine; $R^1$ is 2,4,6-trimethylphenyl, $R^2$ is phenyl, $R^3$ is H, $R^4$ and $R^5$ are phenyl, and X is chlorine; $R^1$ is 2,6-dimethylphenyl, $R^2$ is 4-methylbenzyl, $R^3$ is H, $R^4$ and $R^5$ are phenyl, and X is chlorine; $R^1$ is 2,6-dimethylphenyl, $R^2$ is phenyl, $R^3$ is H, $R^4$ and $R^5$ are 4-methoxyphenyl, and X is chlorine; $R^1$ is 2,6-dimethylphenyl, $R^2$ is 4-t-butylphenyl, $R^3$ is H, $R^4$ and $R^5$ are methyl, and X is chlorine; $R^1$ is 2,4,6-trimethylphenyl, $R^2$ is 4-t-butylphenyl, $R^3$ is H, $R^4$ and $R^5$ are methyl, and X is chlorine; $R^1$ is 2,4,6-trimethylphenyl, $R^2$ is 4-methylbenzyl, $R^3$ is H, $R^4$ and $R^5$ are isopropyl, and X is chlorine; $R^1$ is 2,4,6-trimethylphenyl, $R^2$ is 4-methylbenzyl, $R^3$ is H, $R^4$ and $R^5$ are phenyl, and X is chlorine; $R^1$ is 3,5-dimethylphenyl, $R^2$ is phenyl, $R^3$ is H, $R^4$ and $R^5$ are isopropyl, and X is chlorine; $R^1$ is 2,4,6-trimethylphenyl, $R^2$ is 4-methylbenzyl, $R^3$ is H, $R^4$ and $R^5$ are 4-methoxyphenyl, and X is chlorine; $R^1$ is 2,4,6-trimethylphenyl, $R^2$ is 4-methylbenzyl, $R^3$ is H, $R^4$ is t-butyl, $R^4$ is phenyl, and X is chlorine; $R^5$ is 2,4,6-trimethylphenyl, $R^2$ is 4-methylbenzyl, $R^3$ is H, $R^4$ is methyl, $R^5$ is phenyl, and X is chlorine; $R^1$ and $R^2$ are joined to form a prop-1,3-ylene group, $R^3$ is H, $R^4$ and $R^5$ are isopropyl, and X is chlorine; $R^1$ and $R^2$ are joined to form a but-1,4-ylene group, $R^3$ is H, $R^4$ and $R^5$ are isopropyl, and X is chlorine; $R^1$ is 2,4,6-trimethylphenyl, $R^2$ is 4-methylbenzyl, $R^3$ is H, $R^4$ and $R^5$ are joined to form a but-1,4-ylene group, and X is chlorine; $R^1$ is 2,4,6-trimethylphenyl, $R^2$ is 4-methylbenzyl, $R^3$ is H, $R^4$ and $R^5$ are joined to form a 2,2'-dimethylbiphenylene group, and X is chlorine; iii) Structure GUCr1 where $R^1$ is 2-methylphenyl, $R^{2a}$ is 2-methylphenyl, $R^{2b}$ is H, $R^3$ is H, $R^4$ and $R^5$ are isopropyl, and X is chlorine; $R_1$ is 2,6-dimethylphenyl, $R^{2a}$ is phenyl, $R^{2b}$ is H, $R^3$ is H, $R^4$ and $R^5$ are isopropyl, and X is chlorine; $R^1$ is 2,6-dimethylphenyl, $R^{2a}$ is phenyl, $R^{2b}$ is H, $R^3$ is H, $R^4$ and $R^5$ are phenyl, and X is chlorine; $R^1$ is 2,6-dimethylphenyl, $R^{2a}$ and $R^{2b}$ are phenyl, $R^3$ is H, $R^4$ and $R^5$ are isopropyl, and X is chlorine; iv) Structure GUCr4 where $L^{12}$ is prop-1,3-ylene, $L^{23}$ is prop-1,3-ylene, $R^4$ and $R^5$ are isopropyl, and X is chlorine; $L^{12}$ is prop-1,3-ylene, $L^{23}$ is prop-1,3-ylene, $R^4$ and $R^5$ are cyclopentyl, and X is chlorine; $L^{12}$ is prop-1,3-ylene, $L^{23}$ is prop-1,3-ylene, $R^4$ and $R^5$ are cyclohexyl, and X is chlorine; $L^{12}$ is prop-1,3-ylene, $L^{23}$ is prop-1,3-ylene, $R^4$ and $R^5$ are phenyl, and X is chlorine; $L^{12}$ is but-1,3-ylene, $L^{23}$ is prop-1,3-ylene, $R^4$ and $R^5$ are isopropyl, and X is chlorine; $L^{12}$ is but-1,3-ylene, $L^{23}$ is prop-1,3-ylene, $R^4$ and $R^5$ are cyclopentyl, and X is chlorine; $L^{12}$ is but-1,3-ylene, $L^{23}$ is but-1,3-ylene, $R^4$ and $R^5$ are isopropyl, and X is chlorine; $L^{12}$ is but-1,3-ylene, $L^{23}$ is but-1,3-ylene, $R^4$ and $R^5$ are phenyl, and X is chlorine; $L^{12}$ is ethen-1,2-ylene, $L^{23}$ is prop-1,3-ylene, $R^4$ and $R^5$ are isopropyl, and X is chlorine; $L^{12}$ is ethen-1,2-ylene, $L^{23}$ is prop-1,3-ylene, $R^4$ and $R^5$ are cyclopentyl, and X is chlorine; $L^{12}$ is ethen-1,2-ylene, $L^{23}$ is prop-1,3-ylene, $R^4$ and $R^5$ are cyclohexyl, and X is chlorine; $L^{12}$ is phen-1,2-ylene, $L^{23}$ is eth-1,2-ylene, $R^4$ and $R^5$ are isopropyl, and X is chlorine; and v) Structure HCPACr2 where T is sulfur, $L^{12}$ is ethen-1,2-ylene, $R^3$ is H, $R^4$ and $R^5$ are isopropyl, and X is chlorine; and T is sulfur, $L^{12}$ is phen-1,2-ylene, $R^3$ is H, $R^4$ and $R^5$ are isopropyl, and X is chlorine.

In another non-limiting aspect, the heteroatomic ligands for the heteroatomic ligand chromium compound complexes can be selected from any one or more of HL 1, HL 2, HL 3, HL 4, HL 5, HL 6, HL 7, HL 7, and HL 9. In other non-limiting aspects, the heteroatomic ligand chromium compound complexes can be selected from a diphosphino amine chromium compound complex of any one or more of HLCr 1, HLCr 2, HLCr 3, HLCr 4, HLCr 5, HLCr 6, HLCr 7, HLCr 8, and HLCr 9. In other non-limiting aspects, the heteroatomic ligand chromium compound complex can be selected from the chromium(III) chloride or chromium(III) acetylacetonate complex of a diphosphino amine chromium compound complex of any one or more of HLCr 1, HLCr 2, HLCr 3, HLCr 4, HLCr 5, HLCr 6, HLCr 7, HLCr 8, and HLCr 9.

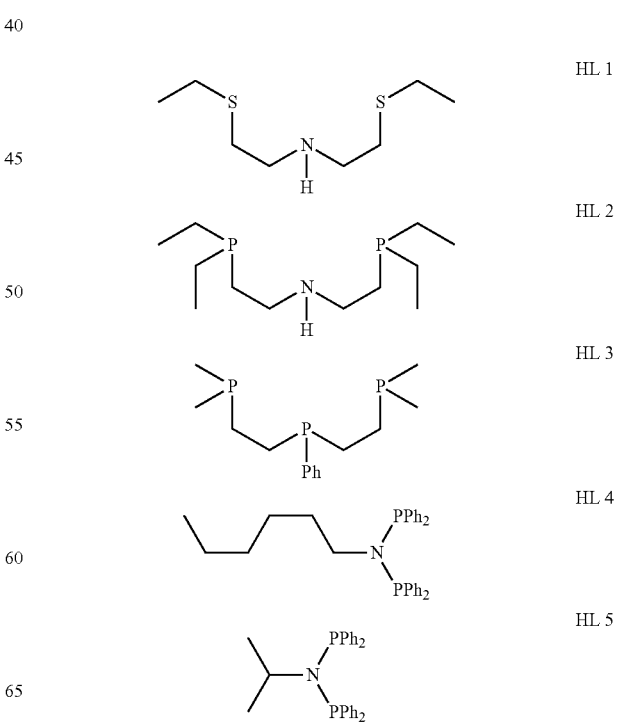

-continued

HL 6 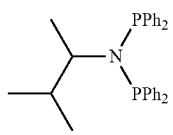

HL 7 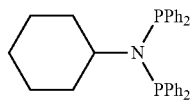

HL 8 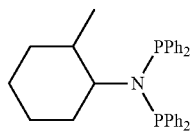

HL 9 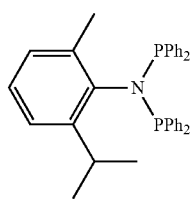

HLCr 1 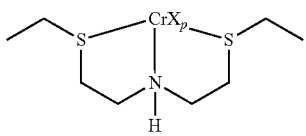

HLCr 2 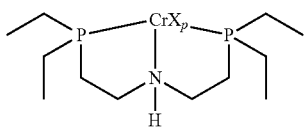

HLCr 3 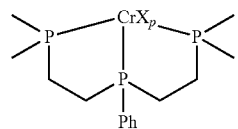

HLCr 4 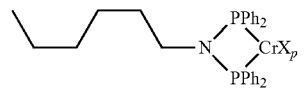

HLCr 5 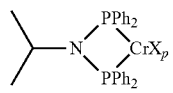

HLCr 6 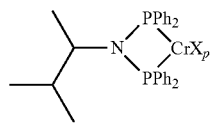

HLCr 7 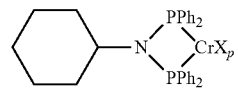

HLCr 8 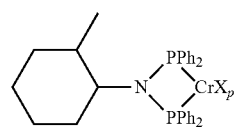

HLCr 9 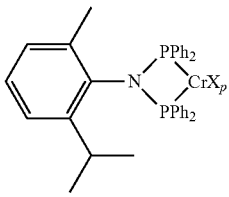

While not shown in all of the transition metal compound names and formulas, heteroatomic ligand transition metal compound complex formulas and structures, or the heteroatomic ligand chromium compound complex formulas and structures, one of ordinary skill in the art will recognize that a neutral ligand can be associated with the transition metal compounds, heteroatomic ligand transition metal compound complexes, and/or the heteroatomic ligand chromium compound complexes described/depicted herein which do not explicitly disclose/depict a neutral ligand. Additionally it should be understood that while some the transition metal compounds, heteroatomic ligand transition metal compound complexes, and/or the heteroatomic ligand chromium compound complexes described/depicted/provided herein do not formally show the presence of a neutral ligand, the transition metal compounds, heteroatomic ligand transition metal compound complexes, and/or the heteroatomic ligand chromium compound complexes having neural ligands (e.g., nitriles and ethers, among others) are implicitly and fully contemplated as potential the transition metal compounds, heteroatomic ligand transition metal compound complexes, and/or the heteroatomic ligand chromium compound complexes that can be utilized in the catalyst system used in aspects of the herein described inventions.

Generally, the neutral ligand of any transition metal compound, heteroatomic ligand transition metal compound complex, or heteroatomic ligand chromium compound complex, when present, independently can be any neutral ligand that forms an isolatable compound with the transition metal compound, heteroatomic ligand transition metal compound complex, or heteroatomic ligand chromium compound complex. In an aspect, each neutral ligand independently can be a nitrile or an ether; alternatively, a nitrile; or alternatively, an ether. The number of neutral ligands, q, can be any number that forms an isolatable compound with the transition metal compound, heteroatomic ligand transition metal compound complex, or heteroatomic ligand chromium compound complex. In an aspect, the number of neutral ligands can be from 0 to 6; alternatively, 0 to 3; alternatively, 0; alternatively, 1; alternatively, 2; alternatively, 3; or alternatively, 4.

Generally, each nitrile ligand independently can be a $C_2$ to $C_{20}$ nitrile; or alternatively, a $C_2$ to $C_{10}$ nitrile. In an aspect, each nitrile ligand independently can be a $C_2$ to $C_{20}$ aliphatic nitrile, a $C_7$ to $C_{20}$ aromatic nitrile, a $C_8$ to $C_{20}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_8$ to $C_{20}$ aralkane nitrile. In some aspects, each nitrile ligand independently can be a $C_2$ to $C_{10}$ aliphatic nitrile, a $C_7$ to $C_{10}$ aromatic nitrile, a $C_8$ to $C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_8$ to $C_{10}$ aralkane nitrile. In an aspect, each aliphatic nitrile independently can be acetonitrile, propionitrile, a butyronitrile, benzonitrile, or any combination thereof; alternatively, acetonitrile; alternatively, propionitrile; alternatively, a butyronitrile; or alternatively, benzonitrile.

Generally, each ether ligand independently can be a $C_2$ to $C_{40}$ ether; alternatively, a $C_2$ to $C_{30}$ ether; or alternatively, a $C_2$ to $C_{20}$ ether. In an aspect, each ether ligand independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some aspects, each ether ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other aspects, each ether ligand independently can be a $C_2$ to $C_{20}$ aliphatic ether, a $C_3$ to $C_{20}$ aliphatic cyclic ether, a $C_4$ to $C_{20}$ aromatic cyclic ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some aspects, each ether ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, dibenzofuran, diphenyl ether, a ditolyl ether, or any combination thereof; alternatively, dimethyl ether, diethyl ether, a dipropyl ether, a dibutyl ether, methyl ethyl ether, a methyl propyl ether, a methyl butyl ether, or any combination thereof; tetrahydrofuran, a dihydrofuran, 1,3-dioxolane, tetrahydropyran, a dihydropyran, a pyran, a dioxane, or any combination thereof; furan, benzofuran, isobenzofuran, dibenzofuran, or any combination thereof; diphenyl ether, a ditolyl ether, or any combination thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, dibenzofuran; alternatively, diphenyl ether; or alternatively, a ditolyl ether.

Generally, the organoaluminum compound utilized in the catalyst systems disclosed herein can be any organoaluminum compound which in conjunction with the heteroatomic ligand transition metal compound complex (or the transition metal compound and heteroatomic ligand) can catalyze the formation of an oligomer product. In an aspect, the organoaluminum compound can comprise, consist essentially of, or be an aluminoxane, an alkylaluminum compound, or any combination thereof; alternatively, an aluminoxane; or alternatively, an alkylaluminum compound. In an aspect, the alkylaluminum compound comprise, consist essentially of, or be a trialkylaluminum, an alkylaluminum halide, an alkylaluminum alkoxide, or any combination thereof. In some aspects, the alkylaluminum compound comprise, consist essentially of, or be a trialkylaluminum, an alkylaluminum halide, or any combination thereof; alternatively, a trialkylaluminum, an alkylaluminum alkoxide, or any combination thereof; or alternatively, a trialkylaluminum. In other aspects, the alkylaluminum compound can be a trialkylaluminum; alternatively, an alkylaluminum halide; or alternatively, an alkylaluminum alkoxide. In an aspect, the aluminoxane utilized in the catalyst systems which are utilized in the processes and systems comprise, consist essentially of, or be any aluminoxane which in conjunction with the heteroatomic ligand transition metal compound complex (or the transition metal compound and heteroatomic ligand), can catalyze the formation of an oligomer product. In a non-limiting aspect, the aluminoxane can have a repeating unit characterized by the Formula I:

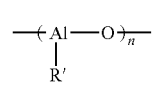

Formula I wherein R' is a linear or branched alkyl group. Alkyl groups of the aluminoxanes and alkylaluminum compounds are independently described herein and can be utilized without limitation to further describe the aluminoxanes having Formula I and/or the alkylaluminum compounds. Generally, n of Formula I can be greater than 1; or alternatively, greater than 2. In an aspect, n can range from 2 to 15; or alternatively, range from 3 to 10.

In an aspect, each alkyl group of an aluminoxane and/or alkylaluminum compound independently can be a $C_1$ to $C_{20}$ alkyl group; alternatively, a $C_1$ to $C_{10}$ alkyl group; or alternatively, a $C_1$ to $C_6$ alkyl group. In an aspect, each alkyl group of an aluminoxane and/or alkylaluminum compound a methyl group, an ethyl group, a propyl group, a butyl group, a pentyl group, a hexyl group, a heptyl group, or an octyl group; alternatively, a methyl group, a ethyl group, a butyl group, a hexyl group, or an octyl group. In some aspects, each alkyl group of an aluminoxane and/or alkylaluminum compound can be a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In a non-limiting aspect, the aluminoxane comprise, consist essentially of, or be methylaluminoxane (MAO), ethylaluminoxane, modified methylaluminoxane (MMAO), n-propylaluminoxane, iso-propyl-aluminoxane, n-butylaluminoxane, sec-butylaluminoxane, iso-butylaluminoxane, t-butylaluminoxane, 1-pentylaluminoxane, 2-entylaluminoxane, 3-pentyl-aluminoxane, iso-pentyl-aluminoxane, neopentylaluminoxane, or mixtures thereof. In some non-limiting aspects, the aluminoxane comprise, or consist essentially of, or be methylaluminoxane (MAO), modified methylaluminoxane (MMAO), isobutyl aluminoxane, t-butyl aluminoxane, or mixtures thereof. In other non-limiting aspects, the aluminoxane can be, comprise, or consist essentially of, methylaluminoxane (MAO); alternatively, ethylaluminoxane; alternatively, modified methylaluminoxane (MMAO); alternatively, n-propylaluminoxane; alternatively, iso-propyl-aluminoxane; alternatively, n-butylaluminoxane; alternatively, sec-butylaluminoxane; alternatively, iso-butylaluminoxane; alternatively, t-butyl aluminoxane; alternatively, 1-pentyl-aluminoxane; alternatively, 2-pentylaluminoxane; alternatively, 3-pentyl-aluminoxane; alternatively, iso-pentyl-aluminoxane; or alternatively, neopentylaluminoxane.

Various aspects described herein refer to non-hydrogen substituents such as halogen (or halo, halide), hydrocarbyl, hydrocarboxy, alkyl, and/or alkoxy substituents. In an embodiment, each non-hydrogen substituent of any aspect calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Each hydrocarbyl substituent independently can be a $C_1$ to $C_{10}$ hydrocarbyl group; or alternatively, a $C_1$ to $C_5$ hydrocarbyl group. Each hydrocarboxy substituent independently can be a $C_1$ to $C_{10}$ hydrocarboxy group; or alternatively, a $C_1$ to $C_5$ hydrocarboxy group. Each halide substituent independently can be a fluoride, chloride, bromide, or iodide; alternatively, a fluoride or chloride; alternatively, a fluoride; alternatively, a chloride; alternatively, a bromide; or alternatively, an iodide.

In an aspect, any hydrocarbyl substituent independently can be an alkyl group, an aryl group, or an aralkyl group; alternatively, an alkyl group; alternatively, an aryl group; or alternatively, an aralkyl group. In an aspect, any alkyl substituent independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an aspect, any aryl substituent independently can be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an aspect, any aralkyl substituent independently can be benzyl group or an ethylphenyl group (2-phenyleth-1-yl or 1-phenyleth-1-yl); alternatively, a benzyl group; alternatively, an ethylphenyl group; alternatively, a 2-phenyleth-1-yl group; or alternatively, a 1-phenyleth-1-yl group.

In an aspect, any hydrocarboxy substituent independently can be an alkoxy group, an aryloxy group, or an aralkoxy group; alternatively, an alkoxy group; alternatively, an aryloxy group, or an aralkoxy group. In an aspect, any alkoxy substituent independently can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an aspect, any aryloxy substituent independently can be phenoxy group, a tolyoxy group, a xyloxy group, or a 2,4,6-trimethylphenoxy group; alternatively, a phenoxy group; alternatively, a tolyoxy group, alternatively, a xyloxy group; or alternatively, a 2,4,6-trimethylphenoxy group. In an aspect, any aralkoxy substituent independently can be benzoxy group.

Generally, the heat exchange medium (also referred to as the first heat exchange medium) can be any fluid capable of maintaining the desired reaction mixture temperature through heat exchange contact in the first heat exchanger. In any process, reaction system, or heat exchange system described herein, the heat exchange medium can have a boiling point at 1 atmosphere (101.3 kPa) greater than a reaction mixture temperature (or average reaction mixture temperature) on the first heat exchange surface first side (e.g. first heat exchange surface first side 113) and can have a boiling point at the pressure on the first heat exchange surface second side (e.g. first heat exchange surface second side 114) less than the reaction mixture temperature (or average reaction mixture temperature) on the first heat exchange surface first side (e.g. first heat exchange surface first side 113). In any process, reaction system, or heat exchange system described herein, the minimum first heat exchange medium boiling point at 1 atmosphere (101.3 kPa) can be 40, 50, 60, or 70° C.; alternatively or additionally, the maximum first heat exchange medium boiling point at 1 atmosphere (101.3 kPa) can be 150, 140, 130, 120, or 110° C. The first heat exchange medium boiling point at 1 atmosphere (101.3 kPa) can range from any boiling point at 1 atmosphere (101.3 kPa) minimum temperature disclosed herein to any boiling point at 1 atmosphere (101.3 kPa) maximum temperature disclosed herein. Non-limiting ranges for the first heat exchange medium boiling point at 1 atmosphere (101.3 kPa) can include a boiling point at 1 atmosphere (101.3 kPa) in a range from 40 to 150° C., 50 to 140° C., 60 to 130° C., 70 to 120° C., or 70 to 110° C. Other suitable ranges for the first heat exchange medium boiling point at 1 atmosphere (101.3 kPa) are readily apparent from the present disclosure.

For any process, reaction system, or heat exchange system described herein, the first heat exchange medium can be an organic heat exchange medium or an inorganic heat exchange medium; alternatively, an organic heat exchange medium; or alternatively, an inorganic heat exchange medium. Organic heat exchange mediums which can be utilized as the first heat exchange medium can comprise $C_6$ to $C_8$ hydrocarbons; alternatively, $C_6$ to $C_8$ aliphatic hydrocarbons; or alternatively $C_6$ to $C_8$ saturated hydrocarbons. Inorganic heat exchange mediums which can be utilized as the first heat exchange medium can include or comprise water. Depending upon the specific first heat exchange medium utilized, the heat exchange medium can include additives such as corrosion inhibitors, oxygen scavengers, emulsifying agents, dispersants, antifoaming agents, neutralizing agents, filming agents, deposit control agents, among other additives.

For any process, reaction system, or heat exchange system described herein, the second heat exchange medium can be any fluid capable of maintaining the desired first heat exchange medium temperature through heat exchange contact in the second heat exchanger (i.e., second heat exchanger 211) or with the second heat exchange surface (i.e., second heat exchange surface 212). In an aspect, the second heat exchange medium on the second heat exchange surface second side (i.e., second heat exchange surface second side 214) can have a boiling point greater than boiling point of the first heat exchange medium at the pressure on the first heat exchange surface second side/second heat exchange surface first side (i.e., first heat exchange surface second side 114/second heat exchange surface first side 213). Non-limiting examples of second heat exchange medium(s) can include those fluids comprising water, glycol, one or more hydrocarbons, or combinations thereof.

The processes and reaction systems described herein can use an organic reaction medium. Generally, the organic reaction can act as a solvent or a diluent in the processes described herein. In an aspect, the organic reaction medium can be a hydrocarbon, a halogenated hydrocarbon, or a combination thereof, for example. Hydrocarbons and halogenated hydrocarbons which can be used as an organic reaction medium can include, for example, aliphatic hydrocarbons, aromatic hydrocarbons, petroleum distillates, halogenated aliphatic hydrocarbons, halogenated aromatic hydrocarbons, or combinations thereof. Aliphatic hydrocarbons which can be useful as an organic reaction medium include $C_3$ to $C_{20}$ aliphatic hydrocarbons, or $C_4$ to $C_{15}$ aliphatic hydrocarbons, or $C_5$ to $C_{10}$ aliphatic hydrocarbons, for example. The aliphatic hydrocarbons which can be used as an organic reaction medium can be cyclic or acyclic and/or can be linear or branched, unless otherwise specified. Non-limiting examples of suitable acyclic aliphatic hydrocarbon organic reaction mediums that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), or combinations thereof. Non-limiting examples of suitable cyclic aliphatic hydrocarbons which can be used as an organic reaction medium include cyclohexane, and methyl cyclohexane, for example. Aromatic hydrocarbons which can be useful as an organic reaction medium include $C_6$ to $C_{10}$ aromatic hydrocarbons. Non-limiting examples of suitable aromatic hydrocarbons that can be utilized singly or in any combination as an organic reaction medium include benzene, toluene, xylene (including ortho-xylene, meta-xylene, para-xylene, or mixtures thereof), ethylbenzene, or combinations thereof. Halogenated aliphatic hydrocarbons which can be useful as an organic reaction medium include $C_1$ to $C_{15}$ halogenated aliphatic hydrocarbons. $C_1$ to $C_{10}$ halogenated aliphatic hydrocarbons, or $C_1$ to $C_5$ halogenated aliphatic hydrocarbons, for example. The halogenated aliphatic hydrocarbons which can be used as an organic reaction medium can be cyclic or acyclic and/or can be linear or branched, unless otherwise specified. Non-limiting examples of suitable halogenated aliphatic hydrocarbons which can be utilized as an organic reaction medium include methylene chloride, chloroform, carbon tetrachloride, dichloroethane, trichloroethane, and combinations thereof. Halogenated aromatic hydrocarbons which can be useful as an organic reaction medium include $C_6$ to $C_{20}$ halogenated aromatic hydrocarbons, or $C_6$ to $C_{10}$ halogenated aromatic hydrocarbons, for example. Non-limiting examples of suitable halogenated aromatic hydrocarbons which can be used as a solvent include chlorobenzene, dichlorobenzene, or combinations thereof, for example.

The choice of organic reaction medium can be made on the basis of convenience in processing. For example, isobutane can be chosen to be compatible with solvents and diluents used in processes using the product(s) of the process described herein (e.g., using the product for the formation of polymer in a subsequent processing step). In some embodiments, the organic reaction medium can be chosen to be easily separable from the one or more of the oligomers in the oligomer product. In some embodiments, an oligomer of the oligomer product can be utilized as the reaction system solvent. For example, when 1-hexene is an oligomer of an ethylene trimerization process, 1-hexene can be chosen as the reaction system solvent to decrease the need for separation.

Generally, the operating parameters for the reaction zone 101 are disclosed in U.S. Patent Application Publication No. 2017/00812570081256 to Kreischer, entitled "Design of an Ethylene Oligomerization/Trimerization/Tetramerization Reactor".

For any process, reaction system, or heat exchange system described herein, the reaction zone (i.e., reaction zone 101) can operate at any pressure that can facilitate the desired oligomerization (e.g., trimerization, tetramerization, or trimerization and tetramerization of an olefin, for example, ethylene). In an aspect, the reaction zone (reaction zone 101) can operate at any pressure that produces the desired oligomer product (e.g., a trimerization product, tetramerization product, or trimerization and tetramerization product). In some aspects, the oligomer product can be formed at a pressure greater than or equal to 0 psig (0 KPa), 50 psig (344 KPa), 100 psig (689 KPa), or 150 psig (1.0 MPa). In other aspects, the oligomer product can be formed at a pressure ranging from 0 psig (0 KPa) to 2,500 psig (17.3 MPa), 0 psig (KPa) to 1,600 psig (11.0 MPa), 0 psig (KPa) to 1,500 psig (10.4 MPa), 50 psig (344 KPa) to 2,500 psig (17.3 MPa), 100 psig (689 KPa) to 2,500 psig (17.3 MPa), 150 psig (1.0 MPa) to 2,000 psig (13.8 MPa), or 300 psig (2.0 MPa) to 900 psig (6.2 MPa). In an aspect, the oligomer product can be formed at an ethylene pressure (or ethylene partial pressure) greater than or equal to 0 psig (0 KPa), 50 psig (344 KPa), 100 psig (689 KPa), or 150 psig (1.0 MPa). In other aspects, the ethylene pressure (or ethylene partial pressure) at which the ethylene oligomer product can be formed can range from 0 psig (0 KPa) to 2,500 psig (17.3 MPa), 50 psig (345 KPa) to 2,500 psig (17.3 MPa), 100 psig (689 KPa) to 2,500 psig (17.3 MPa), or 150 psig (1.0 MPa) to 2,000 psig (13.8 MPa). In other aspects, the ethylene pressure (or ethylene partial pressure) at which the ethylene oligomer product can be formed can range from 500 psig (3.45 MPa) to 5,000 psig (34.5 MPa), 1,000 psig (6.89 MPa) to 5,000 psig (34.5 MPa), 2,000 psig (13.8 MPa) to 5,000 psig (34.5 MPa), 3,000 psig (20.7 MPa) to 5,000 psig (34.5 MPa), 500 psig (3.44 MPa) to 4,000 psig (27.6 MPa), 1,000 psig (6.89 MPa) to 4,000 psig (27.6 MPa), or 1000 psig (6.89 MPa) to 3,500 psig (24.1 MPa).

For any process or reaction system described herein, the oligomer product can be formed (or the reaction zone can operate) at a minimum hydrogen partial pressure of 1 psi (6.9 kPa), 2 psi (14 kPa); 5 psi (34 kPa), 10 psi (69 kPa), or 15 psi (103 kPa); alternatively or additionally at a maximum hydrogen partial pressure of 200 psi (1.4 MPa), 150 psi (1.03 MPa), 100 psi (689 kPa), 75 psig (517 kPa), or 50 psi (345 kPa). In an embodiment, the oligomer product can be formed (or the reaction zone can operate) at a hydrogen partial pressure ranging from any minimum hydrogen partial pressure disclosed herein to any maximum hydrogen partial pressure disclosed herein. In some non-limiting embodiments wherein hydrogen is utilized, the oligomer product can be formed (or the reaction zone can operate) at a hydrogen partial pressure from 1 psi (6.9 kPa) to 200 psi (1.4 MPa), from 5 psi (34 kPa) to 150 psi (1.03 MPa), from 10 psi (69 kPa) to 100 psi (689 kPa), or from 15 psi (100 kPa) to 75 psig (517 kPa). Other hydrogen partial pressure ranges that can be utilized are readily apparent to those skilled in the art with the aid of this disclosure.

In other aspects wherein hydrogen is utilized, the oligomer product can be formed (or the reaction zone can operate) at a minimum hydrogen to ethylene mass ratio of (0.05 g hydrogen)/(kg ethylene), (0.1 g hydrogen)/(kg ethylene), (0.25 g hydrogen)/(kg ethylene), (0.4 g hydrogen)/(kg ethylene), or (0.5 g hydrogen)/(kg ethylene); alternatively or additionally, at a maximum hydrogen to ethylene mass ratio can be (5 g hydrogen)/(kg ethylene), (3 g hydrogen)/(kg ethylene), (2.5 g hydrogen)/(kg ethylene), (2 g hydrogen)/(kg ethylene), or (1.5 g hydrogen)/(kg ethylene). In an embodiment, the oligomer product can be formed (or the reaction zone can operate) at a hydrogen to ethylene mass ratio ranging from any minimum hydrogen to ethylene mass ratio disclosed herein to any maximum hydrogen to ethylene mass ratio disclosed herein. In some non-limiting embodiments, the oligomer product can be formed (or the reaction zone can operate) at a hydrogen to ethylene mass ratio from (0.05 g hydrogen)/(kg ethylene) to (5 g hydrogen)/(kg ethylene), from (0.25 g hydrogen)/(kg ethylene) to (5 g hydrogen)/(kg ethylene), from (0.25 g hydrogen)/(kg ethylene) to (4 g hydrogen)/(kg ethylene), from (0.4 g hydrogen)/(kg ethylene) to (3 g hydrogen)/(kg ethylene), from (0.4 g hydrogen)/(kg ethylene) to (2.5 g hydrogen)/(kg ethylene), from (0.4 g hydrogen)/(kg ethylene) to (2 g hydrogen)/(kg ethylene), or from (0.5 g hydrogen)/(kg ethylene) to (2 g hydrogen)/(kg ethylene). Other hydrogen to ethylene mass ratio ranges that can be utilized are readily apparent to those skilled in the art with the aid of this disclosure.

For any process, reaction system, or heat exchange system described herein, the temperature (or average temperature) at which the oligomer product (e.g., trimerization product, tetramerization product, or trimerization and tetramerization product) can be formed in the reaction zone (i.e., reaction zone 101) can be a minimum temperature of 0° C., 25° C., 40° C., 50° C. 60° C. 70° C., or 75° C.; alternatively or additionally, a maximum temperature of 120° C., 110° C., 100° C., or 95° C., or 90° C. the temperature (or average temperature) at which the oligomer product (e.g., trimerization product, tetramerization product, or trimerization and tetramerization product) can be formed in the reaction zone (i.e., reaction zone 101) can range from any minimum temperature (or average temperature) disclosed herein to any maximum temperature (or average temperature) disclosed herein. Non-limiting temperature (or average temperatures) at which the oligomer product (e.g., trimerization product, tetramerization product, or trimerization and tetramerization product) can be formed can range from 0° C. to 120° C., from 25° C. to 120° C., from 40° C. to 110° C., from 50° C. to 100° C., from 50° C. to 100° C., from 60° C. to 95° C., from 70° C. to 95° C., from 75° C. to 95° C., or from 75° C. to 90° C.). Other suitable ranges for the temperature (or average temperatures) at which the oligomer product (e.g., trimerization product, tetramerization product, or trimerization and tetramerization product) can be formed are readily apparent from the present disclosure.

For any process or reaction system described herein, the reaction time (or average reaction time) that the reaction mixture spends in the reaction zone (i.e., reaction zone 101) can comprise any time that can produce the desired quantity of oligomer product; alternatively, any time that can provide a desired catalyst system productivity; alternatively, any time that can provide a desired conversion of olefin (e.g., ethylene). For example, the olefin monomer (e.g., ethylene monomer) conversion can be at least 30 wt. %; alternatively, at least 35 wt. %; alternatively, at least 40 wt. %; alternatively, at least 45 wt. %.

For any process or reaction system described herein, the oligomer product is an ethylene trimerization product that comprises at least 70 wt. % hexene; alternatively, at least 75 wt. % hexene; alternatively, at least 80 wt. % hexene; alternatively, at least 85 wt. % hexene; or alternatively, at least 90 wt. % hexene based upon the weight of the oligomer product. In some aspects, the ethylene trimerization product can comprise from 70 wt. % to 99.8 wt. % hexene; alternatively, from 75 wt. % to 99.7 wt. % hexene; or alternatively, from 80 wt. % to 99.6 wt. % hexene based upon the weight of the ethylene trimerization product.

For any process or reaction system described herein, the oligomer product is an ethylene tetramerization product that comprises at least 70 wt. % octene; alternatively, at least 75 wt. % octene; alternatively, at least 80 wt. % octene; alternatively, at least 85 wt. % octene; or alternatively, at least 90 wt. % octene based upon the weight of the ethylene tetramerization product. In some aspects, the ethylene tetramerization product can comprise from 70 wt. % to 99.8 wt. % octene; alternatively, from 75 wt. % to 99.7 wt. % octene; or alternatively, from 80 wt. % to 99.6 wt. % octene based upon the weight of the ethylene tetramerization product.

For any process or reaction system described herein, the oligomer product is an ethylene trimerization and tetramerization product that comprises at least 70 wt. % hexene and octene; alternatively, at least 75 wt. % hexene and octene; alternatively, at least 80 wt. % hexene and octene; alternatively, at least 85 wt. % hexene and octene; or alternatively, at least 90 wt. % hexene and octene based upon the weight of the ethylene trimerization and tetramerization product. In other aspects, the ethylene trimerization and tetramerization product can comprise from 70 wt. % to 99.8 wt. % hexene and octene; alternatively, from 75 wt. % to 99.7 wt. % hexene and octene; or alternatively, from 80 wt. % to 99.6 wt. % hexene and octene based upon the weight of the ethylene trimerization and tetramerization product.

For any process or reaction system described herein, where the oligomer product is an ethylene trimerization product or an ethylene trimerization and tetramerization product, the ethylene trimer can comprise at least 85 wt. % 1-hexene; alternatively, at least 87.5 wt. % 1-hexene; alternatively, at least 90 wt. % 1-hexene; alternatively, at least 92.5 wt. % 1-hexene; alternatively, at least 95 wt. % 1-hexene; alternatively, at least 97 wt. % 1-hexene; or alternatively, at least 98 wt. % 1-hexene by weight of the ethylene trimer, or from 85 wt. % to 99.9 wt. % 1-hexene; alternatively, from 87.5 wt. % to 99.9 wt. % 1-hexene; alternatively, from 90 wt. % to 99.9 wt. % 1-hexene; alternatively, from 92.5 wt. % to 99.9 wt. % 1-hexene; alternatively, from 95 wt. % to 99.9 wt. % 1-hexene; alternatively, from 97 wt. % to 99.9 wt. % 1-hexene; or alternatively, from 98 wt. % to 99.9 wt. % 1-hexene by weight of the ethylene trimer.

For any process or reaction system described herein, where the oligomer product is an ethylene tetramerization or ethylene trimerization and tetramerization product, the ethylene tetramer can comprise at least 85 wt. % 1-octene; alternatively, at least 87.5 wt. % 1-octene; alternatively, at least 90 wt. % 1-octene; alternatively, at least 92.5 wt. % 1-octene; alternatively, at least 95 wt. % 1-octene; alternatively, at least 97 wt. % 1-octene; or alternatively at least 98 wt. % l-octene by weight of the ethylene tetramer or from 85 wt. % to 99.9 wt. % 1-octene; alternatively, from 87.5 wt. % to 99.9 wt. % 1-octene; alternatively, from 90 wt. % to 99.9 wt. % 1-octene; alternatively, from 92.5 wt. % to 99.9 wt. % 1-octene; alternatively, from 95 wt. % to 99.9 wt. % 1-octene; alternatively, from 97 wt. % to 99.9 wt. % 1-octene; alternatively, from 98 wt. % to 99.9 wt. % 1-octene by weight of the ethylene tetramer.

Additional Disclosure

The following is provided as additional disclosure for combinations of features and aspects of the present invention.

Statement 1. A process comprising: controlling (or providing) a reaction mixture temperature within the reaction zone with a heat exchange system, the heat exchange system comprising a first heat exchanger providing indirect contact between at least a portion of the reaction mixture and a first heat exchange medium, the first heat exchanger comprising a first heat exchange surface having i) a first heat exchange surface first side in contact with at least a portion of the reaction mixture, and ii) a first heat exchange surface second side in contact with the first heat exchange medium; where a pressure on the first heat exchange surface second side can be (or can be controlled to be) any pressure less than 1 atmosphere (101.3 kPa) described herein (e.g., less than 1 atmosphere; a minimum pressure of 0.1, 0.12, 0.15, 0.2, 0.25, 0.3, 0.375, or 0.45 atmospheres; a maximum pressure, 0.9, 0.875, 0.85, 0.8, 0.75, or 0.7 atmospheres; or range from 0.1 to 0.9, 0.12 to 0.9, 0.15 to 0.875, 0.2 to 0.875, 0.3 to 0.85, 0.375 to 0.85, or 0.45 to 0.85 atmospheres; among other pressures disclosed herein).

Statement 2. The process of Statement 1 further comprising providing (or controlling) the pressure on the first heat exchange surface second side to provide (or control) the reaction mixture temperature within the reaction zone.

Statement 3. A process comprising: providing (or controlling) a pressure in a heat exchange system to provide (or control) a reaction mixture temperature within a reaction zone, the heat exchange system comprising a first heat exchanger providing indirect contact between the reaction mixture and a first heat exchange medium, the first heat exchanger comprising a first heat exchange surface having i) a first heat exchange surface first side in contact with the reaction mixture, and ii) a first heat exchange surface second side in contact with the first heat exchange medium; where a pressure on the first heat exchange surface second side of the first heat exchanger can be (or can be controlled to be) any pressure less than 1 atmosphere (101.3 kPa) described herein (e.g., less than 1 atmosphere; a minimum pressure of 0.1, 0.12, 0.15, 0.2, 0.25, 0.3, 0.375, or 0.45 atmospheres; a maximum pressure, 0.9, 0.875, 0.85, 0.8, 0.75, or 0.7 atmospheres; or range from 0.1 to 0.9, 0.12 to 0.9, 0.15 to 0.875, 0.2 to 0.875, 0.3 to 0.85, 0.375 to 0.85, or 0.45 to 0.85 atmospheres; among other pressures disclosed herein).

Statement 4. The process of any one of Statements 1-3, where the first heat exchange medium has a boiling point at 1 atmosphere (101.3 kPa) greater than an average reaction mixture temperature on the first heat exchange surface first side and a boiling point at the pressure on the first heat exchange surface second side less than the average reaction mixture temperature on the first heat exchange surface first side.

Statement 5. The process of any one of Statements 1-4, wherein a first part of the at least a portion of the reaction mixture on the first heat exchange surface first side indirectly contacts a liquid phase of the first heat exchange medium on the first heat exchange surface second side and a second part of the at least a portion of the reaction mixture on the first heat exchange surface first side indirectly contacts a vapor phase of the first heat exchange medium on the first heat exchange surface second side (providing a first level of liquid phase of the first heat exchange medium on the first heat exchange surface second side).

Statement 6. The process of Statement 5, wherein a percentage of the at least a portion of the reaction mixture on the first heat exchange surface first side which indirectly contacts a liquid phase of the first heat exchange medium on the first heat exchange surface second side can be (or can be controlled to be) any percentage disclosed herein (e.g., greater than or equal to 50%, 60%, 70%, 75%, 80%, or 90% by volume; less than or equal to 95%, 90%, 85%, 80%, 75%, or 70% by volume; or from 50% to 95%, from 60% to 95%, from 60% to 90%, from 70% to 90%, from 70% to 85%, or from 75% to 85%, by volume; among other percentages disclosed herein).

Statement 7. The process of Statement 5 or 6, wherein a percentage of the surface area of the first heat exchange surface second side which contacts the liquid phase of the first heat exchange medium can be, or can be controlled to be, any percentage disclosed herein (e.g., at least 50%, 60%, 70%, 75%, 80%, or 90%; less than or equal to 95%, 90%, 85%, 80%, 75%, or 70%; or range from 50% to 95%, from 60% to 95%, from 60% to 90%, from 70% to 90%, from 70% to 85%, or from 75% to 85%; among other percentages disclosed herein).

Statement 8. The process of any one of Statements 5-7, wherein a volume ratio of the liquid phase of the first heat exchange medium in the first heat exchanger (or on the first heat exchange surface second side) to the vapor phase of the first heat exchange medium in the first heat exchanger (or on the first heat exchange surface second side) can be (or can be controlled to be) any volume ratio disclosed herein (e.g., greater than or equal to 1:1, 1.5:1, 2:1, 2.5:1, 3:1, 3.5:1, or 4:1; less than or equal to 20:1, 10:1, 6:1, 4:1, 3:1, or 2.5:1; or from 1:1 to 20:1, from 1.5:1 to 20:1, from 1.5:1 to 9:1, from 2:1 to 9:1, from 2.5:1 to 6:1, or from 3:1 to 6:1; among other ratios disclosed herein), wherein the heat exchange system further comprises one or more pressure control devices.

Statement 9. The process of Statements 5-8, comprising controlling a first level of a liquid phase of the first heat exchange medium on the first heat exchange surface second side.

Statement 10. The process of Statements 5-8, wherein controlling the reaction mixture temperature (or average reaction mixture temperature) comprises controlling a first level of a liquid phase of the first heat exchange medium on the first heat exchange surface second side Statement 11. The process of Statement 10 or 11, wherein controlling the first level of the liquid phase of the first heat exchange medium comprises increasing or decreasing the flow rate of the first heat exchange medium.

Statement 12. The process of any one of Statements 1-11, where the heat exchange system further comprises one or more pressure control devices providing (or controlling) the pressure of less than 1 atmosphere (101.3 kPa) on the first heat exchange surface second side.

Statement 13. The process of Statement 12, wherein the pressure on the first heat exchange surface first side (or the first heat exchange medium) can be controlled (or provided) by a pressure set point of the one or more pressure control devices.

Statement 14. The process of Statement 13, wherein controlling the reaction mixture temperature (or average reaction mixture temperature) in the reaction zone comprises controlling the pressure set point of the one or more pressure control points.

Statement 15. The process of any one of Statements 1-4, wherein the heat exchange system further comprises a second heat exchanger providing indirect contact between the first heat exchange medium and a second heat exchange medium, the second heat exchanger comprising a second heat exchange surface having i) a second heat exchange surface first side in contact with the first heat exchange medium, and ii) a second heat exchange surface second side in contact with the second heat exchange medium; and where a pressure on the second heat exchange surface first side of the second heat exchanger can be (or can be controlled to be) any pressure less than 1 atmosphere (101.3 kPa) described herein (e.g., less than 1 atmosphere; a minimum pressure of 0.1, 0.12, 0.15, 0.2, 0.25, 0.3, 0.375, or 0.45 atmospheres; a maximum pressure, 0.9, 0.875, 0.85, 0.8, 0.75, or 0.7 atmospheres; or range from 0.1 to 0.9, 0.12 to 0.9, 0.15 to 0.875, 0.2 to 0.875, 0.3 to 0.85, 0.375 to 0.85, or 0.45 to 0.85 atmospheres).

Statement 16. The process of Statement 15, where the second heat exchange surface does not contact the reaction mixture.

Statement 17. The process of Statement 15 or 16, wherein the heat exchange system further comprises one or more pressure control devices in fluid communication with the first heat exchange surface second side and second heat exchange surface first side.

Statement 18. The process of Statement 17, where the heat exchange system further comprises a plurality of conduits connecting the first heat exchanger and the second heat exchanger and allowing for flow of the first heat exchange medium between the first heat exchange surface second side and the second heat exchange surface first side.

Statement 19. The process of Statement 18 where at least one of one or more conduits allows for flow of the first heat exchange medium from the first heat exchange surface second side to the second heat exchange surface first side and at least one of the one or more conduits allows for flow of the first heat exchange medium from the second heat exchange surface first side to the first heat exchange surface second side.

Statement 20. The process of Statement 17 or 18, wherein at least one of the one or more pressure control devices is in [direct] fluid communication with at least one the one of the plurality of conduits.

Statement 21. The process of any one of Statements 17-20, wherein the one or more pressure control devices provides (or controls) the pressure of less than 1 atmosphere (101.3 kPa) on the first heat exchange surface second side and on the second heat exchange surface first side and/or controls the pressure of less than 1 atmosphere (101.3 kPa) on the first heat exchange surface second side and on the second heat exchange surface first side.

Statement 22. The process of Statement 21, wherein the pressure on the first heat exchange surface first side and on the second heat exchange surface first side can be controlled by a pressure set point on one of the one or more pressure control devices.

Statement 23. The process of any one of Statements 19-22, wherein controlling the reaction mixture temperature (or average reaction mixture temperature) comprises controlling the pressure on the first heat exchange surface first side and on the second heat exchange surface first side by controlling the pressure provided by the one or more pressure control devices.

Statement 24. The process of any one of Statements 15-23, wherein a first part of the at least a portion of the reaction mixture on the first heat exchange surface first side indirectly contacts a liquid phase of the first heat exchange medium on the first heat exchange surface second side and a second part of the at least a portion of the reaction mixture on the first heat exchange surface first side indirectly contacts a vapor phase of the first heat exchange medium on the first heat exchange surface second side (providing a first level of liquid phase of the first heat exchange medium on the first heat exchange surface second side), and wherein at least a first part of the second heat exchange medium on the second heat exchange surface second side indirectly contacts the vapor phase of the first heat exchange medium on the second heat exchange surface first side and a second part of the second heat exchange medium on the second heat exchange surface second side indirectly contacts liquid phase of the first heat exchange medium on the second heat exchange surface first side (providing a second level of liquid phase of the first heat exchange medium on the second heat exchange surface first side).

Statement 25. The process of Statement 24, wherein a percentage of the at least a portion of the reaction mixture on the first heat exchange surface first side which indirectly contacts a liquid phase of the first heat exchange medium on the first heat exchange surface second side can be (or can be controlled to be) any percentage disclosed herein (e.g., greater than or equal to 50%, 60%, 70%, 75%, 80%, or 90% by volume; less than or equal to 95%, 90%, 85%, 80%, 75%, or 70% by volume; or from 50% to 95%, from 60% to 95%, from 60% to 90%, from 70% to 90%, from 70% to 85%, or from 75% to 85%, by volume; among other percentages disclosed herein).

Statement 26. The process of Statement 24 or 25, wherein a percentage of the surface area of the first heat exchange surface second side which contacts the liquid phase of the first heat exchange medium can be, or can be controlled to be, any percentage disclosed herein (e.g., at least 50%, 60%, 70%, 75%, 80%, or 90%; less than or equal to 95%, 90%, 85%, 80%, 75%, or 70%; or range from 50% to 95%, from 60% to 95%, from 60% to 90%, from 70% to 90%, from 70% to 85%, or from 75% to 85%; among other percentages disclosed herein).

Statement 27. The process of any one of Statements 24-26, wherein a volume ratio of the liquid phase of the first heat exchange medium in the first heat exchanger (or on the first heat exchange surface second side) to the vapor phase of the first heat exchange medium in the first heat exchanger (or on the first heat exchange surface second side) can be (or can be controlled to be) any volume ratio disclosed herein (e.g., greater than or equal to 1:1, 1.5:1, 2:1, 2.5:1, 3:1, 3.5:1, or 4:1; less than or equal to 20:1, 10:1, 6:1, 4:1, 3:1, or 2.5:1; or from 1:1 to 20:1, from 1.5:1 to 20:1, from 1.5:1 to 9:1, from 2:1 to 9:1, from 2.5:1 to 6:1, or from 3:1 to 6.1; among other ratios disclosed herein), wherein the heat exchange system further comprises one or more pressure control devices Statement 28. The process of any one of Statement 24-27, wherein a percentage of the second heat exchange medium on the second heat exchange surface second side which indirectly contacts the liquid phase of the first heat exchange medium on the second heat exchange surface first side can be (or can be controlled to be) any percentage disclosed herein (e.g., greater than or equal to 50%, 60%, 70%, 80%, or 90%, by volume; less than or equal to 95%, 90%, 85%, 80%, 75%, or 70%, by volume; or from 50% to 95%, from 60% to 95%, from 60% to 90%, from 70% to 90%, from 70% to 85%, or from 75% to 85%, by volume Statement 29. The process of any one of Statements 24-28, wherein a volume ratio of the liquid phase of the first heat exchange medium in the second heat exchanger (or on the second heat exchange surface first side) to the vapor phase of the first heat exchange medium in the second heat exchanger (or on the second heat exchange surface first side) can be (or can be controlled to be) any volume ratio disclosed herein (e.g., greater than or equal to 1:1, 1.5:1, 2:1, 2.5:1, 3:1, 3.5:1, or 4:1; less than or equal to 20:1, 10:1, 6:1, 4:1, 3:1, or 2.5:1; or from 1:1 to 20:1, from 1.5:1 to 20:1, from 1.5:1 to 9:1, from 2:1 to 9:1, from 2.5:1 to 6:1, or from 3:1 to 6.1).

Statement 30. The process of Statement 24-29, wherein controlling the reaction mixture temperature (or average reaction mixture temperature) comprises controlling the pressure on the first heat exchange surface second side, controlling the first level of the liquid phase of the first heat exchange medium on the first heat exchange surface second side, controlling the second level of the liquid phase of the first heat exchange medium on the second heat exchange surface first side, or any combination thereof.

Statement 31. The process of any one of Statements 24-29, wherein controlling the reaction mixture temperature comprises controlling the first level of the liquid phase of the first heat exchange medium on the first heat exchange surface second side.

Statement 32. The process of Statement 31, wherein the first level of the liquid phase of the first heat exchange medium on the first heat exchange surface second side comprises a) controlling a second level of a liquid phase of the first heat exchange medium on the second heat exchange surface first side b) adding first heat exchange medium to the heat exchange system or removing a portion of the first heat exchange medium from the heat exchange system, c) controlling the pressure on the first heat exchange surface second side (and/or first heat exchange medium, and/or second heat exchange surface first side, or d) any combination thereof.

Statement 33. The process of any one of Statements 15-32, wherein a second level of the liquid phase of the first heat exchange medium on the second heat exchange surface first side is vertically higher relative to a common reference point on the ground than the first level of the liquid phase of the first heat medium on the first heat exchange surface second side.

Statement 34. The process of any one of Statements 15-33, wherein the second heat exchange surface comprises vertically oriented tubes or plates.

Statement 35. The process of any one of Statements 1-34, wherein the first heat exchange surface comprises horizontally oriented tubes or plates.

Statement 36. The process of any one of Statements 1-35, wherein the reaction mixture temperature (or average reaction mixture temperature) in the reaction zone (or on the first heat exchange surface first side) can have any values disclosed herein (e.g., a minimum temperature of 0° C. 25° C. 40° C. 50° C. 60° C., 70° C. or 75° C.; a maximum temperature of 120° C., 110° C., 100° C. or 95° C., or 90° C.; in a range from 0° C. to 120° C., from 25° C. to 120° C., from 40° C. to 110° C. from 50° C. to 100° C., from 50° C. to 100° C., from 60° C. to 95° C., from 70° C. to 95° C., from 75° C. to 95° C., or from 75° C. to 90° C.).

Statement 37. The process of any one of Statements 1-36, wherein the first heat exchange medium has any boiling point at 1 atmosphere (101.3 kPa) disclosed herein (e.g., a minimum of 40, 50, 60, or 70° C.; a maximum of 150, 140, 130, 120, or 110° C.; or in a range from 40 to 150° C., 50 to 140° C., 60 to 130° C., 70 to 120° C., or 70 to 110° C., among others disclosed herein).

Statement 38. The process of any one of Statement 1-37, wherein in the first heat exchange medium comprises any organic heat exchange medium or inorganic heat exchange medium disclosed herein.

Statement 39. The process of any one of Statements 1-38, wherein the first heat exchange medium comprises water.

Statement 40. The process of any one of Statements 1-30, wherein a ratio of heat exchanged reaction mixture volume to the total reaction mixture volume within the reaction zone can have value disclosed herein (e.g., a minimum value of 1:1, 1.5:1, 2:1, 2.5:1, 3:1, or 4:1; a maximum value of 100:1, 50:1, 20:1, 15:1, 12:1, or 9:1; or in a range from 1:1 to 100:1, from 1.5:1 to 100:1, from 2:1 to 100:1, from 3:1 to 100:1, from 4:1 to 100:1, from 3:1 to 50:1, from 3:1 to 20:1, from 4:1 to 50:1, from 4:1 to 15:1, or from 4:1 to 12:1; among others disclosed herein).

Statement 41. The process of any one of Statements 1-40, where a temperature difference between an average reaction mixture temperature on the first heat exchange surface first side and a first heat exchange medium temperature on the first heat exchange surface second side can be (or can be controlled to be) any temperature difference disclosed herein (e.g., less than 20° C., 15° C., 10° C., 7.5° C., 5° C., 4° C., or 3° C.).

Statement 42. The process of any one of Statements 1-41, wherein the first heat exchange medium temperature on the first heat exchange surface second side can be (or can be controlled to be) within any percentage of an average reaction mixture temperature on the first heat exchange surface first side disclosed herein (e.g., 20%, 15%, 12.5%, 10%, 7.5%, 6%, 5%, or 4.5%).

Statement 43. The process of any one of Statements 1-42, wherein a reaction mixture temperature at any point in the reaction zone can be, or can be controlled to be, within any value of an average reaction mixture temperature in the reaction zone disclosed herein (e.g., within 15° C., 10° C., 7.5° C., 5° C., 4° C., 3° C., or 2° C.).

Statement 44. The process of any one of Statements 1-43, wherein a reaction mixture temperature at any point in the reaction zone can be, or can be controlled to be, within any percentage of an average reaction mixture temperature in the reaction zone disclosed herein (e.g., within 3%, 2%, 1.5%, 1%, 0.8%, 0.6%, 0.5%, 0.45%, 0.4%, 0.35%, 0.3%, 0.25%, or 0.2%).

Statement 45. The process of any one of Statements 1-44, wherein the process is selected from the group consisting of an ethylene oligomerization process, an ethylene trimerization process, an ethylene tetramerization process, or an ethylene trimerization and tetramerization process.

Statement 46. The process of any one of Statements 1-45, comprising introducing at least 1) ethylene, 2) a catalyst system comprising i) a heteroatomic ligand transition metal compound complex and any organoaluminum compound, or ii) any heteroatomic ligand, a transition metal compound, and an organoaluminum compound, 3) optionally, a first organic reaction medium, and 4) optionally, hydrogen into a reaction mixture within a reaction zone; and forming an oligomer product in the reaction zone.

Statement 101. A reaction system comprising: a) a reaction zone containing a reaction mixture; and b) a heat exchange system comprising a first heat exchanger configured to provide indirect contact between at least a portion of the reaction mixture and a first heat exchange medium, the first heat exchanger comprising a first heat exchange surface having i) a first heat exchange surface first side configured to contact the reaction mixture, and ii) a first heat exchange surface second side configured to contact a first heat exchange medium; where a pressure on the first heat exchange surface second side of the first heat exchanger is any pressure less than 1 atmosphere (101.3 kPa) described herein (e.g., less than 1 atmosphere; a minimum pressure of 0.1, 0.12, 0.15, 0.2, 0.25, 0.3, 0.375, or 0.45 atmospheres; a maximum pressure, 0.9, 0.875, 0.85, 0.8, 0.75, or 0.7 atmospheres; or range from 0.1 to 0.9, 0.12 to 0.9, 0.15 to 0.875, 0.2 to 0.875, 0.3 to 0.85, 0.375 to 0.85, or 0.45 to 0.85 atmospheres).

Statement 102. The reaction system Statement 101, wherein the heat exchange system further comprises one or more pressure control devices in fluid communication with the first heat exchange surface second side and configured to measure, provide and/or control the pressure of less than 1 atmosphere (101.3 kPa) on the first heat exchange surface second side.

Statement 103. The reaction system of Statement 101 or 102, wherein a first part of the at least a portion of the reaction mixture on the first heat exchange surface first side (or a first part of a surface area of the first heat exchange surface second side) indirectly contacts a liquid phase of the first heat exchange medium on the first heat exchange surface second side and a second part of the at least a portion of the reaction mixture on the first heat exchange surface first side (or a second part of the surface area of the first heat exchange surface second side) indirectly contacts a vapor phase of the first heat exchange medium on the first heat exchange surface second side (providing a first level of liquid phase of the first heat exchange medium on the first heat exchange surface second side).

Statement 104. The reaction system of any one of Statements 101-103, wherein the heat exchange system further comprises a first level indicator and/or controller (coupled to the first heat exchanger and) configured to measure, monitor, and/or control a first level of the liquid phase of the first heat exchange medium on the first heat exchange surface second side.

Statement 105. The reaction system of Statement 104, wherein the first level indicator and/or controller (coupled to the first heat exchanger and) is configured to control the first level of liquid phase of the first heat exchange medium of the first heat exchange surface first side to be a) any percentage of the at least a portion of the reaction mixture on the first heat exchange surface first side which indirectly contacts a liquid phase of the first heat exchange medium on the first heat exchange surface second side disclosed herein, b) any percentage of the surface area of the first heat exchange surface second side which contacts the liquid phase of the first heat exchange medium disclosed herein, c) any volume ratio of the liquid phase of the first heat exchange medium in the first heat exchanger (or on the first heat exchange surface second side) to the vapor phase of the first heat exchange medium in the first heat exchanger (or on the first heat exchange surface second side) disclosed herein, or d) any combination thereof.

Statement 106. The reaction system of Statement 104 or 105, wherein the heat exchange system further comprises a first heat exchange medium flow control valve configured to control the flow rate of the first heat exchange medium.

Statement 107. The reaction system of Statement 106, wherein the first level indicator and/or controller is configured to actuate the heat exchange medium flow control valve to control the level of liquid phase of the of first heat exchange medium on the first heat exchange surface second side.

Statement 108. The reaction system of Statements 101-107, wherein the reaction system further comprises a temperature indicator and/or controller configured to measure and/or control the reaction mixture temperature (or average reaction mixture temperature) within the reaction zone.

Statement 109. The reaction system of Statement 109, wherein the temperature indicator and/or controller is a) coupled to at least one of the pressure control devices of Statements 101 or 102 and configured to actuate a control mechanism to control a pressure set point of the one or more pressure control devices in response to reaction mixture temperature (or average reaction mixture temperature), b) is coupled with the first level indicator or controller of statement 104 or 105, c) the first heat exchange medium flow control valve of statements 106 or 107 and configured to actuate a heat exchange medium flow control valve to control the flow rate of first level of liquid phase of the first heat exchange medium on the first heat exchange surface second side in response to the reaction mixture temperature (or average reaction mixture temperature), or d) a combination thereof.

Statement 110. The reaction system of any one of Statement 101, wherein the heat exchange system further comprises a second heat exchanger configured to provide indirect contact between the first heat exchange medium and a second heat exchange medium, the second heat exchanger comprising a second heat exchange surface having i) a second heat exchange surface first side configured to contact the first heat exchange medium and ii) a second heat exchange surface second side configured to contact the second heat exchange medium; where a pressure on the second heat exchange surface first of the second heat exchanger is any pressure less than 1 atmosphere (101.3 kPa) described herein (e.g., less than 1 atmosphere; a minimum pressure of 0.1, 0.12, 0.15, 0.2, 0.25, 0.3, 0.375, or 0.45 atmospheres; a maximum pressure, 0.9, 0.875, 0.85, 0.8, 0.75, or 0.7 atmospheres; or range from 0.1 to 0.9, 0.12 to 0.9, 0.15 to 0.875, 0.2 to 0.875, 0.3 to 0.85, 0.375 to 0.85, or 0.45 to 0.85 atmospheres).

Statement 111. The reaction system of Statement 108, wherein the second heat exchange surface does not contact the reaction mixture.

Statement 112. The reaction system of Statement 110 or 111, wherein the heat exchange system further comprises a plurality of conduits configured to fluidly connect the first heat exchanger and the second heat exchanger and configured to allow for flow of the first heat exchange medium between the first heat exchange surface second side and the second heat exchange surface first side.

Statement 113. The reaction system of Statement 112, wherein at least one of one or more conduits allows for flow of the first heat exchange medium from the first heat exchange surface second side to the second heat exchange surface first side and at least one of the one or more conduits allows for flow of the first heat exchange medium from the second heat exchange surface first side to the first heat exchange surface second side.

Statement 114. The reaction system of any one of Statements 110-113, wherein a first part of the at least a portion of the reaction mixture on the first heat exchange surface first side indirectly (or a first part of the surface area of the first heat exchange surface second side) contacts a liquid phase of the first heat exchange medium on the first heat exchange surface second side and a second part of the at least a portion of the reaction mixture on the first heat exchange surface first side indirectly (or a second part of the surface area of the first heat exchange surface second side) contacts a vapor phase of the first heat exchange medium on the first heat exchange surface second side (providing a first level of liquid phase of the first heat exchange medium on the first heat exchange surface second side), and wherein at least a first part of the second heat exchange medium on the second heat exchange surface second side indirectly (or a first part of the surface area of the second heat exchange surface first side) contacts the vapor phase of the first heat exchange medium on the second heat exchange surface first side and a second part of the second heat exchange medium on the second heat exchange surface second side indirectly contacts liquid phase of the first heat exchange medium on the second heat exchange surface first side (providing a second level of liquid phase of the first heat exchange medium on the second heat exchange surface first side).

Statement 115. The reaction system of Statement 114, wherein at least one of the plurality of conduits allows for flow of the vapor phase of the first heat exchange medium from the first heat exchange surface second side to the second heat exchange surface first side and at least one of the plurality of conduits allows for flow of the liquid phase of first heat exchanger medium from the second heat exchange surface first side to the first heat exchange surface second side.

Statement 116. The reaction system of any one of Statements 112-115, wherein the first heat exchanger, the second heat exchanger and the plurality of conduits are configured to fluidly connect the first heat exchanger and the second heat exchanger form a first heat exchange medium circulation loop.

Statement 117. The reaction system of any one of Statements 110-116, where the heat exchange system further comprises one or more pressure controllers in fluid communication with the first heat exchange surface second side and the second heat exchange surface first side, the one or more pressure controllers configured to measure, provide, and/or control any pressure disclosed herein on the first heat exchange surface second side and the second heat exchange surface first side.

Statement 118. The reaction system of any one of Statements 112-116, where the heat exchange system further comprises one or more pressure controllers in direct fluid communication at least one of the plurality of conduits, the one or more pressure controllers configured to measure, provide, and/or control any pressure disclosed herein on the first heat exchange surface second side and the second heat exchange surface first side.

Statement 119. The reaction system of any one of Statements 113-116, where the heat exchange system further comprises one or more pressure controllers in direct fluid communication at least one of the plurality of conduits allowing for flow of the first heat exchange medium from the first heat exchange surface second side to the second heat exchange surface first side, the one or more pressure controllers configured to measure, provide, and/or control any pressure disclosed herein on the first heat exchange surface second side and the second heat exchange surface first side.

Statement 120. The reaction system of any one of Statements 114-116, where the heat exchange system further comprises one or more pressure controllers in direct fluid communication with the at least one of the plurality of conduits allowing for flow of the vapor phase of the first heat exchange medium from the first heat exchange surface second side to the second heat exchange surface first side, the one or more pressure controllers configured to measure, provide, and/or control any pressure disclosed herein on the first heat exchange surface second side and the second heat exchange surface first side.

Statement 121. The reaction system of any one of Statements 102 or 117-120, wherein the one or more pressure control devices includes an eductor.

Statement 122. The reaction system of any one of Statements 102 or 117-121, wherein the one or more pressure control devices includes a control valve.

Statement 123. The reaction system of Statement 122, wherein the eductor has a motive fluid inlet fluidly connected to the control valve and a suction inlet fluidly connected to the first heat exchange surface second side.

Statement 124. The reaction system of Statement 123, wherein one of the at least one pressure controllers actuate the control valve to provide a motive fluid to the motive fluid inlet of the eductor to provide the pressure of less than 1 atmosphere (101.3 kPa) on the first heat exchange surface second side.

Statement 125. The reaction system of Statement 122 or 123, wherein the pressure controller is configured to actuate the control valve between an open position and a closed position such that non-condensable components in the first heat exchange medium are removed from the first heat exchange medium.

Statement 126. The reaction system of any one of Statements 110-123, wherein the heat exchange system further comprises a first level indicator and/or controller (coupled to the first heat exchanger and) configured to measure, monitor, and/or control the first level of the liquid phase of the first heat exchange medium on the first heat exchange surface second side.

Statement 127. The reaction system of Statement 125, wherein the first level indicator and/or controller (coupled to the first heat exchanger and) is configured to control the first level of liquid phase of the first heat exchange medium on the first heat exchange surface second side to be a) any percentage of the at least a portion of the reaction mixture on the first heat exchange surface first side which indirectly contacts a liquid phase of the first heat exchange medium on the first heat exchange surface second side disclosed herein, b) any percentage of the surface area of the first heat exchange surface second side which contacts the liquid phase of the first heat exchange medium disclosed herein, c) any volume ratio of the liquid phase of the first heat exchange medium in the first heat exchanger (or on the first heat exchange surface second side) to the vapor phase of the first heat exchange medium in the first heat exchanger (or on the first heat exchange surface second side) disclosed herein, or d) any combination thereof.

Statement 128. The reaction system of any one of Statements 124-127, wherein the heat exchange system further comprises i) a heat exchange medium inlet line in fluid communication with one of the one or more conduits of Statements 112-116, ii) a first control valve located on the first heat exchange fluid inlet line, iii) a heat exchange medium outlet line in fluid communication with one of the one or more conduits of Statements 112-116, and iv) a second control valve located on the heat exchange medium outlet line; wherein the first control valve is configured to control the addition of first heat exchange medium to the heat exchange system (or the first heat exchange medium circulation loop of Statement 116), and wherein the second control valve is configured to control the removal of first heat exchange medium from the heat exchange system (or the first heat exchange medium circulation loop of Statement 116).

Statement 129. The reaction system of Statement 128, wherein the first level indicator and/or controller (coupled to the first heat exchanger) is configured to (a) actuate the first control valve to an open position to add first heat exchange medium to the heat exchange system (or the first heat exchange medium circulation loop of Statement 116), and/or (b) actuate the second control valve to an open position to remove a portion of the first heat exchange medium from the heat exchange system (or the first heat exchange medium circulation loop of Statement 116).

Statement 130. The reaction system of any one of Statements 110-129, wherein the heat exchange system further comprises a second level indicator and/or controller (coupled to the second heat exchanger and) configured to measure, monitor, and/or control the second level of the liquid phase of the first heat exchange medium on the second heat exchange surface first side.

Statement 131. The reaction system of Statement 130, wherein the second level indicator and/or controller (coupled to the second heat exchanger and) is configured to control the second level of liquid phase of the first heat exchange medium of the second heat exchange surface first side to be i) any percentage of the second heat exchange medium on the second heat exchange surface second side which indirectly contacts the liquid phase of the first heat exchange medium on the second heat exchange surface first side disclosed herein, ii) any volume ratio of the liquid phase of the first heat exchange medium in the second heat exchanger (or on the second heat exchange surface first side) to the vapor phase of the first heat exchange medium in the second heat exchanger (or on the second heat exchange surface first side) disclosed herein, or iii) any combination thereof.

Statement 132. The reaction system of any one of Statements 110-131, wherein the heat exchange system further comprise a liquid control valve located on at least one of the plurality of conduits of Statements 113-116 allowing for flow of the first heat exchange medium from the second heat exchanger (or second heat exchange surface first side) to the first heat exchanger (or the first heat exchange surface second side).

Statement 133. The reaction system of Statement 132, wherein the liquid control valve is configured to control a second level of the liquid phase of the first heat exchange medium in the second heat exchanger (or on the second heat exchange surface first side).

Statement 134. The reaction system of Statement 132 or 133, wherein the liquid control valve is configured to control a first level of the liquid phase of the first heat exchange medium on the first heat exchange surface second side.

Statement 135. The reaction system of any one of Statements 130-131, wherein the second level indicator and/or controller is configured to actuate the liquid control valve of Statements 130-132.

Statement 136. The reaction system of any one of Statements 110-135, wherein the reaction system further comprises a temperature indicator and/or controller configured to measure, monitor, and/or control the reaction mixture temperature (or average reaction mixture temperature) within the reaction zone.

Statement 137. The reaction system of Statement 136, wherein the temperature indicator and/or controller is coupled to the liquid control valve of any one of Statements 132-134.

Statement 138. The reaction system of Statement 136 or 137, wherein temperature indicator and/or controller is configured to actuate the liquid control valve of any one of Statements 132-137 to control the first level of the liquid phase of the first heat exchange medium in the first heat exchanger (or on the first heat exchange surface second side) and/or the second level of the liquid phase of the first heat exchange medium in the second heat exchanger (or on the second heat exchange surface first side) in response to the reaction mixture temperature (or average reaction mixture temperature).

Statement 139. The reaction system of any one of Statements 136-138, wherein the temperature indicator and/or controller is coupled to at least one of the pressure control devices of any one of Statements 117-124.

Statement 140. The reaction system of Statement 139, wherein the temperature indicator and/or controller is configured to control a pressure set point of at least one of the one or more pressure control devices in response to reaction mixture temperature (or average reaction mixture temperature).

Statement 141. The reaction system of Statement 139 or 140, wherein the temperature indicator and/or controller is coupled to the control valve of any one of Statements 122-124.

Statement 142. The reaction system of Statement 141, wherein the temperature indicator and/or controller is configured to actuate the control valve to control the pressure on the first heat exchange surface second side and/or second heat exchange surface first side (and/or the first heat exchange medium) in response to the reaction mixture temperature (or average reaction mixture temperature).

Statement 143. The reaction system of Statements 136-142, wherein the temperature indicator and/or controller is a) coupled to at least one of the pressure control devices of any one of Statements 117-124 and configured to actuate the control valve of any one of Statements 122-124 to control a pressure set point of the one or more pressure control devices in response to reaction mixture temperature (or average reaction mixture temperature), b) coupled to the liquid control valve of Statements 132-136 and configured actuate the liquid control valve to i) control a first level of the liquid phase of the first heat exchange medium on the first heat exchange surface second side, ii) control the second level of the liquid phase of the first heat exchange medium on the second heat exchange surface first side, or any combination thereof, c) is coupled with the first level indicator or controller of statement 126 or 127 and configured to i) actuate the first control valve of Statement 128 or 129 to allow the addition of first heat exchange medium to the heat exchange system (or the first heat exchange medium circulation loop), and/or ii) actuate the second control valve of Statement 128 or 129 to allow the removal of first heat exchange medium from the heat exchange system (or the first heat exchange medium circulation loop) in response to reaction mixture temperature (or average reaction mixture temperature), or d) a combination thereof.

Statement 144. The reaction system of any one of Statements 110-143, wherein a second level of the liquid phase of the first heat exchange medium on the second heat exchange surface first side is vertically higher relative to a common reference point on the ground than the first level of the liquid phase of the first heat medium on the first heat exchange surface second side.

Statement 145. The reaction system of any one of Statements 110-144, wherein the second heat exchange surface comprises vertically oriented tubes or plates.

Statement 146. The reaction system any one of Statements 101-145, wherein the first heat exchange surface comprises horizontally oriented tubes or plates.

Statement 147. The reaction system of Statements 101-146, wherein the reaction system further comprises one or more reaction zone inlets to introduce one or more reaction mixture components into the reaction zone and one or more reaction zone outlets to remove reaction mixture from the reaction zone.

Statement 148. The reaction system of any one of Statements 101-147, where the first heat exchange medium has a boiling point at 1 atmosphere (101.3 kPa) greater than an average reaction mixture temperature on the first heat exchange surface first side and a boiling point at the pressure on the first heat exchange surface second side less than the average reaction mixture temperature on the first heat exchange surface first side.

Statement 149. The reaction system of any one of Statements 101-148, wherein a ratio of heat exchanged reaction mixture volume to the total reaction mixture volume within the reaction zone can have value disclosed herein (e.g., a minimum value of 1:1, 1.5:1, 2:1, 2.5:1, 3:1, or 4:1; a maximum value of 100:1, 50:1, 20:1, 15:1, 12:1, or 9:1; or in a range from 1:1 to 100:1, from 1.5:1 to 100:1, from 2:1 to 100:1, from 3:1 to 100:1, from 4:1 to 100:1, from 3:1 to 50:1, from 3:1 to 20:1, from 4:1 to 50:1, from 4:1 to 15:1, or from 4:1 to 12:1; among others disclosed herein).

Statement 150. The reaction system of any one of Statements 101-149, where a temperature difference between an average reaction mixture temperature on the first heat exchange surface first side and a first heat exchange medium temperature on the first heat exchange surface second side can be (or can be controlled to be) any temperature difference disclosed herein (e.g., less than 20° C., 15° C., 10° C. 7.5° C., 5° C., 4° C., or 3° C.).

Statement 151. The reaction system of any one of Statements 101-150, wherein the first heat exchange medium temperature on the first heat exchange surface second side can be (or can be controlled to be) within any percentage of an average reaction mixture temperature on the first heat exchange surface first side disclosed herein (e.g., 20%, 15%, 12.5%, 10%, 7.5%, 6%, 5%, or 4.5%).

Statement 152. The reaction system of any one of Statements 101-151, wherein a reaction mixture temperature at any point in the reaction zone can be, or can be controlled to be, within any value of an average reaction mixture temperature in the reaction zone disclosed herein (e.g., within 15° C. 10° C., 7.5° C., 5° C., 4° C., 3° C., or 2° C.).

Statement 153. The reaction system of any one of Statements 101-152, wherein a reaction mixture temperature at any point in the reaction zone can be, or can be controlled to be, within any percentage of an average reaction mixture temperature in the reaction zone disclosed herein (e.g., within 3%, 2%, 1.5%, 1%, 0.8%, 0.6%, 0.5%, 0.45%, 0.4%, 0.35%, 0.3%, 0.25%, or 0.2%).

Statement 154. The reaction system of Statements 101-153, wherein the reaction zone of the reaction system comprises at least a portion of the first heat exchange surface first side (of the first heat exchanger).

Statement 155. The reaction system of Statement 154, wherein the reaction system further comprises i) one or more reaction mixture component feed lines configured to introduce one or more reaction mixture components into the first heat exchanger, and ii) reaction zone outlet lines which removes the reaction mixture from the reaction zone or the first heat exchanger.

Statement 156. The reaction system of Statements 101-153, wherein the reaction zone of the reaction system comprises one or more reaction zone lines where i) at least one of the two or more reaction zone lines is a reaction zone first heat exchanger inlet line(s) (containing the reaction mixture and) coupled to one or more first heat exchanger inlets configured to introduce the reaction mixture into the first heat exchanger to contact the reaction mixture with the first heat exchange surface first side, ii) at least one of the two or more reaction zone lines is a reaction zone first heat exchanger outlet line(s) (containing reaction mixture and) coupled to one or more first heat exchanger outlet(s) configured to remove reaction mixture from the first heat exchanger and from contacting the first heat exchange surface first side.

Statement 157. The reaction system of Statement 156, wherein the reaction zone of the reaction system further comprises a motive device fluidly connecting the reaction zone first heat exchanger inlet line(s) and the reaction zone first heat exchanger outlet line(s) configured to form a reaction mixture circulation loop, where the motive device is configured to circulate the reaction mixture through the reaction mixture circulation loop.

Statement 158. The reaction system of Statement 156 or 157, further comprising a reactor fluidly connected to a reaction zone first heat exchanger inlet line(s), a reaction zone first heat exchanger outlet line(s), and first heat exchange surface first side.

Statement 159. The reaction system of any one of Statements 101-158, wherein the reaction system is selected from the group consisting of an ethylene oligomerization reaction system, an ethylene trimerization reaction system, an ethylene tetramerization reaction system, or an ethylene trimerization and tetramerization reaction system.

Statement 159. The reaction system of Statements 156-159, w % herein the reaction system further comprises a) one or more reaction zone inlets (coupled to a reaction line), each reaction zone inlet configured to introduce one or more of 1) ethylene, 2) a catalyst system or catalyst system components comprising i) a heteroatomic ligand transition metal compound complex and any organoaluminum compound, or ii) any heteroatomic ligand, a transition metal compound, and an organoaluminum compound, 3) optionally, a first organic reaction medium, and 4) optionally, hydrogen into a reaction mixture within the reaction zone, and b) one or more reaction zone outlets, each reaction outlet configured to withdrawal reaction mixture from the reaction zone.

Statement 201. The process of Statement 46 or the reaction system of Statement 160, wherein the heteroatomic ligand or the heteroatomic ligand of the heteroatomic ligand transition metal compound complex has structure NPF 1, NPA 1, Gu 2, Gu 3, Gu 4, Gu 5, HCPA 1, or any combination thereof;

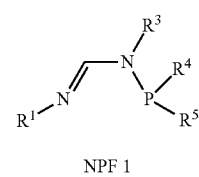

NPF 1

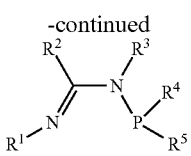

NPA 1

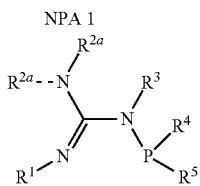

Gu 1

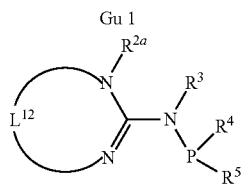

Gu 2

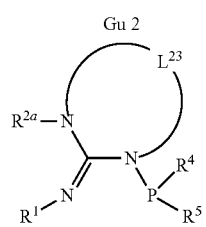

Gu 3

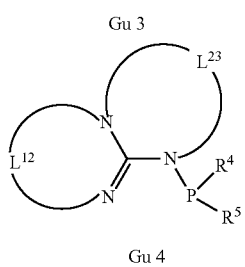

Gu 4

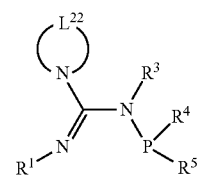

Gu 5

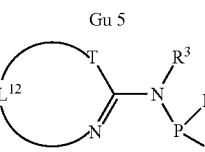

HCPA 1 wherein:
$R^1$ is a hydrogen or a $C_1$ to $C_2$ organyl group;
$R^2$ is a $C_1$ to $C_{20}$ organyl group;
T is oxygen or sulfur;
$R^{2a}$ and $R^{2b}$ independently are $C_1$ to $C_{20}$ organyl groups;
$L^{12}$ and $L^{23}$ independently are $C_2$ to $C_{20}$ organylene groups;
$L^{22}$ is a $C_3$ to $C_{20}$ organylene groups;
$R^3$ is hydrogen or a $C_1$ to $C_{20}$ organyl group; and
$R^4$ and $R^5$ independently are hydrogen or a $C_1$ to $C_{20}$ organyl groups;

where $R^1$ and $R^2$ are optionally joined to form $L^{12r}$, and $L^{12r}$ is a $C_3$ to $C_{30}$ organylene group; and
where $R^4$ and $R^5$ are optionally joined to form $L^{45}$, and $L^{45}$ is a $C_4$ to $C_{30}$ organylene group.

Statement 202. The process or reaction system of Statement 201, wherein:
$R^1$ is a hydrogen or a $C_1$ to $C_{20}$ hydrocarbyl group;
$R^2$ is a $C_1$ to $C_{20}$ hydrocarbyl group;
$R^{2a}$ and $R^{2b}$ independently are $C_1$ to $C_{20}$ hydrocarbyl groups;
$L^{12}$ and $L^{23}$ independently are $C_2$ to $C_{20}$ hydrocarbylene groups;
$L^{22}$ is a $C_3$ to $C_{20}$ hydrocarbylene groups;
$R^3$ is hydrogen or a $C_1$ to $C_{20}$ hydrocarbyl group; and
$R^4$ and $R^5$ independently are $C_1$ to $C_{20}$ hydrocarbyl groups;
where $R^1$ and $R^2$ are optionally joined to form $L^{12r}$, and $L^{12r}$ is a $C_3$ to $C_{20}$ hydrocarbylene group; and
where $R^4$ and $R^5$ are optionally joined to form $L^{45}$, and $L^{45}$ is a $C_4$ to $C_{20}$ hydrocarbylene group.

Statement 203. The process of Statement 46 or the reaction system of Statement 155, wherein the heteroatomic ligand or the heteroatomic ligand of the heteroatomic ligand transition metal compound complex has structure NRN 1, PRP 1, SRS 2, PNP 3, NRNRN 4, PRPRP 5, SRSRS 1, NRPRN 1, or any combination thereof:

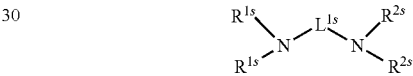

NRN 1

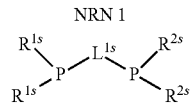

PRP 1

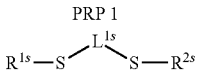

SRS 1

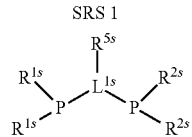

PNP 1

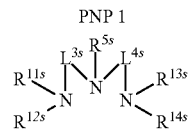

NRNRN 1

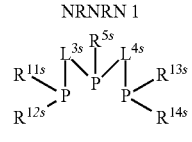

PRPRP 1

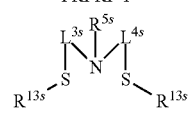

SRSRS 1

-continued

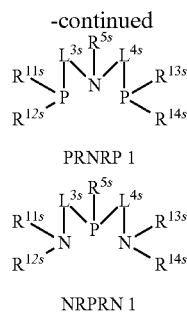

PRNRP 1

NRPRN 1 wherein:
each $R^{1s}$, $R^{2s}$, $R^{5s}$, $R^{11s}$, $R^{12s}$, $R^{13s}$, and $R^{14s}$, independently, is selected from a hydrogen or a $C_1$ to $C_{20}$ organyl group;
each $L^{1s}$, $L^{3s}$, and $L^{4s}$, independently, is selected from a $C_2$ to $C_{20}$ organylene group; and
any two geminal $R^{1s}$ are optionally joined to form $L^{1sr}$, and $L^{1sr}$ is a $C_3$ to $C_{30}$ organylene group;
any two geminal $R^{2s}$ are optionally joined to form $L^{2sr}$, and $L^{2sr}$ is a $C_3$ to $C_{30}$ organylene group;
any germinal $R^{11s}$ sand $R^{12s}$ are optionally joined to form $L^{12sr}$, and $L^{12sr}$ is a $C_3$ to $C_{30}$ organylene group; and
any germinal $R^{13s}$ and $R^{14s}$ are optionally joined to form $L^{34sr}$, and $L^{34sr}$ is a $C_3$ to $C_{30}$ organylene group.

Statement 204. The process or reaction system of Statement 203, wherein
each $R^{1s}$, $R^{2s}$, $R^{5s}$, $R^{11s}$, $R^{12s}$, $R^{13s}$, and $R^{14s}$, independently, is selected from a hydrogen or a $C_1$ to $C_{20}$ hydrocarbyl group;
each $L^{1s}$, $L^{3s}$, and $L^{4s}$, independently, is selected from a $C_2$ to $C_{20}$ hydrocarbylene group;
any two geminal $R^{1s}$ are optionally joined to form $L^{1sr}$, and $L^{1sr}$ is a $C_2$ to $C_{20}$ hydrocarbylene group;
any two geminal $R^{2s}$ are optionally joined to form $L^{2sr}$, and $L^{2sr}$ is a $C_2$ to $C_{20}$ hydrocarbylene group;
any germinal $R^{11s}$ and $R^{12s}$ are optionally joined to form $L^{12sr}$, and $L^{12sr}$ is a $C_2$ to $C_{20}$ hydrocarbylene group; and
any germinal $R^{13s}$ and $R^{14s}$ are optionally joined to form $L^{34sr}$, and $L^{34sr}$ is a $C_2$ to $C_{20}$ hydrocarbylene group.

Statement 205. The process or reaction system of any one of Statements 201-203, wherein the transition metal compound or the transition metal compound of the heteroatomic ligand transition metal compound is a chromium compound.

Statement 205. The process or reaction system of any one of Statements 201-203, wherein the organoaluminum compound comprises an aluminoxane. While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

What is claimed is:
1. A process comprising:
a) introducing at least 1) ethylene, 2) a catalyst system or catalyst system components comprising i) a heteroatomic ligand transition metal compound complex and an organoaluminum compound or ii) a heteroatomic ligand, a transition metal compound, and an organoaluminum compound, 3) optionally, an organic reaction medium, and 4) optionally, hydrogen into a reaction mixture within a reaction zone;
b) forming an oligomer product in the reaction zone; and
c) controlling a reaction mixture temperature within the reaction zone with a heat exchange system comprising a first heat exchanger providing indirect contact between at least a portion of the reaction mixture and a first heat exchange medium, the first heat exchanger comprising a first heat exchange surface having
i) a first heat exchange surface first side in contact with the at least a portion of the reaction mixture, and
ii) a first heat exchange surface second side in contact with the first heat exchange medium:
where a pressure on the first heat exchange surface second side is less than 1 atmosphere (101.3 kPa),
where the first heat exchange medium has a boiling point at 1 atmosphere (101.3 kPa) greater than an average reaction mixture temperature on the first heat exchange surface first side and a boiling point at the pressure on the first heat exchange surface second side less than the average reaction mixture temperature on the first heat exchange surface first side, and
where a temperature difference between the average reaction mixture temperature on the first heat exchange surface first side and a first heat exchange medium temperature on the first heat exchange surface second side is less than 20° C.

2. The process of claim 1, wherein a first part of the at least a portion of the reaction mixture on the first heat exchange surface first side indirectly contacts a liquid phase of the first heat exchange medium on the first heat exchange surface second side and a second part of the at least a portion of the reaction mixture on the first heat exchange surface first side indirectly contacts a vapor phase of the first heat exchange medium that are on the first heat exchange surface second side.

3. The process of claim 2, wherein a volume ratio of the liquid phase to the vapor phase of the first heat exchange medium on the first heat exchange surface second side is in a range from 1:1 to about 9:1.

4. The process of claim 2, further comprising:
controlling the reaction mixture temperature by controlling a first level of the liquid phase of the first heat exchange medium on the first heat exchange surface second side, controlling the pressure on the pressure on the first heat exchange surface second side, or any combination thereof.

5. The process of claim 4, wherein controlling the first level of the liquid phase of the first heat exchange medium comprises:
adding or removing first heat exchange medium to or from the heat exchange system.

6. The process of claim 4, wherein the first level of the liquid phase of the first heat exchange medium is controlled such that 50% to 90% of a surface area of the first heat exchange surface second side contacts the liquid phase of first heat exchange medium.

7. The process of claim 1, wherein the heat exchange system further comprises one or more pressure control devices in fluid communication with the first heat exchange surface second side, the one or more pressure control devices providing the pressure of less than 1 atmosphere (101.3 kPa) on the first heat exchange surface second side.

8. The process of claim 7, further comprising:
controlling a pressure on the first heat exchange surface second side to provide the reaction mixture temperature within the reaction zone.

9. The process of claim 8, wherein controlling a pressure on the first heat exchange surface second side comprises adjusting a pressure set point on the one or more pressure control devices.

10. The process of claim 1, wherein the heat exchange system further comprises a second heat exchanger providing indirect contact between the first heat exchange medium and a second heat exchange medium, the second heat exchanger comprising a second heat exchange surface having
   i) a second heat exchange surface first side in contact with the first heat exchange medium, and
   ii) a second heat exchange surface second side in contact with the second heat exchange medium;
   where the second heat exchanger is fluidly connected to the first heat exchanger via a plurality of conduits allowing for flow of the first heat exchange medium between the first heat exchange surface second side and the second heat exchange surface first side,
   where the second heat exchange surface does not contact the reaction mixture, and
   where a pressure on the second heat exchange surface first side is less than 1 atmosphere (101.3 kPa).

11. The process of claim 10, wherein a first part of the at least a portion of the reaction mixture on the first heat exchange surface first side indirectly contacts a liquid phase of the first heat exchange medium on the first heat exchange surface second side and a second part of the at least a portion of the reaction mixture on the first heat exchange surface first side indirectly contacts a vapor phase of the first heat exchange medium on the first heat exchange surface second side, and
   wherein at least a first part of the second heat exchange medium on the second heat exchange surface second side indirectly contacts the vapor phase of the first heat exchange medium on the second heat exchange surface first side and a second part of the second heat exchange medium on the second heat exchange surface second side indirectly contacts liquid phase of the first heat exchange medium on the second heat exchange surface first side.

12. The process of claim 11, wherein controlling the reaction mixture temperature comprises:
   controlling a first level of the liquid phase of the first heat exchange medium on the first heat exchange surface second side.

13. The process of claim 12, wherein the first level of the liquid phase of the first heat exchange medium on the first heat exchange surface second side is controlled by:
   controlling a second level of a liquid phase of the first heat exchange medium on the second heat exchange surface first side,
   adding or removing first heat exchange medium to or from the heat exchange system, or any combination thereof.

14. The process of claim 10, wherein the heat exchange system further comprises one or more pressure control devices in fluid communication with at least one the one of the plurality of conduits, the one or more pressure control devices providing the pressure of less than 1 atmosphere (101.3 kPa) on the first heat exchange surface second side and on the second heat exchange surface first side.

15. The process of claim 11, wherein a second level of the liquid phase of the first heat exchange medium on the second heat exchange surface first side is vertically higher relative to a common reference point on the ground than the first level of the liquid phase of the first heat medium on the first heat exchange surface second side.

16. The process of claim 10, wherein the first heat exchange surface comprises horizontally oriented tubes or plates, wherein the second heat exchange surface comprises vertically oriented tubes or plates.

17. The process of claim 1, wherein the first heat exchange medium comprises water.

18. The process of claim 1, wherein a ratio of heat exchanged reaction mixture volume to the total reaction mixture volume within the reaction zone is in a range from 0.7 to 1.0.

19. The process of claim 1, wherein the first heat exchange medium temperature on the first heat exchange surface second side is within 4.5% of the average reaction mixture temperature on the first heat exchange surface first side.

20. The process of claim 1, wherein the reaction mixture temperature at any point in the reaction zone is within ±3% of the average reaction mixture temperature in the reaction zone.

* * * * *